United States Patent
Lindsey et al.

(10) Patent No.: US 12,139,617 B2
(45) Date of Patent: Nov. 12, 2024

(54) POLYMERIC FLUOROPHORES, COMPOSITIONS COMPRISING THE SAME, AND METHODS OF PREPARING AND USING THE SAME

(71) Applicant: North Carolina State University, Raleigh, NC (US)

(72) Inventors: Jonathan S. Lindsey, Raleigh, NC (US); Gongfang Hu, Cary, NC (US); Rui Liu, Cary, NC (US)

(73) Assignee: North Carolina State University, Raleigh, NC (US)

( * ) Notice: Subject to any disclaimer, the term of this patent is extended or adjusted under 35 U.S.C. 154(b) by 980 days.

(21) Appl. No.: 16/955,152

(22) PCT Filed: Dec. 18, 2018

(86) PCT No.: PCT/US2018/066195
§ 371 (c)(1),
(2) Date: Jun. 18, 2020

(87) PCT Pub. No.: WO2019/126144
PCT Pub. Date: Jun. 27, 2019

(65) Prior Publication Data
US 2020/0385583 A1    Dec. 10, 2020

Related U.S. Application Data

(60) Provisional application No. 62/714,541, filed on Aug. 3, 2018, provisional application No. 62/609,494, filed on Dec. 22, 2017.

(51) Int. Cl.
*C09B 69/10*    (2006.01)
*A61K 49/00*    (2006.01)
(Continued)

(52) U.S. Cl.
CPC ........ *C09B 69/108* (2013.01); *A61K 49/0032* (2013.01); *A61K 49/0054* (2013.01);
(Continued)

(58) Field of Classification Search
None
See application file for complete search history.

(56) References Cited

U.S. PATENT DOCUMENTS 5,915,925 A    6/1999    North
6,208,553 B1   3/2001    Gryko et al.
(Continued)

FOREIGN PATENT DOCUMENTS

AU    2014202199 A1    5/2014
EP    0002963 A1       7/1979
(Continued)

OTHER PUBLICATIONS

Miksa, et al, "Fluorescent Dyes Used in Polymer Carriers as Imaging Agents in Anticancer Therapy," Medicinal Chemistry, 6:611-639 (2016) (Year: 2016).*

(Continued)

*Primary Examiner* — Fred M Teskin
(74) *Attorney, Agent, or Firm* — Myers Bigel, P.A.

(57) ABSTRACT

Described herein are polymeric fluorophores that include a dye, a polymer, and optionally a bioconjugate group. A polymeric fluorophore may have a structure represented by: A-B-C or C-A-B, wherein A is a dye; B is a polymer comprising one or more hydrophobic unit(s) and one or more hydrophilic unit(s); and optionally C, wherein C, when present, comprises a bioconjugate group. Also described herein are compositions comprising the polymeric fluorophores and methods of preparing and using the same.

13 Claims, 6 Drawing Sheets

(51) Int. Cl.
  *C08F 293/00* (2006.01)
  *C08L 33/08* (2006.01)
(52) U.S. Cl.
  CPC .......... *C08F 293/005* (2013.01); *C08L 33/08* (2013.01); *C08F 2438/03* (2013.01); *C08L 2207/53* (2013.01)

(56) References Cited

U.S. PATENT DOCUMENTS

| | | | |
|---|---|---|---|
| 6,212,093 B1 | 4/2001 | Lindsey | |
| 6,248,590 B1 | 6/2001 | Malachowski | |
| 6,272,038 B1 | 8/2001 | Clausen et al. | |
| 6,407,330 B1 | 6/2002 | Lindsey et al. | |
| 6,420,648 B1 | 7/2002 | Lindsey | |
| 6,451,942 B1 | 9/2002 | Li et al. | |
| 6,498,945 B1 | 12/2002 | Alfheim et al. | |
| 6,559,374 B2 | 5/2003 | Lindsey et al. | |
| 6,589,792 B1 | 7/2003 | Malachowski | |
| 6,603,070 B2 | 8/2003 | Lindsey et al. | |
| 6,642,376 B2 | 11/2003 | Lindsey et al. | |
| 6,657,884 B2 | 12/2003 | Bocian et al. | |
| 6,728,129 B2 | 4/2004 | Lindsey et al. | |
| 6,765,092 B2 | 7/2004 | Lindsey et al. | |
| 6,849,730 B2 | 2/2005 | Lindsey et al. | |
| 6,890,487 B1 | 5/2005 | Sklar et al. | |
| 6,916,982 B2 | 7/2005 | Loewe et al. | |
| 6,924,375 B2 | 8/2005 | Lindsey et al. | |
| 6,944,047 B2 | 9/2005 | Rotenberg et al. | |
| 6,946,552 B2 | 9/2005 | Lindsey et al. | |
| 7,005,237 B2 | 2/2006 | Lindsey | |
| 7,022,862 B2 | 4/2006 | Lindsey et al. | |
| 7,148,361 B2 | 12/2006 | Lindsey et al. | |
| 7,153,975 B2 | 12/2006 | Lindsey et al. | |
| 7,317,108 B2 | 1/2008 | Lindsey et al. | |
| 7,323,561 B2 | 1/2008 | Lindsey et al. | |
| 7,332,599 B2 | 2/2008 | Yu et al. | |
| 7,378,520 B2 | 5/2008 | Lindsey et al. | |
| 7,501,507 B2 | 3/2009 | Balakumar et al. | |
| 7,501,508 B2 | 3/2009 | Lindsey et al. | |
| 7,534,807 B2 | 5/2009 | Kim et al. | |
| 7,582,751 B2 | 9/2009 | Lindsey et al. | |
| 7,633,007 B2 | 12/2009 | Lindsey et al. | |
| 7,745,618 B2 | 6/2010 | Kiper et al. | |
| 7,799,910 B2 | 9/2010 | Lindsey et al. | |
| 7,884,280 B2 | 2/2011 | Lindsey | |
| 7,919,770 B2 | 4/2011 | Youngblood et al. | |
| 7,994,312 B2 | 8/2011 | Lindsey et al. | |
| 8,097,609 B2 | 1/2012 | Borbas et al. | |
| 8,158,340 B2 | 4/2012 | Omalley | |
| 8,187,824 B2 | 5/2012 | Lindsey | |
| 8,207,329 B2 | 6/2012 | Lindsey et al. | |
| 8,278,340 B2 | 10/2012 | Melander et al. | |
| 8,419,985 B2 | 4/2013 | Miteva et al. | |
| 8,574,465 B2 | 11/2013 | Miteva et al. | |
| 8,716,420 B2 | 5/2014 | Janczewski et al. | |
| 8,765,098 B2 | 7/2014 | Appel et al. | |
| 9,040,626 B2 | 5/2015 | Chien et al. | |
| 9,303,165 B2 | 4/2016 | Lindsey et al. | |
| 9,333,179 B2 | 5/2016 | Zhang et al. | |
| 9,365,722 B2 | 6/2016 | Lindsey et al. | |
| 9,532,956 B2 | 1/2017 | Radovic-Moreno et al. | |
| 9,597,405 B2 | 3/2017 | Lee et al. | |
| 9,662,387 B2 | 5/2017 | Neumann et al. | |
| 9,715,187 B2 | 7/2017 | Mukumoto et al. | |
| 10,363,313 B2 | 7/2019 | Basilion et al. | |
| 10,407,683 B2 | 9/2019 | Nelson et al. | |
| 10,426,753 B2 | 10/2019 | Roy et al. | |
| 10,502,733 B2 | 12/2019 | Chiu et al. | |
| 10,513,802 B2 | 12/2019 | Omenetto et al. | |
| 10,550,205 B2 | 2/2020 | Aiertza Otxotorena et al. | |
| 10,577,554 B2 | 3/2020 | Kheir et al. | |
| 10,646,549 B2 | 5/2020 | Frederick et al. | |
| 10,660,828 B2 | 5/2020 | Deng et al. | |
| 10,669,311 B2 | 6/2020 | Teesalu et al. | |
| 10,709,779 B2 | 7/2020 | Ciaramella et al. | |
| 10,729,652 B2 | 8/2020 | Karathanasis et al. | |
| 10,730,924 B2 | 8/2020 | Ticho et al. | |
| 10,736,854 B2 | 8/2020 | Popov et al. | |
| 10,738,068 B2 | 8/2020 | Horcajada-Cortes et al. | |
| 10,745,704 B2 | 8/2020 | Defougerolles et al. | |
| 10,770,197 B2 | 9/2020 | Chiu et al. | |
| 2002/0032252 A1 | 3/2002 | Ishizuka | |
| 2004/0091541 A1 | 5/2004 | Unger | |
| 2006/0083781 A1 | 4/2006 | Shastri et al. | |
| 2007/0105990 A1 | 5/2007 | Makino et al. | |
| 2008/0095699 A1 | 4/2008 | Zheng et al. | |
| 2008/0213377 A1 | 9/2008 | Bhatia et al. | |
| 2009/0047272 A1 | 2/2009 | Appelbaum et al. | |
| 2009/0104614 A1 | 4/2009 | Tsourkas et al. | |
| 2010/0144845 A1 | 6/2010 | Farokhzad et al. | |
| 2010/0210742 A1 | 8/2010 | Iyoda et al. | |
| 2010/0226991 A1 | 9/2010 | Horcajada-Cortes et al. | |
| 2010/0260677 A1 | 10/2010 | Bhatia et al. | |
| 2010/0311903 A1 | 12/2010 | Rajagopalan | |
| 2011/0022129 A1 | 1/2011 | Prud et al. | |
| 2011/0081293 A1 | 4/2011 | Kastantin et al. | |
| 2011/0104052 A1 | 5/2011 | Barnett et al. | |
| 2011/0206613 A1 | 8/2011 | Wiehe et al. | |
| 2012/0046329 A1 | 2/2012 | Roth et al. | |
| 2012/0095075 A1 | 4/2012 | Manoharan et al. | |
| 2012/0282632 A1 | 11/2012 | Chiu et al. | |
| 2013/0063334 A1 | 3/2013 | Gibson et al. | |
| 2013/0149252 A1 | 6/2013 | Hara et al. | |
| 2013/0280751 A1 | 10/2013 | Papkovsky et al. | |
| 2014/0255477 A1 | 9/2014 | Ghoroghchian | |
| 2014/0357806 A1 | 12/2014 | Song et al. | |
| 2015/0140587 A1 | 5/2015 | Darzins et al. | |
| 2015/0152187 A1 | 6/2015 | Sun et al. | |
| 2015/0268229 A1 | 9/2015 | Chiu et al. | |
| 2016/0018405 A1 | 1/2016 | Chiu | |
| 2016/0067276 A1 | 3/2016 | Polizzotti et al. | |
| 2016/0089436 A1 | 3/2016 | Hyeon et al. | |
| 2016/0089455 A1 | 3/2016 | Hyeon et al. | |
| 2016/0194368 A1 | 7/2016 | Hoge et al. | |
| 2016/0194625 A1 | 7/2016 | Hoge et al. | |
| 2016/0243047 A1 | 8/2016 | Thayumanavan et al. | |
| 2016/0317676 A1 | 11/2016 | Hope et al. | |
| 2017/0002060 A1 | 1/2017 | Bolen et al. | |
| 2017/0003293 A1 | 1/2017 | Chiu et al. | |
| 2017/0151339 A1 | 6/2017 | White et al. | |
| 2017/0168041 A1 | 6/2017 | Liu et al. | |
| 2017/0173128 A1 | 6/2017 | Hoge et al. | |
| 2017/0188922 A1 | 7/2017 | Lee et al. | |
| 2017/0202979 A1 | 7/2017 | Chakraborty et al. | |
| 2017/0204152 A1 | 7/2017 | Nelson et al. | |
| 2017/0210788 A1 | 7/2017 | Huang et al. | |
| 2017/0224821 A1 | 8/2017 | Boyden et al. | |
| 2017/0226507 A1 | 8/2017 | Chan et al. | |
| 2017/0246236 A1 | 8/2017 | Agemy et al. | |
| 2017/0348415 A1 | 12/2017 | Hoge et al. | |
| 2017/0362605 A1 | 12/2017 | Chakraborty | |
| 2018/0000885 A1 | 1/2018 | Dewitt et al. | |
| 2018/0085391 A1 | 3/2018 | Bouchon et al. | |
| 2018/0214579 A1 | 8/2018 | Almarsson et al. | |
| 2018/0291374 A1 | 10/2018 | Bloch et al. | |
| 2018/0369384 A1 | 12/2018 | Manoharan et al. | |
| 2019/0016781 A1 | 1/2019 | Bolen et al. | |
| 2019/0054112 A1 | 2/2019 | Gregoire | |
| 2019/0106542 A1 | 4/2019 | Chiu et al. | |
| 2019/0142971 A1 | 5/2019 | Hoge et al. | |
| 2019/0175517 A1 | 6/2019 | Martini et al. | |
| 2019/0192653 A1 | 6/2019 | Hoge et al. | |
| 2019/0194532 A1 | 6/2019 | York et al. | |
| 2019/0234953 A1 | 8/2019 | Chiu et al. | |
| 2019/0248864 A1 | 8/2019 | Ellsworth et al. | |
| 2019/0264102 A1 | 8/2019 | Pitner et al. | |
| 2019/0275170 A1 | 9/2019 | Benenato et al. | |
| 2019/0298657 A1 | 10/2019 | Martini et al. | |
| 2019/0298658 A1 | 10/2019 | Benenato et al. | |
| 2019/0300906 A1 | 10/2019 | Martini et al. | |
| 2019/0302026 A1 | 10/2019 | Wooley et al. | |
| 2019/0307687 A1 | 10/2019 | Karathanasis et al. | |
| 2019/0328677 A1 | 10/2019 | Kim et al. | |
| 2019/0351071 A1 | 11/2019 | Ahmad et al. | |

(56) References Cited

U.S. PATENT DOCUMENTS

| | | |
|---|---|---|
| 2019/0382774 A1 | 12/2019 | Hoge et al. |
| 2019/0390181 A1 | 12/2019 | Benenato et al. |
| 2020/0002376 A1 | 1/2020 | Gillies et al. |
| 2020/0011874 A1 | 1/2020 | Chiu et al. |
| 2020/0054628 A1 | 2/2020 | Song |
| 2020/0054772 A1 | 2/2020 | Prud'Homme et al. |
| 2020/0078314 A1 | 3/2020 | Martini et al. |
| 2020/0085916 A1 | 3/2020 | Martini et al. |
| 2020/0102363 A1 | 4/2020 | Mishra et al. |
| 2020/0113821 A1 | 4/2020 | Saltzman et al. |
| 2020/0121808 A1 | 4/2020 | Bilodeau et al. |
| 2020/0131498 A1 | 4/2020 | Martini et al. |
| 2020/0149052 A1 | 5/2020 | Martini et al. |
| 2020/0158724 A1 | 5/2020 | Chiu et al. |
| 2020/0179287 A1 | 6/2020 | Medina et al. |
| 2020/0190487 A1 | 6/2020 | Zhang et al. |
| 2020/0190515 A1 | 6/2020 | Vargeese et al. |
| 2020/0221954 A1 | 7/2020 | Singh et al. |
| 2020/0255833 A1 | 8/2020 | Manoharan et al. |
| 2020/0270134 A1 | 8/2020 | Nel et al. |
| 2020/0297624 A1 | 9/2020 | Popov et al. |
| 2020/0297854 A1 | 9/2020 | Ingber et al. |
| 2020/0312481 A1 | 10/2020 | Chiu et al. |
| 2023/0086985 A1* | 3/2023 | Lindsey ............... C09B 69/105 |
| 2023/0248852 A1 | 8/2023 | Prud'Homme et al. |

FOREIGN PATENT DOCUMENTS

| | | |
|---|---|---|
| EP | 2329035 A2 | 6/2011 |
| EP | 2420547 A1 | 2/2012 |
| EP | 2517537 B1 | 4/2019 |
| EP | 3704059 A1 | 9/2020 |
| EP | 3721875 A1 | 10/2020 |
| JP | 2011520901 A | 7/2011 |
| JP | 2012162677 A | 8/2012 |
| JP | 2015199949 A | 11/2015 |
| JP | 2017507191 A | 3/2017 |
| WO | 2005115444 A2 | 12/2005 |
| WO | 2009140432 A2 | 11/2009 |
| WO | 2010044752 A1 | 4/2010 |
| WO | 2010054266 A2 | 5/2010 |
| WO | 2010077678 A2 | 7/2010 |
| WO | 2010148395 A1 | 12/2010 |
| WO | 2011143524 A2 | 11/2011 |
| WO | 2012039741 A1 | 3/2012 |
| WO | 2011126882 A9 | 4/2012 |
| WO | 2012018881 A3 | 8/2012 |
| WO | 2012177639 A3 | 5/2013 |
| WO | 2013139391 A1 | 9/2013 |
| WO | 2013166436 A1 | 11/2013 |
| WO | 2013185032 A1 | 12/2013 |
| WO | 2014106208 A1 | 7/2014 |
| WO | 2014187440 A2 | 11/2014 |
| WO | 2015034928 A1 | 3/2015 |
| WO | 2015051214 A1 | 4/2015 |
| WO | 2015058069 A1 | 4/2015 |
| WO | 2015066444 A1 | 5/2015 |
| WO | 2015153345 A1 | 10/2015 |
| WO | 2016114634 A2 | 7/2016 |
| WO | 2016164762 A1 | 10/2016 |
| WO | 2017106799 A1 | 6/2017 |
| WO | 2017201340 A2 | 11/2017 |
| WO | 2017201349 A1 | 11/2017 |
| WO | 2017201350 A1 | 11/2017 |
| WO | 2018035281 A1 | 2/2018 |
| WO | 2018/044688 | 3/2018 |
| WO | 2018102252 A1 | 6/2018 |
| WO | 2018106933 A1 | 6/2018 |
| WO | 2018106945 A1 | 6/2018 |
| WO | 2018/156955 | 8/2018 |
| WO | 2019027370 A1 | 2/2019 |
| WO | 2019118778 A1 | 6/2019 |
| WO | 2019126144 A1 | 6/2019 |
| WO | 2019147824 A1 | 8/2019 |
| WO | 2019183164 A1 | 9/2019 |
| WO | 2019183295 A1 | 9/2019 |
| WO | 2019191482 A1 | 10/2019 |
| WO | 2019246271 A1 | 12/2019 |
| WO | 2019246273 A1 | 12/2019 |
| WO | 2019246455 A1 | 12/2019 |
| WO | 2020036875 A1 | 2/2020 |
| WO | 2020076553 A1 | 4/2020 |
| WO | 2019246312 A9 | 6/2020 |
| WO | 2019246313 A9 | 7/2020 |
| WO | 2019246317 A9 | 7/2020 |
| WO | 2020117840 A3 | 7/2020 |
| WO | 2020121313 A8 | 8/2020 |
| WO | 2021118782 A2 | 6/2021 |
| WO | 2022147533 A1 | 7/2022 |

OTHER PUBLICATIONS

Deng et al. "Elucidating the Stability of Single-Chain Polymeric Nanoparticles in Biological Media and Living Cells" Biomacromolecules, 23:326-338 (2022).

Liu et al. "Catalytically Active Single-Chain Polymeric Nanoparticles: Exploring Their Functions in Complex Biological Media" Journal of the American Chemical Society, 140:3423-3433 (2018).

Aqil et al. "Coating of gold nanoparticles by thermosensitive poly(N-isopropylacrylamide) end-capped by biotin" Polymer, 49:1145-1153 (2008).

Arslan et al. "Bioinspired Anchorable Thiol-Reactive Polymers: Synthesis and Applications Toward Surface Functionalization of Magnetic Nanoparticles" Macromolecules, 47:5124-5134 (2014).

Bao et al. "Rhodamine B-Based Derivative: Synthesis, Crystal Structure Analysis, Molecular Simulation, and Its Application as a Selective Fluorescent Chemical Sensor for Sn2+" Molecules, 19:7817-7831 (2014).

Bardajee et al. "pH-Responsive fluorescent dye-labeled metal-chelating polymer with embedded cadmium telluride quantum dots for controlled drug release of doxorubicin" Reactive and Functional Polymers, 133:45-56 (2018).

Basle et al. "Protein Chemical Modification on Endogenous Amino Acids" Chemistry & Biology, 17:213-227 (2010).

Bathfield et al. "Versatile Precursors of Functional RAFT Agents. Application to the Synthesis of Bio-Related End-Functionalized Polymers" Journal of the American Chemical Society, 128:2546-2547 (2006).

Battistella et al. "Synthesis and Postpolymerization Modification of Fluorine-End-Labeled Poly(Pentafluorophenyl Methacrylate) Obtained via RAFT Polymerization" ACS Omega, 3:9710-9721 (2018).

Bays et al. "Synthesis of Semitelechelic Maleimide Poly(PEGA) for Protein Conjugation by RAFT Polymerization" Biomacromolecules, 10:1777-1781 (2009).

Beija et al. "Fluorescence Anisotropy of Hydrophobic Probes in Poly(N-decylacrylamide)-block-poly(N,N-diethylacrylamide) Block Copolymer Aqueous Solutions: Evidence of Premicellar Aggregates" The Journal of Physical Chemistry B, 114:9977-9986 (2010).

Beija et al. "Novel Malachite Green- and Rhodamine B-labeled cationic chain transfer agents for RAFT polymerization" Polymer, 5933-5946 (2011).

Biedermann et al. "Postpolymerization Modification of Hydroxyl-Functionalized Polymers with Isocyanates" Macromolecules, 44:4828-4835 (2011).

Bilan et al. "Quantum Dot-Based Nanotools for Bioimaging, Diagnostics, and Drug Delivery" ChemBioChem, 17:2103-2114 (2013).

Boyer et al. "Bioapplications of RAFT Polymerization" Chemical Reviews, 109:5402-5436 (2009).

Boyer et al. "Direct Synthesis of Well-Defined Heterotelechelic Polymers for Bioconjugations" Macromolecules, 41:5641-5650 (2008).

Broyer et al. "Emerging Synthetic Techniques for Protein-Polymer Conjugations" ChemComm, 47:2212-2226 (2011).

Chen et al. "Thiocarbonylthio End Group Removal from RAFT-Synthesized Polymers by a Radical-Induced Process" Journal of Polymer Science: Part A: Polymer Chemistry, 47:6704-6714 (2009).

Cheng et al. "Near Infrared Receptor-Targeted Nanoprobes for Early Diagnosis of Cancers" Current Medicinal Chemistry, 19:4767-4785 (2012).

(56) References Cited

OTHER PUBLICATIONS

Chiefari et al. "Living Free-Radical Polymerization by Reversible Addition-Fragmentation Chain Transfer: The RAFT Process" Macromolecules, 31:5559-5562 (1998).
Chitgupi et al. "Naphthalocyanines as contrast agents for photoacoustic and multimodal imaging" Biomedical Engineering Letters, 8:215-221 (2018).
Chong et al. "Thiocarbonylthio Compounds [S C(Ph)S-R] in Free Radical Polymerization with Reversible Addition-Fragmentation Chain Transfer (RAFT Polymerization). Role of the Free-Radical Leaving Group (R)" Macromolecules, 36:2256-2272 (2003).
Cox et al. "Quantitative spectroscopic photoacoustic imaging: a review" Journal of Biomedical Optics, 17(6):061202-1-061202-22 (2012).
Daimon et al. "Glass Transition Behaviors of Random and Block Copolymers and Polymer Blends of Styrene and Cyclododecyl Acrylate. I. Glass Transition Temperatures" Polymer Journal, 7(4):460-466 (1975).
De La Zerda et al. "Advanced contrast nanoagents for photoacoustic molecular imaging, cytometry, blood test and photothermal theranostics" Contrast Media & Molecular Imaging, 6(5):346-369 (2011).
De Silva et al. "Signaling Recognition Events with Fluorescent Sensors and Switches" Chemical Reviews, 97:1515-1566 (1997).
Duffy et al. "Towards optimized naphthalocyanines as sonochromes for photoacoustic imaging in vivo" Photoacoustics, 9:49-61 (2018).
Dujols et al. "A Long-Wavelength Fluorescent Chemodosimeter Selective for Cu(II) Ion in Water" Journal of the American Chemical Society, 119:7386-7387 (1997).
Evans et al. "Functional and Tuneable Amino Acid Polymers Prepared by RAFT Polymerization" Journal of Polymer Science Part A: Polymer Chemistry, 47:6814-6826 (2009).
Gondi et al. "Versatile Pathway to Functional Telechelics via RAFT Polymerization and Click Chemistry" Macromolecules, 40:474-481 (2007).
Grover et al. "Protein-Polymer Conjugates: Synthetic Approaches by Controlled Radical Polymerizations & Interesting Applications" Current Opinion in Chemical Biology, 14(6):818-827 (2010).
Gujraty et al. "Synthesis of Homopolymers and Copolymers Containing an Active Ester of Acrylic Acid by RAFT: Scaffolds for Controlling Polyvalent Ligand Display" Journal of Polymer Science Part A: Polymer Chemistry, 46(21):7246-7257 (2008).
Guo et al. "Facile and Efficient Synthesis of Fluorescence-Labeled RAFT Agents and Their Application in the Preparation of α-, ω- and α, ω-End-Fluorescence-Labeled Polymers" Macromolecular Chemistry and Physics, 213:1851-1862 (2012).
Haddleton et al. "Monohydroxy terminally functionalised poly(methyl methacrylate) from atom transfer radical polymerisation" ChemComm, 7:683-684 (1997).
Haddleton et al. "Phenolic Ester-Based Initiators for Transition Metal Mediated Living Polymerization" Macromolecules, 32:8732-8739 (1999).
Haisch, Christoph "Quantitative analysis in medicine using photoacoustic tomography" Analytical and Bioanalytical Chemistry, 393:473-479 (2009).
Haridharan et al. "Exploration of Novel Pyrene Labeled Amphiphilic Block Copolymers: Synthesis Via ATRP, Characterization and Properties" Journal of Macromolecular Science, Part A: Pure and Applied Chemistry, 47:918-926 (2010).
Heredia et al. "Synthesis of Heterotelechelic Polymers for Conjugation of Two Different Proteins" Macromolecules, 42:2360-2367 (2009).
Hildebrand et al. "Modulating the solubility of zwitterionic poly((3-methacrylamidopropyl)ammonioalkane sulfonate)s in water and aqueous salt solutions via the spacer group separating the cationic and the anionic moieties" Polym. Chem., 7:731-740 (2016).
Hong et al. "Direct Synthesis of Biotinylated Stimuli-Responsive Polymer and Diblock Copolymer by RAFT Polymerization Using Biotinylated Trithiocarbonate as RAFT Agent" Macromolecules, 39:3517-3524 (2006).
Hu et al. "Panchromatic Chromophore-Tetrapyrrole Light-Harvesting Arrays Constructed from Bodipy, Perylene, Terrylene, Porphyrin, Chlorin, and Bacteriochlorin Building Blocks" New Journal of Chemistry, 40:8032-8052 (2016).
Jiang et al. "One-side non-covalent modification of CVD graphene sheet using pyrene-terminated PNIPAAm generated via RAFT polymerization for the fabrication of thermo-responsive actuators" Sensors and Actuators B: Chemical, 239:193-202 (2017).
Jung et al. "Chemical Strategies for the Synthesis of Protein-Polymer Conjugates" Advances in Polymer Science, 253:37-70 (2013).
Kamigaito et al. "Metal-Catalyzed Living Radical Polymerization" Chemical Reviews, 101:3689-3745 (2001).
Kim et al. "Thermally controlled wettability of a nanoporous membrane grafted with catechol-tethered poly(N-isopropylacrylamide)" ChemComm, 48:9227-9229 (2012).
Kwon et al. "A Highly Selective Fluorescent Chemosensor for Pb2+" Journal of the American Chemical Society, 127:10107-10111 (2005).
Larrabee et al. "Radiation-Induced Polymerization of Sodium 10-Undecenoate in Aqueous Micelle Solutions" Journal of Polymer Science: Polymer Letters Edition, 17:749-751 (1979).
Li et al. "Conjugation of RAFT-generated polymers to proteins by two consecutive thiol-ene reactions" Polymer Chemistry, 1:854-859 (2010).
Li et al. "Crosslinked dendronized polyols as a general approach to brighter and more stable fluorophores" ChemComm, 52:3781-3784 (2016).
Li et al. "Synthesis and characterization of a naphthalimide-dye end-labeled copolymer by reversible addition-fragmentation chain transfer (RAFT) polymerization" Canadian Journal of Chemistry, 89:317-325 (2011).
Li et al. "Synthesis and pH-responsive self-assembly behavior of a fluorescent amphiphilic triblock copolymer mPEG-b-PCL-b-PDMAEMA-g-PC for the controlled intracellular delivery of doxorubicin" RSC Advances, 6:27102-27112 (2016).
Li et al. "The Thiol-Isocyanate Click Reaction: Facile and Quantitative Access to ω-End-Functional Poly(N,N-diethylacrylamide) Synthesized by RAFT Radical Polymerization" Macromolecules, 42:6537-6542 (2009).
Liras et al. "Transformation of the Bromine End Group into Thiol in (Meth)acrylic Polymers Synthesized by Atom Transfer Radical Polymerization" Macromolecules, 44:1335-1339 (2011).
Liu et al. "Single-Polymer-Single-Cargo Strategy Packages Hydrophobic Fluorophores in Aqueous Solution with Retention of Inherent Brightness" ACS Macro Letters, 8:79-83 (2019).
Liu et al. "Strategies for chemical modification of graphene and applications of chemically modified graphene" Journal of Materials Chemistry, 22:12435-12452 (2012).
Liu et al. "Thermosensitive Graphene Nanocomposites Formed Using Pyrene-Terminal Polymers Made by RAFT Polymerization" Journal of Polymer Science Part A: Polymer Chemistry, 48:425-433 (2010).
Madsen et al. "Synthesis of Rhodamine 6G-Based Compounds for the ATRP Synthesis of Fluorescently Labeled Biocompatible Polymers" Biomacromolecules, 12:2225-2234 (2011).
Malz et al. "Synthesis of functional polymers by atom transfer radical polymerization" Macromolecular Chemistry and Physics, 200:642-651 (1999).
Mets et al. "Submillisecond Detection of Single Rhodamine Molecules in Water" Journal of Fluorescence, 4(3):259-264 (1994).
Moad et al. "Advances in RAFT polymerization: the synthesis of polymers with defined end-groups" Polymer, 46:8458-8468 (2005).
Moad et al. "Functional polymers for optoelectronic applications by RAFT polymerization" Polymer Chemistry, 2:492-519 (2011).
Moerner et al. "Optical Spectroscopy of Single Impurity Molecules in Solids" Angewandte Chemie, 32(4):457-628 (1993).
Moraes et al. "Influence of Block versus Random Monomer Distribution on the Cellular Uptake of Hydrophilic Copolymers" ACS Macro Letters, 5:1416-1420 (2016).
Morishima et al. "Anomalous Behavior of Triplet-Excited Zinc(II) Tetraphenylporphyrin Moieties Compartmentalized in the Hydro-

(56) References Cited

OTHER PUBLICATIONS phobic Cluster of Pendant Cyclododecyl Groups in an Amphiphilic Polyelectrolyte" Chemistry Letters, pp. 583-586 (1994).
Morishima et al. "Characterization of Unimolecular Micelles of Random Copolymers of Sodium 2-(Acrylamido)-2-methylpropanesulfonate and Methacrylamides Bearing Bulky Hydrophobic Substituents" Macromolecules, 28:2874-2881 (1995).
Morishima et al. "Long-Lived Porphyrin Cation Radicals Protected in Unimer Micelles of Hydrophobically-Modified Polyelectrolytes" Macromolecules, 29:6505-6509 (1996).
Orrit et al. "Single Pentacene Molecules Detected by Fluorescence Excitation in a p-Terphenyl Crystal" Physical Review Letters, 65(21):2716-2719 (1990).
Patton et al. "A Versatile Synthetic Route to Macromonomers via Polymerization" Macromolecules, 39:8674-8683 (2006).
Pirani et al. "Protein surface labeling reactivity of N-hydroxysuccinimide esters conjugated to Fe3O4@SiO2 magnetic nanoparticles" Journal of Nanoparticle Research, 17(355):1-11 (2015).
Postma et al. "Synthesis of Well-Defined Polystyrene with Primary Amine End Groups through the Use of Phthalimido-Functional RAFT Agents" Macromolecules, 39:5293-5306 (2006).
Prazeres et al. "Determination of the critical micelle concentration of surfactants and amphiphilic block copolymers using coumarin 153" Inorganica Chimica Acta, 381:181-187 (2012).
Prazeres et al. "RAFT polymerization and self-assembly of thermoresponsive poly(N-decylacrylamide-b-N,N-diethylacrylamide) block copolymers bearing a phenanthrene fluorescent a-end group" Polymer, 51:355-367 (2010).
Quang et al. "Fluoro- and Chromogenic Chemodosimeters for Heavy Metal Ion Detection in Solution and Biospecimens" Chemical Reviews, 110:6280-6301 (2010).
Rathfon et al. "Fluorimetric Nerve Gas Sensing Based on Pyrene Imines Incorporated into Films and Sub-Micrometer Fibers" Advanced Functional Materials, 19:689-695 (2009).
Robin et al. "Fluorescent Block Copolymer Micelles That Can Self-Report on Their Assembly and Small Molecule Encapsulation" Macromolecules, 49:653-662 (2016).
Roth et al. "RAFT Polymerization and Thiol Chemistry: A Complementary Pairing for Implementing Modern Macromolecular Design" Macromolecular Rapid Communications, 32:1123-1143 (2011).
Roth et al. "Synthesis of Heterotelechelic α,ω Dye-Functionalized Polymer by the RAFT Process and Energy Transfer between the End Groups" Macromolecules, 43:895-902 (2010).
Roth et al. "Synthesis of Reactive Telechelic Polymers Based on Pentafluorophenyl Esters" Macromolecules, 41:8513-8519 (2008).
Scales et al. "Fluorescent Labeling of RAFT-Generated Poly(N-isopropylacrylamide) via a Facile Maleimide-Thiol Coupling Reaction" Biomacromolecules, 7:1389-1392 (2006).
Shen et al. "Synthesis of methacrylate macromonomers using silica gel supported atom transfer radical polymerization" Macromolecular Chemistry and Physics, 201:1387-1394 (2000).
Sreejith et al. "Near-Infrared Squaraine Dye Encapsulated Micelles for in Vivo Fluorescence and Photoacoustic Bimodal Imaging" ACS Nano, 9(6):5695-5704 (2015).
Sumerlin et al. "Water-Soluble Polymers. 84. Controlled Polymerization in Aqueous Media of Anionic Acrylamido Monomers via RAFT" Macromolecules, 34:6561-6564 (2001).
Sun et al. "Crosslinked polymer nanocapsules" Polymer International, 65:351-361 (2016).
Terashima et al. "Synthesis and Single-Chain Folding of Amphiphilic Random Copolymers in Water" Macromolecules, 47:589-600 (2014).
Umemura et al. "Recent advances in sonodynamic approach to cancer therapy" Ultrasonics Sonochemistry, 3:S187-S191 (1996).
Vandewalle et al. "Macromolecular Coupling in Seconds of Triazolinedione End-Functionalized Polymers Prepared by RAFT Polymerization" ACS Macro Letters, 5:766-771 (2016).
Willcock et al. "End group removal and modification of RAFT polymers" Polymer Chemistry, 1:149-157 (2010).
Wolff et al. "Detection of Thermoresponsive Polymer Phase Transition in Dilute Low-Volume Format by Microscale Thermophoretic Depletion" Analytical Chemistry, 86:6797-6803 (2014).
Yang et al. "A Rhodamine-Based Fluorescent and Colorimetric Chemodosimeter for the Rapid Detection of Hg2+ Ions in Aqueous Media" Journal of the American Chemical Society, 127:16760-16761 (2005).
Yeung, Edward S. "Chemical Analysis of Single Human Erythrocytes" Accounts of Chemical Research, 27:409-414 (1994).
York et al. "Facile Synthetic Procedure for omega, Primary Amine Functionalization Directly in Water for Subsequent Fluorescent Labeling and Potential Bioconjugation of RAFT-Synthesized (Co)Polymers" Biomacromolecules, 8(8):2337-2341 (2007).
Yumita et al. "Sonodynamically induced antitumor effect of gallium-porphyrin complex by focused ultrasound on experimental kidney tumor" Cancer Letters, 112:79-86 (1997).
Yumita et al. "The Combination Treatment of Ultrasound and Antitumor Drugs on Yoshida Sarcoma" Japanese Journal of Hyperthermic Oncology, 3(2):175-182 (1987).
Zeng et al. "Synthesis and Charaterization of Comb-Branched Polyeletrolytes. 1. Preparation of Cationic macromonomer of 2-(Dimethylamino)ethyl Methacrylate by Atom Transfer Radical Polymerization" Macromolecules, 33:1628-1635 (2000).
Zhang et al. "End-Functional Poly(tert-butyl acrylate) Star Polymers by Controlled Radical Polymerization" Macromolecules, 33:2340-2345 (2000).
Zhang et al. "Facile Synthesis of Multivalent Water-Soluble Organic Nanoparticles via 'Surface Clicking' Alkynylated Surfactant Micelles" Macromolecules, 43:4020-4022 (2010).
Zhang et al. "Synthesis of Functional Polystyrenes by Atom Transfer Radical Polymerization Using Protected and Unprotected Carboxylic Acid Initiators" Macromolecules, 32:7349-7353 (1999).
Zhang et al. "Bioconjugatable, PEGylated Hydroporphyrins for Photochemistry and Photomedicine. Narrow-Band, Near-Infrared Emitting Bacteriochlorins" New Journal of Chemistry, 40(9):7750-7767 (2016).
Zhang et al. "Synthesis of diverse α,ω-telechelic polystyrenes with di- and tri-functionality via tandem or one-pot strategies combining aminolysis of RAFT-polystyrene and a thiol-ene "click" reaction" RSC Advances, 5(55):44571-44577 (2015).
Zheng et al. "Synthesis and Characterization of Dendrimer-Star Polymer Using Dithiobenzoate-Terminated Poly (propylene imine) Dendrimer via Reversible Addition-Fragmentation Transfer Polymerization" Macromolecules, 38:6841-6848 (2005).
Lindenburg et al. "MagFRET: The First Genetically Encoded Fluorescent Mg2+ Sensor" PLoS One, 8(12):e82009 (2013).
Miksa, "Fluorescent Dyes Used in Polymer Carriers as Imaging Agents in Anticancer Therapy," Medicinal Chemistry, 6:611-639, (2016).
International Search Report and the Written Opinion of the International Searching Authority corresponding to International Patent Application No. PCT/US2018/66195 (10 pages) (mailed May 6, 2019).
International Search Report and the Written Opinion of the International Searching Authority corresponding to International Patent Application No. PCT/US2019/54008 (9 pages) (mailed Mar. 24, 2020).
Morishima et al. "Characterization of Unimolecular Micelles of Random Copolymers of Sodium 2-(Acrylamido)-2-methylpropanesulfonate and Methacrylamides Bearing Bulky Hydrophobic Substituents," Macromolecules, 28(8):2874-2881, (1995).
Demidova et al. "Photodynamic Therapy Targeted to Pathogens" International Journal of Immunopathology and Pharmacology, 17(3):245-254 (2004).
Extended European Search Report corresponding to European Patent Application No. 19871166.5 (11 pages) (dated Jul. 14, 2022).
Goodwin et al. "Single-Molecule Detection in Liquids by Laser-Induced Fluorescence" Accounts of Chemical Research, 29:607-613 (1996).
Liu et al. "Self-assembly with fluorescence readout in a free base dipyrrin-polymer triggered by metal ion binding in aqueous solution" New Journal of Chemistry, 43:9711-9724 (2019).

(56) References Cited

OTHER PUBLICATIONS

Mizusaki et al. "An assessment by fluorescence spectroscopy of the stability of polyanions/positively charged liposome systems in the presence of polycations" Polymer, 42:5615-5624 (2001).

Mizusaki et al. "Interaction of a pyrene-labeled cholesterol-bearing polyanion with surfactant micelles studied by fluorescence quenching" Polymer, 43:5865-5871 (2002).

Mizusaki et al. "Interaction of Pyrene-Labeled Hydrophobically Modified Polyelectrolytes with Oppositely Charged Mixed Micelles Studied by Fluorescence Quenching" The Journal of Physical Chemistry B, 102:1980-1915 (1998).

Morishima et al. "Anomalously Blue-Shifted Fluorescence and Phosphorescence of Zinc(II) Tetraphenylporphyrin in Highly Constraining Microenvironments in Hydrophobically Modified Polysulfonates" Macromolecules, 28:1203-1207 (1995).

Morishima et al. "Photophysical Behavior of Zinc(II) Tetraphenylporphyrin in Highly Constraining Microenvironments. Anomalously Long-Lived Excited-Triplet in the Hydrophobic Clusters of Amphiphilic Polysulfonates" J. Phys. Chem, 99:4512-17 (1995).

Tang et al. "A New Rhodamine B-coumarin Fluorochrome for Colorimetric Recognition of Cu2+ and Fluorescent Recognition of Fe3+ in Aqueous Media" Bulletin of the Korean Chemical Society, 32(9):3400-3404 (2011).

Van Der Meer, B. W. "Kappa-squared: from nuisance to new sense" Reviews in Molecular Biotechnology, 82:181-196 (2002).

Zenkevich et al. "Spectroscopic and photophysical properties of covalent ether-bonded porphyrin-chlorin heterodimers" Journal of Luminescence, 75(3):229-244 (1997) (Abstract only).

Extended European Search Report corresponding to European Patent Application No. 18890479.1 (9 pages) (dated Nov. 10, 2021).

Schaberle et al. "Ultrafast Dynamics of Manganese(III), Manganese(II), and Free-Base Bacteriochlorin: Is There Time for Photochemistry?" Inorg. Chem. 2017 56(5):2677-2689 (Feb. 16, 2017).

* cited by examiner

POLYMERIC FLUOROPHORES, COMPOSITIONS COMPRISING THE SAME, AND METHODS OF PREPARING AND USING THE SAME

RELATED APPLICATION INFORMATION

This application claims the benefit of U.S. Provisional Patent Application Ser. No. 62/609,494, filed Dec. 22, 2017, and U.S. Provisional Patent Application Ser. No. 62/714,541, filed Aug. 3, 2018, the disclosures of each of which are incorporated herein by reference in their entirety.

STATEMENT OF GOVERNMENT SUPPORT

This invention was made with government support under grant number DE-SC0001035 awarded by the Department of Energy. The government has certain rights to this invention.

FIELD

The present invention relates generally to polymeric fluorophores including a dye, a polymer segment, and optionally a bioconjugate group. The present invention also relates to compositions comprising the polymeric fluorophores and methods of preparing and using the same.

BACKGROUND

Many applications of fluorophores take place in aqueous solution yet most organic fluorophores are hydrophobic or only modestly polar. Numerous approaches abound for encapsulating fluorophores yet none have satisfied the criteria of synthetic simplicity, absence of fluorophore-fluorophore quenching, and presence of a single bioconjugatable group.

SUMMARY

A first aspect of the present invention is directed to a compound having a structure represented by:

A-B-C, or

C-A-B wherein

A is a dye (e.g., a fluorophore), optionally wherein the dye has a molecular weight in a range of about 150 Daltons (Da) to about 3,000 Da;

B is a polymer comprising one or more hydrophobic unit(s) and one or more hydrophilic unit(s), optionally wherein the polymer has a molecular weight in a range of about 1,000 Da, 5,000 Da, or 10,000 Da to about 175,000 Da; and optionally C, wherein C comprises a bioconjugate group.

Another aspect of the present invention is directed to a composition comprising a compound of the present invention and optionally water. Also, aspects of the present invention are directed to a composition comprising: a particle (e.g., a particle including a core and a shell), wherein the particle comprises a compound having a structure represented by:

A-B-C, or

C-A-B wherein

A is a dye (e.g., a fluorophore);

B is a polymer comprising one or more hydrophobic unit(s) and one or more hydrophilic unit(s); and optionally C, wherein C comprises a bioconjugate group; and water.

A further aspect of the present invention is directed to a method of preparing a compound comprising: polymerizing a hydrophobic monomer and a hydrophilic monomer to provide a co-polymer; attaching a dye to a first portion (e.g., a terminal or end portion) of the co-polymer, thereby providing the compound; optionally attaching a bioconjugate group to a second portion (e.g., the other terminal or end portion) of the co-polymer; and/or optionally cross-linking the compound. Polymerizing the hydrophobic monomer and the hydrophilic monomer may comprise polymerizing via a living radical polymerization in the presence of an initiator (e.g., a bromide initiator), a catalyst (e.g., a ruthenium catalyst), and optionally a co-catalyst to provide the co-polymer.

Another aspect of the present invention is directed to a compound prepared according to a method of the present invention.

Also provided according to embodiments of the present invention is use of a compound of the present invention and/or use of a composition of the present invention, such as, for example, use in flow cytometry.

A further aspect of the present invention is directed to a method of detecting cells and/or particles using flow cytometry, the method comprising labeling cells and/or particles with a compound of the present invention; and detecting the compound by flow cytometry, thereby detecting the cells and/or particles.

Another aspect of the present invention is directed to a method of detecting a tissue and/or agent (e.g., a cell, infecting agent, etc.) in a subject, the method comprising: administering to the subject a compound of the present invention or a composition of the present invention, optionally wherein the compound associates with the tissue and/or agent; and detecting the compound within the subject, thereby detecting the tissue and/or agent.

A further aspect of the present invention is directed to a biomolecule (e.g., a cell, antibody, etc.) comprising one or more (e.g., 1, 2, 3, 4, 5, 6, or more) compound(s) of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

Figure 1:
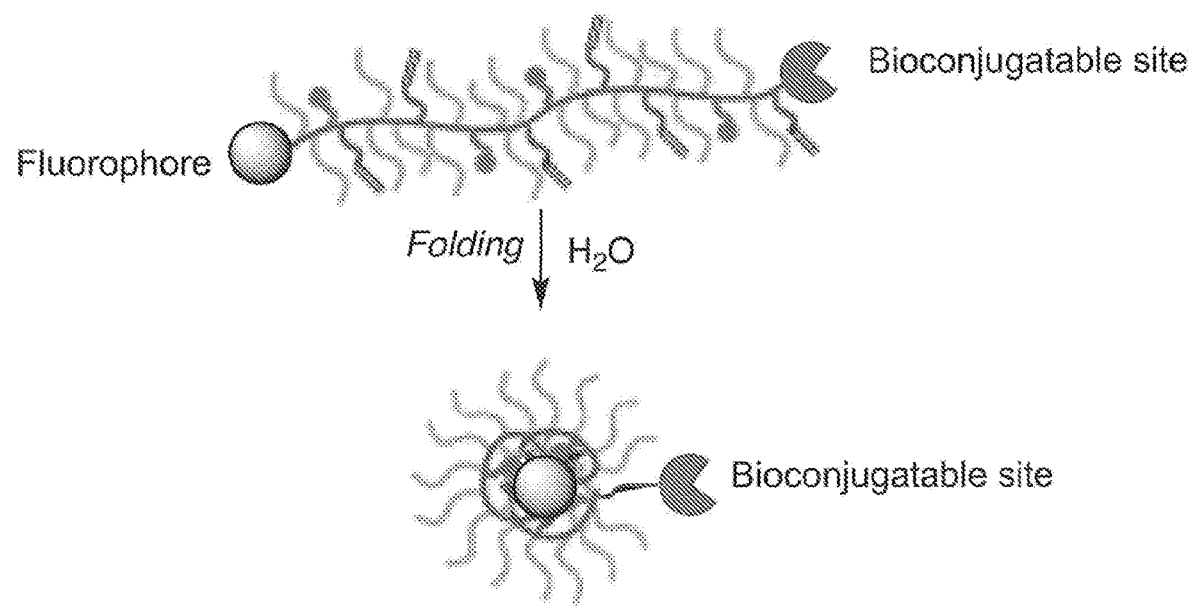
FIG. 1 shows a schematic of an exemplary polymeric fluorophore according to embodiments of the present invention.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

It will also be understood that, as used herein, the terms "example," "exemplary," and grammatical variations thereof are intended to refer to non-limiting examples and/or variant embodiments discussed herein, and are not intended to indicate preference for one or more embodiments discussed herein compared to one or more other embodiments.

The term "about," as used herein when referring to a measurable value such as an amount or concentration and the like, is meant to encompass variations of ±10%, ±5%, 1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

"Derivative", when used herein in reference to a chemical molecule, refers to a chemical molecule with one or more atoms (e.g., hydrogen), functional groups, and/or bonds modified (e.g., removed, substituted, etc.) compared to the parent molecular entity. For example, a derivative of a dye may refer to the parent dye compound that has one or more atoms (e.g., hydrogen) and/or functional groups modified (e.g., removed) to facilitate covalent binding to another group or moiety (e.g., to facilitate covalent binding to a polymer). In some embodiments, a derivative may include a functional group (e.g., a substituent and/or auxochrome) that alters the absorption spectrum of the parent molecular entity.

"Alkyl" as used herein alone or as part of another group, refers to a straight or branched chain hydrocarbon containing from 1 to 20 carbon atoms, which can be referred to as a C1-C20 alkyl. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, and, in some embodiments, refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 20 carbon atoms (or in loweralkenyl 1 to 4 carbon atoms) that can include 1 to 8 double bonds in the normal chain, and can be referred to as a C1-C20 alkenyl. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 20 carbon atoms (or in loweralkynyl 1 to 4 carbon atoms) which include 1 triple bond in the normal chain, and can be referred to as a C1-C20 alkynyl. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Halo" as used herein refers to any suitable halogen, including —F, —Cl, —Br, and —I.

"Mercapto" as used herein refers to an —SH group.
"Azido" as used herein refers to an —$N_3$ group.
"Cyano" as used herein refers to a —CN group.
"Hydroxyl" as used herein refers to an —OH group.
"Nitro" as used herein refers to an —$NO_2$ group.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, but are not limited to, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.
"Alkylamino" as used herein alone or as part of another group means the radical —NHR, where R is an alkyl group.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.
"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a salt (e.g., a sodium (Na) salt) of a sulfonic acid and/or a compound of the formula —S(O)(O)OR, where R is any suitable substituent such as alkyl, cycloalkyl, alkenyl, alkynyl or aryl.

"Sulfonic acid as used herein refers to a compound of the formula —S(O)(O)OH.

"Amide" as used herein alone or as part of another group refers to a —C(O)N$R_a R_b$ radical, where $R_a$ and $R_b$ are any suitable substituent such as alkyl, cycloalkyl, alkenyl, alkynyl or aryl.

"Sulfonamide" as used herein alone or as part of another group refers to a —S(O)$_2$N$R_a R_b$ radical, where $R_a$ and $R_b$ are any suitable substituent such as H, alkyl, cycloalkyl, alkenyl, alkynyl, aryl, heteroalkyl, or heteroaryl.

Compounds of the present invention include polymeric fluorophores. Compounds of the present invention include a single (i.e., 1) polymer that is attached to a single (i.e., 1) dye, and optionally include a single (i.e., 1) bioconjugate group, which may have a single binding site for a biomolecule. An exemplary compound is shown in FIG. 1. In some embodiments, the one polymer is attached to both the dye and the bioconjugate group (when present). In some embodiments, the one dye is attached to both the polymer and the bioconjugate group (when present). In some embodiments, a composition of the present invention comprises a compound of the present invention in a solution such as, e.g., water, an aqueous solution, and/or a hydrophobic solvent.

While a compound of the present invention may be attached to a single biomolecule via the bioconjugate group, the biomolecule may comprise one or more (e.g., 1, 2, 3, 4, 5, 6, 7, 8, 9, 10, or more) compound(s) of the present invention. Thus, in some embodiments, a biomolecule and/or portion thereof comprises one or more (e.g., 1, 2, 3, 4, 5, 6, 7, 8, 9, 10, or more) compound(s) of the present invention.

In some embodiments, a compound of the present invention has a structure represented by:

A-B-C, or

C-A-B wherein

A is a dye (e.g., a fluorophore);

B is a polymer comprising one or more hydrophobic unit(s) and one or more hydrophilic unit(s); and optionally C, wherein C, when present, comprises a bioconjugate group.

"Dye" and "fluorophore" are used interchangeably herein to refer to a molecular entity that emits fluorescence. A dye or fluorophore can also be referred to as a chromophore having certain spectroscopic features and/or properties. In some embodiments, the dye has a molecular weight in a range of about 150 Daltons (Da) to about 3,000 Da, about 400 Da to about 1100 Da, or about 300 Da to about 1,000 Da. In some embodiments, the dye has a molecular weight of about 150, 200, 300, 400, 500, 600, 700, 800, 900, 1000, 1200, 1300, 1400, 1500, 1600, 1700, 1800, 1900, 2000, 2200, 2300, 2400, 2500, 2600, 2700, 2800, 2900, or 3000 Da. Exemplary dyes include, but are not limited to, tetrapyrroles; rylenes such as perylene, terrylene, and quarterrylene; fluoresceins such as TET (Tetramethyl fluorescein), 2',7'-dimethoxy-4',5'-dichloro-6-carboxyfluorescein (JOE), 6-carboxyfluorescein (HEX) and 5-carboxyfluorescein (5-FAM); phycoerythrins; resorufin dyes; coumarin dyes; rhodamine dyes such as 6-carboxy-X-rhodamine (ROX), Texas Red, and N,N,N',N'-tetramethyl-6-carboxyrhodamine (TAMRA); cyanine dyes; phthalocyanines; boron-dipyrromethene (BODIPY) dyes; quinolines; pyrenes; acridine; stilbene; as well as derivatives thereof. In some embodiments, the dye is a tetrapyrrole, which includes porphyrins, chlorins, and bacteriochlorins, and derivatives thereof. Exemplary tetrapyrroles include but are not limited to those described in U.S. Pat. Nos. 6,272,038; 6,451,942; 6,420,648; 6,559,374; 6,765,092; 6,407,330; 6,642,376; 6,946,552; 6,603,070; 6,849,730; 7,005,237; 6,916,982; 6,944,047; 7,884,280; 7,332,599; 7,148,361; 7,022,862; 6,924,375; 7,501,507; 7,323,561; 7,153,975; 7,317,108; 7,501,508; 7,378,520; 7,534,807; 7,919,770; 7,799,910; 7,582,751; 8,097,609; 8,187,824; 8,207,329; 7,633,007; 7,745,618; 7,994,312; 8,278,340; 9,303,165; and 9,365,722; and International Application Nos. PCT/US17/47266 and PCT/US17/63251. In some embodiments, the dye is hydrophobic. In some embodiments, the dye may be attached and/or bound to a monomer that is polymerized with one or more different monomers (e.g., polymerized with a hydrophobic monomer and/or hydrophilic monomer). In some embodiments, the dye is a luminophore (i.e., a material and/or compound that can emit light and does not specify the nature of the originating state (e.g., singlet, triplet, and/or another state)). Exemplary luminophores include, but are not limited to, phosphors and/or fluorophores, which afford phosphorescence and/or fluorescence, respectively.

The polymer of a compound of the present invention may comprise one or more (e.g., 1, 5, 10, 50, 100, or more) hydrophobic unit(s) and one or more (e.g., 1, 5, 10, 50, 100, or more) hydrophilic unit(s). The polymer may be prepared from one or more (e.g., 1, 5, 10, 50, 100, or more) hydrophobic monomer(s) and one or more (e.g., 1, 5, 10, 50, 100, or more) hydrophilic monomer(s) using any type of polymerization to provide the polymer comprising the one or more hydrophobic unit(s) and the one or more hydrophilic unit(s). In some embodiments, the polymer may be prepared from two or more (e.g., 2, 3, 4, 5, or more) hydrophobic monomers that are different from each other and/or two or more (e.g., 2, 3, 4, 5, or more) hydrophilic monomers that are different from each other. For example, in some embodiments, a polymer of a compound of the present invention may be prepared from at least one hydrophobic monomer, at least one of a first hydrophilic monomer, and at least one of a second hydrophilic monomer, wherein the first hydrophilic monomer and the second hydrophilic monomer are different from each other.

A "hydrophilic monomer" as used herein refers to a monomer that comprises a hydrophilic (e.g., ionic and/or polar) functional group (e.g., a hydrophilic pendant functional group), optionally wherein the hydrophilic functional group is at a terminal portion of a moiety and/or monomer. As one of skill in the art would understand, a portion of a hydrophilic monomer may be hydrophobic such as, e.g., the portion that forms a polymer backbone when polymerized with other monomers and/or the portion (e.g., hydrocarbon chain) of a functional group including an ionic moiety, but is still referred to as a hydrophilic monomer if it comprises a hydrophilic functional group. A "hydrophilic unit" as used herein refers to the section or unit of a polymer prepared from a respective hydrophilic monomer. A "hydrophobic monomer" as used herein refers to a monomer that comprises a hydrophobic functional group (e.g., a hydrophobic pendant functional group), optionally wherein the hydrophobic functional group is at a terminal portion of a moiety and/or monomer. In some embodiments, the hydrophobic functional group is a hydrocarbon moiety (e.g., an alkyl). A "hydrophobic unit" as used herein refers to the section or unit of a polymer prepared from a respective hydrophobic monomer.

In some embodiments, the polymer of a compound of the present invention may also be referred to as the polymer segment of a compound of the present invention. The one or more hydrophobic unit(s) and the one or more hydrophilic unit(s) may be randomly distributed in the polymer. In some embodiments, the polymer is a random copolymer. The polymer may be an amphiphilic random co-polymer, optionally a linear amphiphilic random co-polymer. The one or more hydrophobic unit(s) and the one or more hydrophilic unit(s) may be present in the polymer in a ratio of about 1:1, 1:2, 1:3, 1:4, 1:5, 1:6, 1:7, 1:8, 1:9, or 1:10 (hydrophobic units:hydrophilic units). The length of the polymer may be varied and/or controlled. In some embodiments, the polymer has a molecular weight in a range of about 1,000 Da to about 175,000 Da, about 5,000 Da to about 175,000 Da, about 10,000 Da to about 175,000 Da, about 100,000 Da to about 150,000 Da, about 50,000 Da to about 130,000 Da, or about 10,000 Da to about 100,000 Da. In some embodiments, the polymer has a molecular weight of about 1, 2, 3, 4, 5, 6, 7, 8, 9, 10, 20, 30, 40, 50, 60, 70, 80, 90, 100, 110, 120, 130, 140, 150, 160, or 170 kiloDaltons (kDa).

A hydrophobic unit and/or a hydrophilic unit of the polymer may comprise a pendant functional group. A "pendant functional group" may be a functional group directly attached to the polymer backbone or directly attached to a moiety attached to the polymer backbone. A pendant functional group may be part of the hydrophobic unit and/or monomer and/or hydrophilic unit and/or monomer at the time of polymerization or may be added to the hydrophobic unit and/or hydrophilic unit after polymerization. In some embodiments, a pendant functional group may be added to a hydrophobic unit and/or hydrophilic unit after polymerization (e.g., post-polymerization functionalization). In some embodiments, a pendant functional group comprises a charged group. In some embodiments, a pendant functional group is a halo, hydroxyl, carboxyl, amino, formyl, vinyl, epoxy, mercapto, ester (e.g., an active ester such as a pentafluorophenyl ester, succinimido ester, 2,4-dinitrophenyl ester, etc.), azido, pentafluorophenyl, succinimido, fluorophenyl, maleimido, isocyanato, or isothiocyanato group.

In some embodiments, the pendant functional group is a hydrophilic group comprising a terminal cationic (e.g., ammonium), anionic (e.g., sulfonate, phosphate, carboxylate), or zwitterionic (e.g., a choline or choline-like group (e.g., a derivative of a choline)) group and optionally a poly(ethylene glycol) moiety and/or unit. In some embodiments, the hydrophilic group is attached to the poly(ethylene glycol) moiety and/or unit, optionally attached to a terminal portion of the poly(ethylene glycol) moiety and/or unit.

In some embodiments, a hydrophobic unit comprises a pendant functional group comprising an alkyl (e.g., dodecyl methyl) and/or a hydrophilic unit comprises a pendant functional group comprising a glycol (e.g., poly(ethylene glycol)), sulfonic acid, and/or a sulfonate. In some embodiments, the hydrophobic unit is prepared from an alkyl acrylate (e.g., dodecyl methyl acrylate) monomer and/or the hydrophilic unit is prepared from a glycol acrylate (e.g., PEGylated methyl acrylate) monomer. In some embodiments, a compound of the present invention comprises at least one hydrophobic unit prepared from an alkyl acrylate (e.g., dodecyl methyl acrylate) monomer and at least two different hydrophilic units, which include a first hydrophilic unit prepared from a glycol acrylate (e.g., PEGylated methyl acrylate) monomer and a second hydrophilic unit prepared from a sulfonic acid acrylate monomer (e.g., 2-acrylamido-2-methylpropane sulfonic acid) and/or a sulfonate acrylate monomer.

In some embodiments, one or more of the hydrophobic unit(s) and/or one or more of the hydrophilic unit(s) may comprise a charge (e.g., a positive or negative charge) and/or a charged group (e.g., a cationic or anionic group), and the charge may suppress non-specific binding to the compound or a portion thereof (e.g., to a portion of the polymer).

In some embodiments, a hydrophobic monomer (which may be used to provide a hydrophobic unit of a polymer as described herein) may have a structure represented by Formula I:

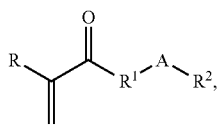

wherein:

R is hydrogen or a C1-C8 alkyl (e.g., a C1, C2, C3, C4, C5, C6, C7, or C8 alkyl);

$R^1$ is absent or is —O—, —NH—, —CH$_2$—;

A is a C1-C20 alkyl, C2-C20 alkenyl, or C2-C20 alkynyl; and $R^2$ is hydrogen or is a halo, hydroxyl, carboxyl, amino, formyl, or ester (e.g., a succinimido ester, 2,4-dinitrophenyl ester, pentafluorophenyl ester, fluorophenyl ester, etc.) group. In some embodiments, $R^2$ in the compound of Formula I is a hydroxyl, carboxyl, amino, formyl, or ester group. In some embodiments, $R^2$ in the compound of Formula I is a hydrogen. In some embodiments, A in the compound of Formula I is a C2-C4 alkyl, a C2-C6 alkyl, a C4-C20 alkyl, a C6-C20 alkyl, a C8-C16 alkyl, a C8-C18 alkyl, a C10-C14 alkyl, or a C10-C12 alkyl. In some embodiments, A in the compound of Formula I is a C2, C3, C4, C5, C6, C7, C8, C9, C10, C1, C12, C13, C14, C15, C16, C17, C18, 19, or C20 alkyl, alkenyl, or alkynyl. In some embodiments, A in the compound of Formula I is a C1, C2, C3, C4, C5, C6, C7, C8, C9, C10, C11, C12, C13, C14, C15, C16, C17, C18,19, or C20 alkyl.

In some embodiments, a hydrophilic monomer (which may be used to provide a hydrophilic unit of a polymer as described herein) may have a structure represented by Formula II:

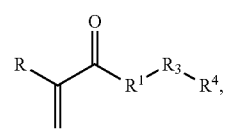

wherein:

R is hydrogen or a C1-C8 alkyl (e.g., a C1, C2, C3, C4, C5, C6, C7, or C8 alkyl);

$R^1$ is absent or is —O—, —NH—, or —CH$_2$—;

$R^3$ is selected from the group consisting of a —(CH$_2$CH$_2$R$^5$)$_n$—, —C$_1$-C$_6$alkyl, —C$_1$-C$_6$alkyl-O—, and —C$_1$-C$_6$alkyl-SO$_3$— or a salt thereof, wherein $R^5$ is —O— or —CH$_2$— and n is an integer from 1 or 5 to 10, 25, 50, 75, 100, 1,000, 5,000, or 10,000; and $R^4$ is absent or is a hydrogen, alkyl, phosphono (e.g., dihydroxyphosphoryl), sulfono (e.g., hydroxysulfonyl), phosphatidyl choline (i.e., 2-(trimethylammonio)ethoxy(hydroxy)phosphoryl), phosphoryl, halo, hydroxyl, carboxyl, amino, ammonio, formyl or ester (e.g., pentafluorophenyl ester, succinimido ester, fluorophenyl ester, or 2,4-dinitrophenyl ester) group.

In some embodiments, R in the compound of Formula II is a hydroxyl, carboxyl, amino, formyl, or ester group, optionally when $R^3$ is —(CH$_2$CH$_2$R$^5$)$_n$—, —C$_1$-C$_6$alkyl, or —C$_1$-C$_6$alkyl-O—. In some embodiments, when $R^3$ in the compound of Formula II is —C$_1$-C$_6$alkyl-O— or —(CH$_2$CH$_2$R$^5$)$_n$— with $R^5$ being —O—, then $R^4$ may be a hydrogen, alkyl (e.g., methyl or ethyl group), phosphono (e.g., dihydroxyphosphoryl), sulfono (e.g., hydroxysulfonyl), phosphatidyl choline, or phosphoryl group. In some embodiments, when $R^3$ in the compound of Formula II is —C$_1$-C$_6$alkyl, then $R^4$ may be a hydroxyl, carboxyl, amino, ammonio, formyl, ester, phosphono, or sulfono group. In some embodiments, when $R^3$ in the compound of Formula II is —C$_1$-C$_6$alkyl-SO$_3$— or a salt thereof, then $R^4$ is hydrogen or is absent. In some embodiments, $R^3$ in the compound of Formula II is a salt (e.g., a sodium salt) of —C$_1$-C$_6$alkyl-SO$_3$— and $R^4$ is absent. In some embodiments, $R^3$ in the compound of Formula II is —(CH$_2$CH$_2$R$^5$)$_n$—.

In some embodiments, a hydrophobic unit may have a structure represented by Formula III:

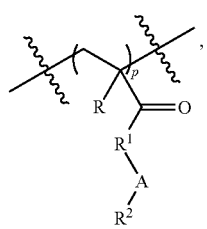

wherein:

R is hydrogen or a C1-C8 alkyl (e.g., a C1, C2, C3, C4, C5, C6, C7, or C8 alkyl);

$R^1$ is absent or is —O—, —NH—, —CH$_2$—;

A is a C1-C20 alkyl, C2-C20 alkenyl, or C2-C20 alkynyl;

$R^2$ is hydrogen or a halo, hydroxyl, carboxyl, amino, formyl, vinyl, epoxy, mercapto, ester (e.g., pentafluorophenyl ester, succinimido ester, fluorophenyl ester, or 2,4-dinitrophenyl ester), azido, maleimido, isocyanato, or isothiocyanato group; and p is an integer from 1 to 10, 100, 1,000, 5,000, 10,000, 50,000, or 100,000.

In some embodiments, R in the compound of Formula III is a hydroxyl, carboxyl, amino, formyl, or ester group. In some embodiments, $R^2$ in the compound of Formula III is a vinyl, epoxy, mercapto, azido, isocyanato, isothiocyanato, or maleimido group, which may optionally be added and/or provided after polymerization and/or by post-polymerization functionalization. In some embodiments, $R^2$ in the compound of Formula III is hydrogen. In some embodiments, A in the compound of Formula III is a C2-C4 alkyl, a C2-C6 alkyl, a C4-C20 alkyl, a C6-C20 alkyl, a C8-C16 alkyl, a C8-C18 alkyl, a C10-C14 alkyl, or a C10-C12 alkyl. In some embodiments, A in the compound of Formula III is a C2, C3, C4, C5, C6, C7, C8, C9, C10, C11, C12, C13, C14, C15, C16, C17, C18, 19, or C20 alkyl, alkenyl, or alkynyl. In some embodiments, A in the compound of Formula III is a C1, C2, C3, C4, C5, C6, C7, C8, C9, C10, C1, C12, C13, C14, C15, C16, C17, C18,19, or C20 alkyl.

In some embodiments, a hydrophilic unit may have a structure represented by Formula IV:

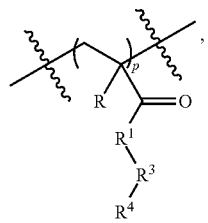

IV wherein:

R is hydrogen or a C1-C8 alkyl (e.g., a C1, C2, C3, C4, C5, C6, C7, or C8 alkyl);

$R^1$ is absent or is —O—, —NH—, or —CH$_2$—;

$R^3$ is selected from the group consisting of —(CH$_2$CH$_2$R$^5$)$_n$—, —C$_1$-C$_6$alkyl, —C$_1$-C$_6$alkyl-O—, and —C$_1$-C$_6$alkyl-SO$_3$— or a salt thereof, wherein $R^5$ is —O— or —CH$_2$— and n is an integer from 1 or 5 to 10, 25, 50, 75, 100, 1,000, 5,000, or 10,000;

$R^4$ is absent or is a hydrogen, alkyl, phosphono (e.g., dihydroxyphosphoryl), sulfono (e.g., hydroxysulfonyl), phosphatidyl choline (i.e., 2-(trimethylammonio)ethoxy(hydroxy)phosphoryl), phosphoryl, halo, hydroxyl, carboxyl, amino, ammonio, formyl or ester (e.g., pentafluorophenyl ester, succinimido ester, fluorophenyl ester, or 2,4-dinitrophenyl ester) group; and p is an integer from 1 to 10, 100, 1,000, 5,000, 10,000, 50,000, or 100,000.

In some embodiments, $R^4$ in the compound of Formula IV is a hydroxyl, carboxyl, amino, formyl, or ester group, optionally when $R^3$ is —(CH$_2$CH$_2$R$^5$)$_n$—, —C$_1$-C$_6$alkyl, or —C$_1$-C$_6$alkyl-O—. In some embodiments, when $R^3$ in the compound of Formula IV is —C$_1$-C$_6$alkyl-O— or —(CH$_2$CH$_2$R$^5$)$_n$— with $R^5$ being —O—, then $R^4$ may be a hydrogen, alkyl (e.g., methyl or ethyl group), phosphono (e.g., dihydroxyphosphoryl), sulfono (e.g., hydroxysulfonyl), phosphatidyl choline (i.e., 2-(trimethylammonio) ethoxy(hydroxy)phosphoryl), or phosphoryl group. In some embodiments, when $R^3$ in the compound of Formula IV is —C$_1$-C$_6$alkyl or —(CH$_2$CH$_2$R$^5$)$_n$— with $R^5$ being —CH$_2$—, then $R^4$ may be a hydroxyl, carboxyl, amino, ammonio, formyl, ester, phosphono, or sulfono group. In some embodiments, $R^4$ in the compound of Formula IV is a hydrogen, alkyl, phosphono, sulfono, phosphatidyl choline, phosphoryl, halo, hydroxyl, carboxyl, amino, ammonio, formyl, or ester group. In some embodiments, $R^4$ in the compound of Formula IV is a vinyl, epoxy, mercapto, azido, isocyanato, isothiocyanato, or maleimido group, which may optionally be added and/or provided after polymerization and/or by post-polymerization functionalization. In some embodiments, when $R^3$ in the compound of Formula IV is —C$_1$-C$_6$alkyl-SO$_3$— or a salt thereof, then $R^4$ is hydrogen or is absent. In some embodiments, $R^3$ in the compound of Formula IV is a salt (e.g., a sodium salt) of —C$_1$-C$_6$alkyl-SO$_3$— and $R^4$ is absent. In some embodiments, $R^3$ in the compound of Formula II is —(CH$_2$CH$_2$R$^5$)$_n$—.

In some embodiments, a compound of the present invention may comprise and/or be a telechelic polymer, which is a polymer or prepolymer that is capable of entering into further polymerization or other reactions through one or more of its reactive end-groups. In some embodiments, a compound of the present invention may comprise and/or be a heterotelechelic polymer, which is a polymer or prepolymer that is capable of entering into further polymerization or other reactions through a reactive end-group at each end of the polymer or prepolymer, and the two reactive end groups are not identical to each other. In some embodiments, a compound of the present invention may comprise and/or be a homotelechelic polymer, which is a polymer or prepolymer that is capable of entering into further polymerization or other reactions through a reactive end-group at each end of the polymer or prepolymer, and the two reactive end groups are identical to each other. In some embodiments, a compound of the present invention may comprise and/or be a semitelechelic polymer, which is a polymer or prepolymer that is capable of entering into further polymerization or other reactions through a reactive end-group at one end of the polymer or prepolymer.

A bioconjugate group may optionally be present in a compound of the present invention. "Bioconjugatable group", "bioconjugatable site", or "bioconjugate group" and grammatical variations thereof, refer to a moiety and/or functional group that may be used to bind or is bound to a biomolecule (e.g., a protein, peptide, DNA, RNA, etc.). Thus, "bioconjugatable group", "bioconjugatable site", or "bioconjugate group" and grammatical variations thereof do not comprise a biomolecule. However, in some embodiments, a bioconjugate group is used to bind to a biomolecule or a bioconjugate group or derivative thereof is bound to a biomolecule (e.g., a protein, peptide, DNA, RNA, etc.). Exemplary bioconjugatable groups include, but are not limited to, amines (including amine derivatives) such as isocyanates, isothiocyanates, iodoacetamides, azides, diazonium salts, etc.; acids or acid derivatives such as N-hydroxysuccinimide esters (more generally, active esters derived from carboxylic acids, e.g., p-nitrophenyl ester), acid hydrazides, etc.; and other linking groups such as aldehydes, sulfonyl chlorides, sulfonyl hydrazides, epoxides, hydroxyl groups, thiol groups, maleimides, aziridines, acryloyls, halo groups, biotin, 2-iminobiotin, etc. Linking groups such as the foregoing are known and described in U.S. Pat. Nos. 6,728,129; 6,657,884; 6,212,093; and 6,208,553. For example, a compound of the present invention may comprise a bioconjugate group that comprises a carboxylic acid and the carboxylic acid may be used for bioconjugation to a biomolecule (e.g., via carbodiimide-activation and coupling with an amino-substituted biomolecule).

In some embodiments, a biomolecule may comprise and/or be a protein (e.g., an antibody and/or a carrier protein), peptide, DNA, RNA, etc. In some embodiments, a biomolecule may comprise a moiety (e.g., a polymer) that optionally may include one or more (e.g., 1, 2, 3, 4, 5, 6, 7, 8, or more) binding sites for a compound of the present invention. In some embodiments, the biomolecule may be a member of a specific binding pair. "Specific binding pair" and "ligand-receptor binding pair" are used interchangeably herein and refer to two different molecules, where one of the molecules has an area on the surface or in a cavity of the molecule that specifically attracts or binds to a particular spatial or polar organization of the other molecule, causing both molecules to have an affinity for each other. The members of the specific binding pair can be referred to as ligand and receptor (anti-ligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-α and tumor necrosis factor-receptor, and interferon and interferon receptor; avidin and biotin or antibiotin; antibody and antigen pairs; enzymes and substrates; drug and drug receptor; cell-surface antigen and lectin; two complementary nucleic acid strands; nucleic acid strands and complementary oligonucleotides; interleukin and interleukin receptor; and stimulating factors and their receptors such as granulocyte-macrophage colony stimulating factor (GMCSF) and GMCSF receptor and macrophage colony stimulating factor (MCSF) and MCSF receptor.

A compound of the present invention may comprise a dye (e.g., a tetrapyrrole) that is covalently attached to a portion of a polymer as described herein. In some embodiments, the dye may be covalently attached to a terminal portion of the polymer. When present, a bioconjugate group may also be covalently attached to a portion of the polymer such as, for example, a terminal portion of the polymer. In some embodiments, the bioconjugate group is covalently attached to a first terminal portion (e.g., a first end) of the polymer and the dye is covalently attached to the opposite terminal portion (e.g., the opposite end) of the polymer.

A compound of the present invention may comprise a dye (e.g., a tetrapyrrole) that is covalently attached to a portion of the polymer and a bioconjugate group may be covalently attached to a portion of the dye. In some embodiments, the bioconjugate group is covalently attached to a first portion (e.g., a first end) of the dye and the polymer is covalently attached to a second portion (e.g., the opposite end) of the dye.

In some embodiments, a compound of the present invention or a portion thereof has a non-rigid backbone (e.g., a non-rigid polymer backbone) and/or has conformational flexibility. Conformational flexibility of molecular chains can be described and quantitated by the "persistence length" of the compound or portion thereof (e.g., the polymer portion). In some embodiments, the persistence length of a compound of the present invention may be on the order of the length of a given carbon-carbon bond.

A compound of the present invention may be self-folding such as, for example, self-folding in water and/or an aqueous solution. "Self-folding" as used herein refers to a compound transitioning from a partially or completely extended or unfolded structure to a structure wherein at least a portion of the extended or unfolded structure becomes folded upon contact with a solution (e.g., an aqueous solution) or compound, and the folding is innate as it occurs spontaneously (i.e., without external control or forces) upon contact with a solution. In some embodiments, a compound of the present invention self-folds upon contact with water and/or an aqueous solution. A compound of the present invention may self-fold into a unimer micellar structure, optionally upon contact with water and/or an aqueous solution.

In some embodiments, a compound of the present invention may be in the form of a particle. A compound of the present invention may form a particle such as, e.g., upon contact with a solution (e.g., an aqueous solution). In some embodiments, a single (i.e., 1) compound may form the particle. Thus, the compound and the particle are present in a ratio of about 1:1 (i.e., there is one compound per particle).

A compound of the present invention may comprise a portion of the one or more hydrophobic unit(s) in the core or interior region of the particle and/or a portion of the one or more hydrophilic unit(s) at the periphery or exterior region (e.g. shell) of the particle. In some embodiments, the particle has a micellar structure (e.g., a unimer micellar structure). A compound of the present invention may comprise a dye, which can be attached to a polymer of the present invention, and the dye may be encapsulated by a portion of the compound (e.g., a portion of the polymer) when the compound is in a folded structure and/or in the form of a particle (e.g., an unimer micellar structure). In some embodiments, the dye or a portion thereof and one or more hydrophobic unit(s) may be present in the core or interior region of the particle and one or more hydrophilic unit(s) may surround the dye and/or one or more hydrophobic unit(s).

In some embodiments, the hydrophobic units present in a polymer of the present invention may be one or more of the hydrophobic units of Formula III. In some embodiments, one or more of the hydrophobic units comprise an alkyl (e.g., dodecyl methyl) pendant functional group and/or are formed from a compound of Formula I and/or an alkyl acrylate (e.g., dodecyl methyl acrylate) monomer. In some embodiments, the hydrophilic units present in a polymer of the present invention may be one or more of the hydrophilic units of Formula IV and/or may be formed from a compound of Formula II. In some embodiments, one or more of the hydrophilic units comprise a non-ionic (i.e., neutral/uncharged) pendant functional group (e.g., PEG) and/or are formed from a non-ionic monomer (e.g., pegylated methyl acrylate (PEGA)). In some embodiments, one or more of the hydrophilic units comprise an ionic (e.g., anionic, charged) pendant functional group (e.g., sulfonic acid and/or sulfonate) and/or are formed from an ionic monomer (e.g., sulfonic acid acrylate (e.g., 2-acrylamido-2-methylpropane sulfonic acid)). In some embodiments, the hydrophilic units are formed from at least two different monomers such as, for example, a non-ionic (i.e., neutral/uncharged) hydrophilic monomer (e.g., pegylated methyl acrylate (PEGA)) and an ionic (e.g., anionic, charged) hydrophilic monomer (e.g., sulfonic acid acrylate (e.g., 2-acrylamido-2-methylpropane sulfonic acid)). As one of skill in the art understands, a monomer comprising an acid such as, e.g., sulfonic acid, may be present in the form of the acid and/or in its ionic form. In some embodiments, a monomer comprising an acid is predominately (i.e., greater than 50%) in its ionic form. In some embodiments, the ionic hydrophilic monomer is an acid in deprotonated form (e.g., deprotonated sulfonic acid acrylate) and/or in a salt form, e.g., a sodium sulfonate acrylate (e.g., 2-acrylamido-2-methylpropane sulfonic acid as the sodium salt).

In some embodiments, where two or more different hydrophilic units are present in a polymer of the present invention the ratio of the two or more different hydrophilic units can vary such as, for example from about 10:1 to about 1:10. For example, in some embodiments, a polymer comprises non-ionic (i.e., neutral/uncharged) hydrophilic units (e.g., formed from pegylated methyl acrylate (PEGA)) and ionic (e.g., anionic, charged) hydrophilic units (e.g., formed from sulfonic acid acrylate (e.g., 2-acrylamido-2-methylpropane sulfonic acid)) in a ratio of about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10 (non-ionic units:ionic units). In some embodiments, the ratio of hydrophilic unit(s) and hydrophobic unit(s) present in the backbone of a polymer of the present invention can vary. In some embodiments, the ratio of hydrophilic unit(s) and hydrophobic unit(s) present in the backbone of a polymer is about 1:1, 1:2, 1:3, 1:4, 1:5, 1:6, 1:7, 1:8, 1:9, or 1:10 (hydrophobic units:hydrophilic units).

In some embodiments, a polymer of the present invention comprises about 1% to about 40% hydrophobic units based on the total molar amount of monomers used to prepare the polymer and about 60% to about 99% hydrophilic units based on the total molar amount of monomers used to prepare the polymer. In some embodiments, a polymer of the present invention comprises about 1%, 5%, 10%, 15% or 20% to about 25%, 30%, 35%, or 40% hydrophobic units based on the total molar amount of monomers used to prepare the polymer and about 60%, 65%, 70%, 75%, or 80% to about 85%, 90%, 95%, or 99% hydrophilic units based on the total molar amount of monomers used to prepare the polymer. In some embodiments, the polymer comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% hydrophobic units based on the total molar amount of monomers used to prepare the polymer. In some embodiments, the polymer comprises less than about 30% (e.g., less than about 25%, 20%, 15%, 10%, or 5%) hydrophobic units based on the total molar amount of monomers used to prepare the polymer. In some embodiments, the polymer comprises about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98, or 99% hydrophilic units based on the total molar amount of monomers used to prepare the polymer. In some embodiments, the polymer comprises greater than about 70% (e.g., greater than about 75%, 80%, 85%, 90%, or 95%) hydrophilic units based on the total molar amount of monomers used to prepare the polymer.

A polymer of the present invention may have a weight fraction of hydrophobic units of about 1%, 5%, 10%, 15% or 20% to about 25%, 30%, 35%, or 40% based on the total weight of the polymer. In some embodiments, the polymer may have a weight fraction of hydrophobic units of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% based on the total weight of the polymer. In some embodiments, the polymer may have a weight fraction of hydrophobic units of less than about 30% (e.g., less than about 25%, 20%, 15%, 10%, or 5%) based on the total weight of the polymer.

A polymer of the present invention may have a weight fraction of hydrophilic units of about 60%, 65%, 70%, 75%, or 80% to about 85%, 90%, 95%, or 99% based on the total weight of the polymer. In some embodiments, a polymer of the present invention may have a weight fraction of hydrophilic units of about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98, or 99% based on the total weight of the polymer. In some embodiments, the polymer may have a weight fraction of hydrophilic units of greater than about 70% (e.g., greater than about 75%, 80%, 85%, 90%, or 95%) based on the total weight of the polymer.

In some embodiments, the amount of unimer micellar structures formed upon contact with a solution is about 50% to about 100%, about 75% to about 100%, about 85% to about 100%, or about 95% to about 100%, optionally as measured using sizing methods (e.g., dynamic light scattering (DLS)). In some embodiments, the amount of unimer micellar structures formed upon contact with a solution is about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, optionally as measured using sizing methods (e.g., dynamic light scattering (DLS)).

In some embodiments, dilution of a solution containing a compound of the present invention in the form of a unimer micellar structure results in no loss or a loss of less than about 20% of the unimer micellar structures present in the solution compared to the amount of unimer micellar structures present in the solution prior to dilution. In some embodiments, the amount of unimer micellar structures present in a solution does not change upon dilution or changes by less than about 20%, 19%, 18%, 17%, 16%, 15%, 14%, 13%, 12%, 11%, 10%, 9%, 8%, 7% 6%, 5%, 4%, 3%, 2%, 1%, or 0.1% compared to the amount of unimer micellar structures present in the solution prior to dilution.

In some embodiments, a solution comprising a compound of the present invention in the form of a unimer micellar structure comprises less than about 50% aggregates (e.g., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0.1%). Thus, at least 50% or more of the compound is not aggregated and may be in the form of a unimer micellular structure. In some embodiments, dilution of a solution comprising a compound of the present invention in the form of a unimer micellar structure results in no or minimal additional aggregate formation compared to the amount of aggregates present in the solution prior to dilution. In some embodiments, the amount of aggregates present in a solution comprising a compound of the present invention does not change upon dilution or changes by less than about 20%, 19%, 18%, 17%, 16%, 15%, 14%, 13%, 12%, 11%, 10%, 9%, 8%, 7% 6%, 5%, 4%, 3%, 2%, 1%, or 0.1% compared to the amount of aggregates present in the solution prior to dilution. In some embodiments, the diluted solution comprises less than about 50% aggregates (e.g., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0.1%).

A compound of the present invention may have a diameter (e.g., when folded such as in a unimer micellar structure) in a range of about 1 nm to about 50 nm or about 3 nm to about 30 nm in water and/or an aqueous solution. In some embodiments, the compound may have a diameter (e.g., when folded such as in a unimer micellar structure) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nm in water and/or an aqueous solution. In some embodiments, a compound of the present invention may be in the form of a particle (i.e., an at least partially folded structure).

In some embodiments, a compound of the present invention is cross-linked, optionally wherein the compound is cross-linked when the compound is in a folded structure. In some embodiments, a compound of the present invention may be in a solution (e.g., an aqueous solution) and/or may be cross-linked with a cross-linking agent. Cross-linking a compound of the present invention may comprise linking together two or more moieties and/or functional groups (e.g., pendant functional groups) of the hydrophobic unit(s) and/or hydrophilic unit(s). Cross-linking may provide the compound in a folded structure that cannot be unfolded without breaking one or more of the linkages formed by cross-linking. The degree or amount of cross-linking may be controlled, modified, and/or tuned, for example, by the amount of cross-linking agent reacted with the compound. In some embodiments, the step of cross-linking the compound may comprise a reaction and/or reactive entity (e.g., functional group) as listed in Table 1.

TABLE 1

Exemplary cross-linker reactions and functional groups.

| Reactions | Functional groups |
|---|---|
| Polymerization | Olefin |
| Polymerization | Acrylate |
| Thiol-ene reaction | Thiol group + olefin |
| Azide-alkyne reaction | Azido group + alkyne |
| Thiol-maleimide reaction | Thiol group + maleimide |
| Hydroxy + glutaraldehyde | Hydroxy + aldehyde |
| Amine + glutaraldehyde | Amino + aldehyde |
| Disulfide formation | Thiol + thiol |
| Amide formation | Amine + carboxylic acid |
| Ester formation | Hydroxy + carboxylic acid |
| Acetyl urea formation | Carbodiimide + carboxylic acid |
| Hydrazone formation | Hydrazide + aldehyde |

In a compound of the present invention, the fluorescence quantum yield of the dye when the compound is present in water and/or an aqueous solution may decrease by about 10% or less (e.g., 10%, 9%, 8%, 7%, 6%, 5%, 4%, 3%, 2%, 1%, or less) compared to the fluorescence quantum yield of the dye when the compound is present in a hydrophobic solvent (e.g., in toluene). Upon bioconjugation of a compound of the present invention to a biomolecule (e.g., a protein), the fluorescence quantum yield of the dye may be the same or substantially the same (e.g., within ±20%) as the fluorescence quantum yield of the dye in water and/or a hydrophobic solvent. In some embodiments, if the fluorescence quantum yield of the dye is 1.00 (theoretical maximum), then a decrease of 10-fold or less (e.g., about 10, 9,8, 7,6, 5,4, 3,2-fold or less) may be acceptable.

In some embodiments, a compound of the present invention is water soluble. The compound may have a solubility in water at room temperature in a range of about 1 mg/mL to about 10 mg/mL. In some embodiments, the compound has a solubility in water at room temperature of about 1,2,3, 4, 5,6, 7,8, 9,or 10 mg/mL.

In some embodiments, a compound and/or particle of the present invention is resistant to dilution. "Resistant to dilution" as used herein refers to the compound and/or particle retaining its structure and/or a property. In some embodiments, resistant to dilution refers to the compound and/or particle retaining a folded structure (e.g., an unimer micellar structure), which may be determined by measuring the diameter of the particle before and after dilution, and the diameter after dilution may remain within ±50%, 40%, 30%, 20%, 10% or less of the diameter prior to dilution. In some embodiments, resistant to dilution refers to the compound and/or particle retaining a fluorescence quantum yield of the dye after dilution within 50%, 40%, 30%, 20%, 10% or less of the fluorescence quantum yield of the dye prior to dilution. In some embodiments, a compound and/or particle of the present invention remains in a folded structure when diluted up to 25×, 50×, 75×, or 100× or when diluted to sub-micromolar concentrations.

Provided according to some embodiments of the present invention are methods of preparing compounds and/or compositions of the present invention. In some embodiments, a method of preparing a compound of the present invention comprises polymerizing a hydrophobic monomer and a hydrophilic monomer to provide a co-polymer; attaching a dye to a first portion (e.g., a terminal or end portion) of the co-polymer; and optionally attaching a bioconjugate group (e.g., a bioconjugatable group) to a second portion (e.g., the other terminal or end portion) of the co-polymer, thereby providing the compound. The hydrophobic monomer and hydrophilic monomer may be polymerized using any method known to those of skill in the art such as, but not limited to, via a condensation reaction (e.g., reaction with a diol and a diacid) and/or living radical polymerization (e.g., atom-transfer radical polymerization (ATRP) or reversible addition-fragmentation chain transfer (RAFT)). In some embodiments, polymerizing the hydrophobic monomer and the hydrophilic monomer is performed with a method that provides a co-polymer with one or both end groups of the co-polymer that are reactive (i.e., one or both of the end groups of the co-polymer are capable of entering into further polymerization or reactions), and the two end groups may be the same or different. In some embodiments, polymerizing the hydrophobic monomer and the hydrophilic monomer is via a living radical polymerization (e.g. ATRP) in the presence of an initiator (e.g., a bromide initiator), a catalyst (e.g., a ruthenium catalyst), and optionally a co-catalyst to provide a co-polymer. In some embodiments, polymerizing the hydrophobic monomer and the hydrophilic monomer is via a living radical polymerization (e.g. RAFT) in the presence of an initiator (e.g., AIBN) and a RAFT agent (e.g., thiocarbonylthio compound).

In some embodiments, attaching the dye to the first portion of the co-polymer may comprise reacting a monomer comprising the dye with a hydrophobic monomer and/or unit and/or hydrophilic monomer and/or unit. Thus, in some embodiments, the step of attaching the dye to the co-polymer may occur during or after the polymerization step. In some embodiments, the method comprises reacting a monomer comprising the dye with one or more (e.g., two or three) hydrophobic monomer(s) and/or unit(s) and/or one or more (e.g., two or three) hydrophilic monomer(s) and/or unit(s) during the step of polymerizing the hydrophobic monomer and the hydrophilic monomer. In some embodiments, polymerization of the one or more hydrophobic monomer(s) and the one or more hydrophilic monomer(s) occurs via a living radical polymerization (e.g., ATRP) in the presence of an initiator and the initiator comprises the dye. In some embodiments, polymerization of the one or more hydrophobic monomer(s) and/or the one or more hydrophilic monomer(s) occurs via a living radical polymerization (e.g., RAFT) in the presence of a radical initiator and the RAFT agent, optionally wherein the RAFT agent comprises a dye.

Exemplary terminal functional groups a co-polymer may comprise when the co-polymer is available for immediate dye-attachment or bioconjugation include, but are not limited to, those described in Table 2. These terminal functional groups are not pendant functional groups but may be present at either end of the co-polymer.

TABLE 2

Exemplary terminal functional group (FG) on the co-polymer and on the dye or biomolecule and exemplary linkage and chemistry.

| FG on the copolymer | FG on dye or biomolecule | Linkage | Chemistry |
| --- | --- | --- | --- |
| Hydroxy | Carboxyl | Ester | Ester formation |
| Carboxy | Hydroxy | Ester | Ester formation |
|  | Amino | Amide | Amide formation |
| Anhydride | Hydroxy | Ester | Ester formation |
|  | Amino | Amide | Amide formation |
| Formyl | Hydrazido | Hydrazone | Hydrazine-aldehyde chemistry |
| Formyl | Amino | Amine | Reductive amination |
| Haloaryl | Alkyne, alkene, or boronic esters | C-C | Pd- mediated coupling reaction |
| Olefin | Haloaryl | C-C | Heck coupling reaction |
| Olefin | Mercapto | Thioether | Thiol-ene reaction |
| Epoxy | Hydroxy | Ether | Nucleophilic ring-opening |
|  | Amino | Amine | |
| Mercapto | Malemeido | Thiol ether | Ether formation |
| Azido | Alkyne | Triazole | 'click' chemistry |
| Succinimido | Amino | Amide | Amide Formation |

Some functional groups may be labile under certain polymerization conditions. Hence, in some embodiments, a functional group may be introduced in a protected form. As a result, these functional groups may be available for dye attachment or bioconjugation upon deprotection. Exemplary protected forms of certain functional group include, but are not limited to, those listed in Table 3.

TABLE 3

Exemplary protected forms of certain functional groups.

| Protected form | Deprotected form |
| --- | --- |
| Acetal | Formyl |
| Ester | Carboxyl |
| N-succinimidyl ester | |
| Oxazoline | Carboxyl |
| NHBoc | Amino |
| Phthalimido | |
| Azido | |
| Silyl ether | Hydroxy |

In some embodiments, a portion (e.g., a terminal or end portion) of the co-polymer may comprise a halo group (e.g., Cl, Br, I). The halide portion of the co-polymer may be derivatized with nucleophiles or end-capping reagents to generate a functional group for dye attachment or bioconjugation. In some embodiments, a portion (e.g., a terminal end portion) of the co-polymer may comprise a thiol group, which may be derivatized with reagents comprising a thiol reactive group to generate a functional group for dye attachment or bioconjugation. Examples of thiol reactive groups include, but are not be limited to, halides (e.g., bromo, chloro, iodo), alkynes, aldehydes, vinyl ketones, and/or maleimido functional groups. All of the functional groups listed in Tables 2 and 3 are compatible with these strategies, and additional exemplary functional groups include, but are not limited to, those listed in Table 4.

TABLE 4

Exemplary terminal functional group (FG) on the co-polymer after derivatization and on the dye or biomolecule and exemplary linkage and chemistry

| FG on the co-polymer after derivatization | FG on dyes or biomolecules | Linkage | Chemistry |
| --- | --- | --- | --- |
| Azido | Alkyne | Triazole | 'click' chemistry |
| Pentafluorophenyl | Amino | Amide | Amide formation |
| Succinimido | Amino | Amide | Amide formation |
| Fluorophenyl | Amino | Arylamine | Aromatic nucleophilic substitution |
| Maleimido | Mercapto | Thioether | Thiol-ene reaction |
| Isocyanato | Amino | Urea | Amine-isocyanate chemistry |
| Isothiocyanato | Amino | Thiourea | Amine-isothiocyanate chemistry |
| Amino | Formyl, Carboxylic acid, Carboxyl, ester, Halo | Amine, amide | Condensation, Alkylation |
| Alkyne | halo | C-C | Metal mediated Catalysis |
| Hydroxy | Carboxyl | Ester | Ester formation |
| Carboxy | Hydroxy | Ester | Ester formation |
|  | Amino | Amide | Amide formation |
| Formyl | Amino | Amine | Reductive amination |
| Olefin | Haloaryl | C-C | Heck coupling reaction |
| Olefin | Mercapto | thioether | Thiol-ene reaction |

Polymerizing the hydrophobic monomer and the hydrophilic monomer (optionally via ATRP or RAFT) may comprise polymerizing the hydrophobic monomer and the hydrophilic monomer in a ratio of about 1:1, 1:2, 1:3, 1:4, 1:5, 1:6, 1:7, 1:8, 1:9, or 1:10 (hydrophobic monomer(s): hydrophilic monomer(s)). In some embodiments, the ratio may be about 1:1 to about 1:3 or about 1:6. In some embodiments, the hydrophobic monomer is an alkyl acrylate (e.g., dodecyl methyl acrylate) and/or the hydrophilic monomer is a glycol acrylate (e.g., PEGylated methyl acrylate). In some embodiments, one or more hydrophobic monomers are polymerized with two or more different hydrophilic monomers (optionally via RAFT or ATRP) in a ratio of about 1:1, 1:2, 1:3, 1:4, 1:5, 1:6, 1:7, 1:8, 1:9, or 1:10 (hydrophobic monomer(s):hydrophilic monomer(s)). For example, in some embodiments, a first hydrophilic monomer may be ionic (e.g., a sulfonic acid acrylate monomer (e.g., 2-acrylamido-2-methylpropane sulfonic acid) and/or a sulfonate monomer) and a second hydrophilic monomer may be non-ionic (e.g., a glycol acrylate (e.g., PEGylated methyl acrylate)). The ratio of the first hydrophilic monomer and the second hydrophilic monomer may vary (e.g., the ratio of the first hydrophilic monomer:second hydrophilic monomer may be about 6:1, 5:1, 4:1, 3:1, 2:1, 1:1, 1:2, 1:3, 1:4, 1:5, or 1:6).

Exemplary catalysts that may be used in a method of the present invention include, but are not limited to, a ruthenium complex, iron complex, copper complex, nickel complex, palladium complex, rhodium complex, and rhenium complex. Exemplary ruthenium complexes include, but are not limited to, dichlorotris(triphenylphosphine)ruthenium(II) [RuCl$_2$(PPh$_3$)$_3$], pentamethylcyclopentadienylbis(triphenylphosphine)ruthenium(II) chloride [RuCp*Cl(PPh$_3$)$_2$], chloro(cyclopentadienyl)bis(triphenylphosphine)ruthenium [RuCpCl(PPh$_3$)$_2$], dihydridotetrakis(triphenylphosphine)ruthenium(II) [RuH$_2$(PPh$_3$)$_4$], and dichloro(p-cymene)ruthenium(II) dimer. Exemplary iron complexes include, but are not limited to, dichlorobis(triphenylphosphine)iron (II) [FeCl$_2$(PPh$_3$)$_2$], bromo(cyclopentadienyl)dicarbonyliron(II) [FeCpBr(CO)$_2$], and cyclopentadienyliron dicarbonyl dimer. In some embodiments, copper complexes generated in-situ with copper salts and ligands may be used and exemplary copper salts include, but are not limited to, cuprous chloride, cuprous bromide, cuprous triflate, cuprous hexafluorophosphate, and cuprous acetate, etc. Exemplary nitrogen-based ligands include, but are not limited to, 2,2'-bipyridine and its derivatives, 1,10-phenanthroline and its derivatives, sparteine and other diamines, and terpyridine and its derivatives. Exemplary nickel complexes include, but are not limited to, dibromobis(triphenylphosphine)nickel(II) [NiBr$_2$(PPh$_3$)$_2$], and tetrakis(triphenylphosphine)nickel [Ni(PPh$_3$)$_4$]. An exemplary palladium complex is tetrakis(triphenylphosphine)palladium [Pd(PPh$_3$)$_4$]. An exemplary rhodium complex is tris(triphenylphosphine)rhodium bromide. An exemplary rhenium complex is dioxobis(triphenylphosphine)rhenium iodide. In some embodiments, the catalyst is a pentamethylcyclopentadienylbis(triphenylphosphine)ruthenium(II) chloride.

A co-catalyst may optionally be present in a method of the present invention such as, e.g., in the step of polymerizing the hydrophobic monomer and the hydrophilic monomer. In some embodiments, a co-catalyst may be present and may be 4-(dimethylamino)-1-butanol.

In some embodiments, a method of the present invention comprises hydrolyzing the co-polymer, optionally in the presence of trifluoroacetic acid and water, to provide a formyl group at the first portion (e.g., the first terminus) of the co-polymer. The method may comprise reacting the dye and the formyl group of the co-polymer to form a hydrazone bond between the dye and the co-polymer, optionally via aldehyde-hydrazide chemistry, to thereby attach the dye to the first portion of the co-polymer. In some embodiments, a biomolecule may be attached by reacting the formyl group with an amine group on the bioconjugate group via reductive amination.

In some embodiments, a method of the present invention comprises reacting the co-polymer with mercaptoacetic acid and triethylamine to provide a carboxymethylthioether group at the second portion (e.g., the second terminus) of the co-polymer. The carboxymethylthioether group may be derivatized to provide a N-hydroxysuccinimide ester at the second portion of the co-polymer. A biomolecule (e.g., avidin) may be attached to the N-hydroxysuccinimide ester at the second portion of the co-polymer.

In some embodiments, a method of the present invention comprises reacting the co-polymer with sodium azide to provide an azido group, and optionally attaching a dye to the azido group via copper-catalyzed azide-alkyne chemistry.

In some embodiments, a method of the present invention comprises a RAFT polymerization. In some embodiments, RAFT polymerization occurs in the presence of a radical initiator (e.g., AIBN) and a RAFT agent such as, for example, a thiocarbonylthio compound. Additional examples of RAFT agents include, but are not limited to, dithioesters, dithiocarbamates, trithiocarbonates, dithiobenzoates and/or xanthates.

In some embodiments, a method of the present invention comprises cleaving the thiocarbonylthio functionality present on a terminal end of the co-polymer obtained using RAFT polymerization. Such cleavage may occur using any general methods known in the art. For example, in some embodiments, the thiocarbonylthio functionality is cleaved via aminolysis, e.g., in the presence of ethanolamine, to render the free thiol. In some embodiments, the free thiol may be coupled to a dye comprising a maleimido functionality thereby attaching the dye to a first portion (e.g., terminal end) of the co-polymer. In some embodiments, a biomolecule may be attached to the free thiol group of the first portion (e.g., terminal end). In some embodiments, a biomolecule may be attached to the opposite terminal end of the polymer.

According to some embodiments, a compound and/or composition of the present invention may be used in flow cytometry. Flow cytometry is known and described in, for example, U.S. Pat. Nos. 5,167; 5,915,925; 6,248,590; 6,589,792; and 6,890,487. In some embodiments the particle being detected, such as a cell, is labeled with a luminescent compound, such as a compound of the present invention, for detection. Labeling can be carried out by any suitable technique such as, e.g., binding the luminescent compound (e.g., a compound the present invention) to the particle or cell such as through an antibody that specifically binds to the particle or cell, by uptake or internalization of the luminescent compound into the cell or particle, by non-specific adsorption of the luminescent compound to the cell or particle, etc. The compounds described herein may be useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

In some embodiments, provided is a method of detecting cells and/or particles using flow cytometry, the method comprising labeling cells and/or particles with a compound of the present invention and detecting the compound by flow cytometry, thereby detecting the cells and/or particles.

In some embodiments, provided is a method of detecting a tissue and/or agent (e.g., a cell, infecting agent, etc.) in a subject, the method comprising: administering to the subject a compound and/or composition of the present invention, optionally wherein the compound associates with the tissue and/or agent; and detecting the compound within the subject, thereby detecting the tissue and/or agent.

In some embodiments, provided is a method for using a compound of the present invention in photodynamic therapy (PDT) and/or photodynamic inactivation (PDI). Photodynamic therapy (PDT) is a form of phototherapy involving light and a photosensitizing chemical substance (e.g., a compound of the present invention) that is used in conjunction with molecular oxygen to elicit cell death (phototoxicity). PDT can be used to kill microbial cells, including bacteria, fungi and viruses. PDT may also be used to treat cancer. When light energy is administered in photodynamic therapy (PDT) to destroy tumors, various forms of energy are within the scope of this invention, as will be understood by those of ordinary skill in the art. Such forms of energy include, but are not limited to, thermal, sonic, ultrasonic, chemical, light, microwave, ionizing (such as x-ray and gamma ray), mechanical, and/or electrical. For example, sonodynamically induced or activated agents include, but are not limited to, gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

Examples of treatment areas include, but are not limited to, the following:

(i) Treatment of Opportunistic Infections.

Compounds, compositions and/or methods of the present invention may be useful for PDT of opportunistic infections, particularly of soft tissue. For antimicrobial treatment (via PDT) of infections, particularly wound infections, the infecting organism may include (as non-limiting examples) *Staphylococcus aureus, Pseudomonas aeruginosa*, and/or *Escherichia coli*. In nosocomial infections, *P. aeruginosa* is responsible for 8% of surgical-wound infections and 10% of bloodstream infections. In some embodiments, a subject is an immunocompromised subject, such as, e.g., those afflicted with AIDS and/or undergoing treatment with an immunosuppressive agent.

(ii) Treatment of Burns.

Infections by *S. aureus* and gram-positive bacteria in general are particularly pronounced in burns (Lambrechts, 2005). The multidrug resistance of *S. aureus* presents significant medical challenges. In this regard, compounds, compositions and/or methods of the present invention may be useful for the treatment of opportunistic infections of burns.

(iii) Sepsis.

Compounds, compositions and/or methods of the present invention may be useful for the PDT treatment of a subject afflicted with opportunistic infections of *Vibrio vulnificus. V. vulnificus*, a gram-negative bacterium, causes primary sepsis, wound infections, and/or gastrointestinal illness in a human.

(iv) Ulcers.

Compounds, compositions and/or methods of the present invention may be useful for PDT treatment of the bacterium that causes ulcers (*Helicobacter pylori*). In the clinic, treatment may be effected in any suitable manner, such as, e.g., by insertion of a fiber optic cable (akin to an endoscope but with provisions for delivery of red or near-IR light) into the stomach and/or afflicted region.

(v) Periodontal Disease.

Compounds, compositions and/or methods of the present invention may be useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include, but are not limited to, *Porphyromonas gingivalis, Actinobacillus actinomycetemcomitans, Bacteroides forsythus, Campylobacter rectus, Eikenella corrodens, Fusobacterium nucleatum* subsp. *Polymorphum, Actinomyces viscosus*, and the streptococci. For such applications the compounds and/or compositions of the present invention may be topically applied (e.g., as a mouthwash or rinse) and then light administered with an external device, in-the-mouth instrument, or combination thereof.

(vi) Atherosclerosis.

Compounds, compositions and/or methods of the invention may be useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Bacteriochlorins targeted to such inflammatory macrophages may be useful for PDT of vulnerable plaque.

(vii) Cosmetic and Dermatologic Applications.

Compounds, compositions and/or methods of the present invention may be useful in PDT to treat a wide range of cosmetic dermatological problems, such as hair removal, treatment of psoriasis, and/or removal of skin discoloration. Ruby lasers are currently used for hair removal; in many laser treatments melanin is the photosensitized chromophore. Such treatments work reasonably well for fair-skinned individuals with dark hair. Compounds, compositions and/or methods of the present invention may be used as near-IR sensitizers for hair removal, which enables targeting a chromophore with a more specific and/or sharp absorption band.

(viii) Acne.

Compounds, compositions and/or methods of the present invention may be useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and/or compositions of the present invention may be administered to a subject topically or parenterally (e.g., by subcutaneous injection) depending upon the particular condition.

(ix) Infectious Diseases.

Compounds, compositions and/or methods of the present invention may be useful in PDT to treat infectious diseases. For example, Cutaneous leishmaniasis and sub-cutaneous leishmaniasis, which occurs extensively in the Mediterranean and Mideast regions, is currently treated with arsenic-containing compounds. PDT has been used to reasonable effect recently, at least in one case, on a human subject. The use of compounds and/or compositions of the present invention are likewise useful, and potentially offer advantages such as ease of synthesis and better spectral absorption properties.

(x) Tissue Sealants.

Compounds, compositions and/or methods of the present invention may be useful in PDT as tissue sealants in a subject in need thereof. Light-activated tissue sealants are attractive for sealing wounds, bonding tissue, and/or closing defects in tissue. There are many applications where sutures and/or staples are undesirable, and use of such mechanical methods of sealing often leads to infection and/or scarring.

(xi) Neoplastic Disease.

Compounds, compositions and/or methods of the present invention may be useful in PDT for treating neoplastic diseases and/or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and/or Kaposi sarcoma.

During photodynamic therapy a compound of the invention is administered to a subject in need thereof (e.g. a subject having any of the above mentioned diseases). The administered compound may associate with the diseased tissue present inside the subject, and exposure of the subject to a light source emitting a suitable light with the proper wavelength and intensity may activate the compound (e.g., release reactive oxygen species (ROS)) into the diseased tissue thereby treating the diseased tissue, optionally without affecting the healthy tissue. For example, in some embodiments, the diseased tissue is a hyperproliferative tissue (e.g., a tumor).

The present invention is explained in greater detail in the following non-limiting examples.

EXAMPLES

Example 1—Single-Polymeric Encapsulation of a Single Hydrophobic Fluorophore

Studies were carried out of random copolymers bearing pendant PEGylated fluorophores and of polymerized micelles containing hydrophobic fluorophores. Ultimately a design was identified that entails a heterotelechelic, amphiphilic, random copolymer derived via living radical polymerization (via RuCp*Cl(PPh$_3$)$_2$, 4-(dimethylamino)-1-butanol and an acetal-substituted initiator in ethanol at 40° C.) from two acrylate monomers—a hydrophilic (pendant PEG-6) monomer and a hydrophobic (dodecyl) monomer in 3:1 ratio. Hydrolysis of the acetal followed by reaction with a hydrophobic chlorin-hydrazide afforded the polymer (i.e., a foldamer or single-chain nanoparticle, abbreviated as scNp) bearing a single chlorin-hydrazone. Examination of the chlorin-polymer in aqueous solution revealed sharp absorption/fluorescence bands and undiminished fluorescence quantum yield compared with the chlorin in toluene. The approach separates fluorophore choice and aqueous solubilization strategy into distinct spheres, with implementation of the latter now being quite simple.

Three hydrophobic-dye-labeled amphiphilic copolymers F1-F3 with self-folding properties were synthesized and characterized spectroscopically. The structural features of the hydrophobic dyes and the polymer backbones are shown in Scheme 1. The amphiphilic copolymer is composed of a hydrophilic segment (PEG segment) and a hydrophobic segment (dodecyl segment) in a ratio of 3 to 1, with a molecular weight around 120 kDa. As a random block copolymer, the copolymer in water can self-fold to create a hydrophobic center, encapsulating the hydrophobic dye and thereby protecting the dye from aggregation. The three hydrophobic dyes, i.e. the BODIPY, the chlorin, and the phthalocyanine differ in molecular size and absorption wavelength (540, 640, and 700 nm, respectively), were loaded on the same polymer backbone and resorted to spectroscopic measurements. While not wishing to be bound to any particular theory, the resulting distinct fluorescence properties of the dye-loaded copolymers in water suggest that the effectiveness of dye encapsulation may depend on the molecular size of the dye and the length of the copolymer backbone.

Scheme 1. Target amphiphilic dye-loaded copolymer F1-F3.

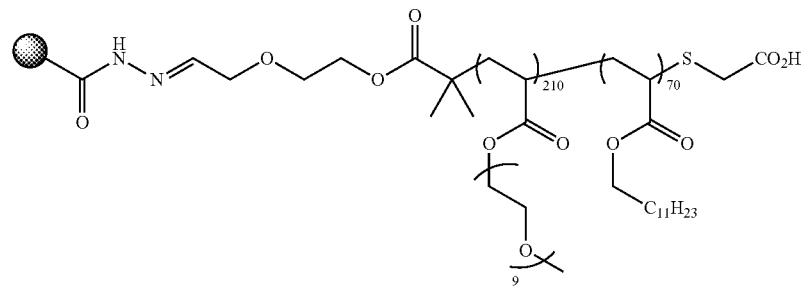

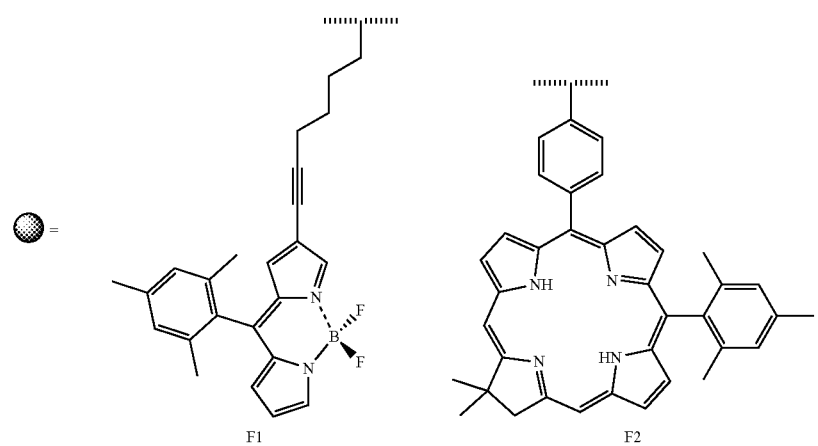

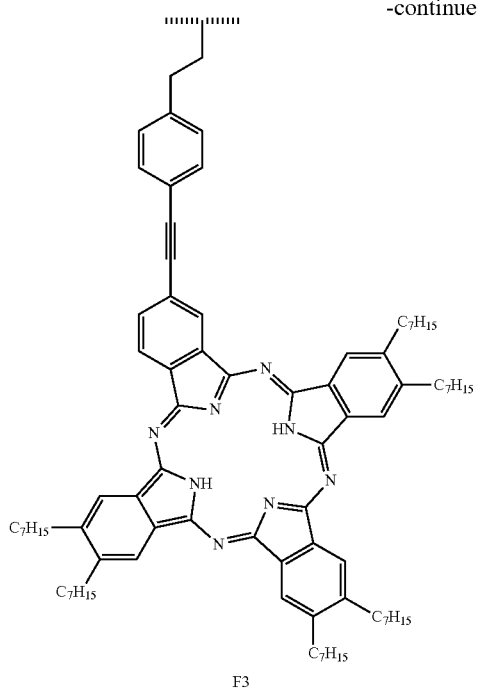

F3

Synthesis of Hydrophobic Fluorophores.

In general, the dye-hydrazides used here for dye attachment were prepared from the corresponding carboxylic ester via amide formation. Treatment of the BODIPY-NHS ester 1, which is an activated carboxyl species, with hydrazine hydrate afforded the desired BODIPY-hydrazide D1 in 40% yield (Scheme 2).

Scheme 2. Synthesis of the BODIPY-hydrazide D1.

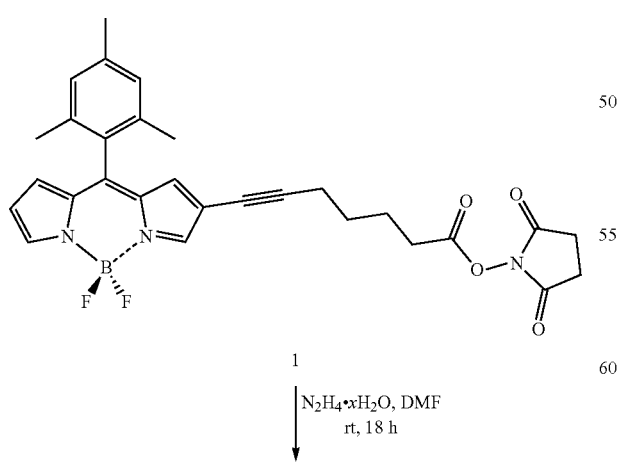

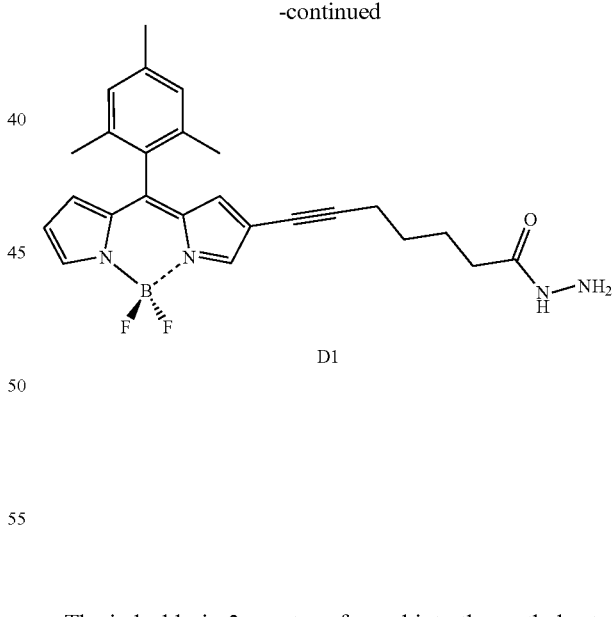

The iodochlorin 2 was transformed into the methyl ester 3 via carbonyl insertion quantatively in the presence of $Pd(PPh_3)_4$, methanol and carbon monoxide (Scheme 3). The methyl ester 3 was then treated with hydrazine hydrate under reflux condition, generating the desired chlorin-hydrazide D2 in 83% yield. It was noticed that the reaction needs to be carried out at a concentration below 50 mM, since a more concentrated solution resulted in the reduction of D2 to the corresponding bacteriochlorin.

Scheme 3. Synthesis of the chlorin-hydrazide D2.

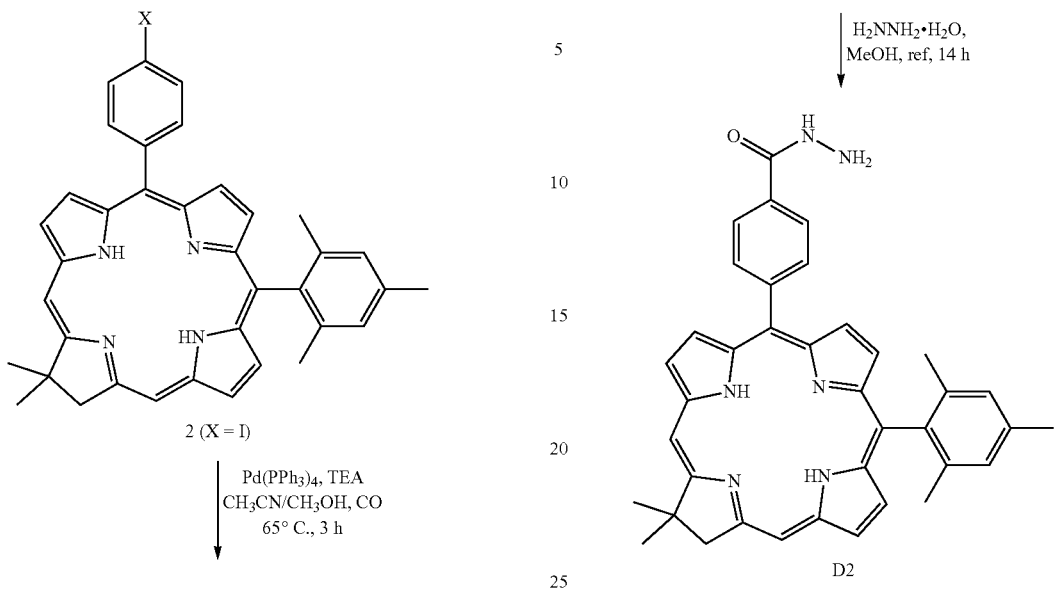

2 (X = I)

Pd(PPh₃)₄, TEA
CH₃CN/CH₃OH, CO
65° C., 3 h 3 (X = CO₂Me)

H₂NNH₂·H₂O,
MeOH, ref, 14 h

D2

The preparation of the phthalocyanine-hydrazide D3 took more efforts due to the solubility limitations of the macrocycle. Ethynyl phthalocyanine 4 was coupled with methyl 3-(4-bromophenyl)propanoate in the presence of Pd(OAc)$_2$/P(o-tol)$_3$ to afford the methyl ester 5 in 13% yield (Scheme 4). Again, the low solubility of the macrocycle in the reaction system accounts for the low yield of the Sonogashira coupling reaction. The methyl ester 5 was then treated with hydrazine in a mixture of toluene and methanol to generate the desired hydrazide D3.

Scheme 4. Synthesis of the phthalocyanine-hydrazide D3.

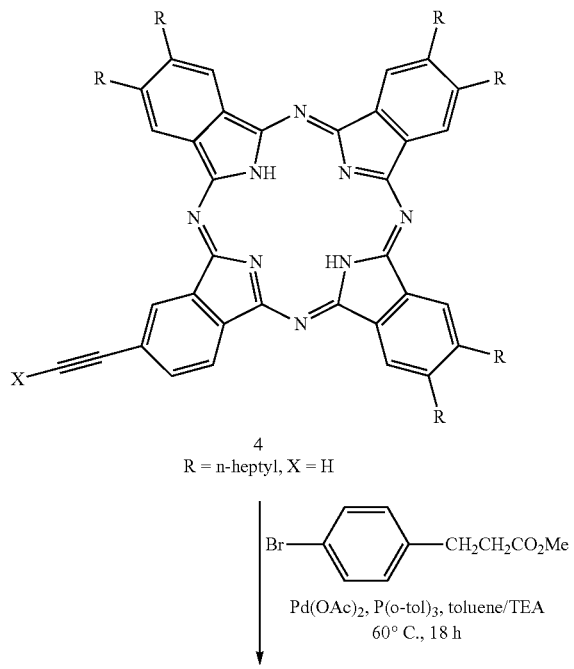

4
R = n-heptyl, X = H

Br—⟨⟩—CH₂CH₂CO₂Me

Pd(OAc)₂, P(o-tol)₃, toluene/TEA
60° C., 18 h

-continued

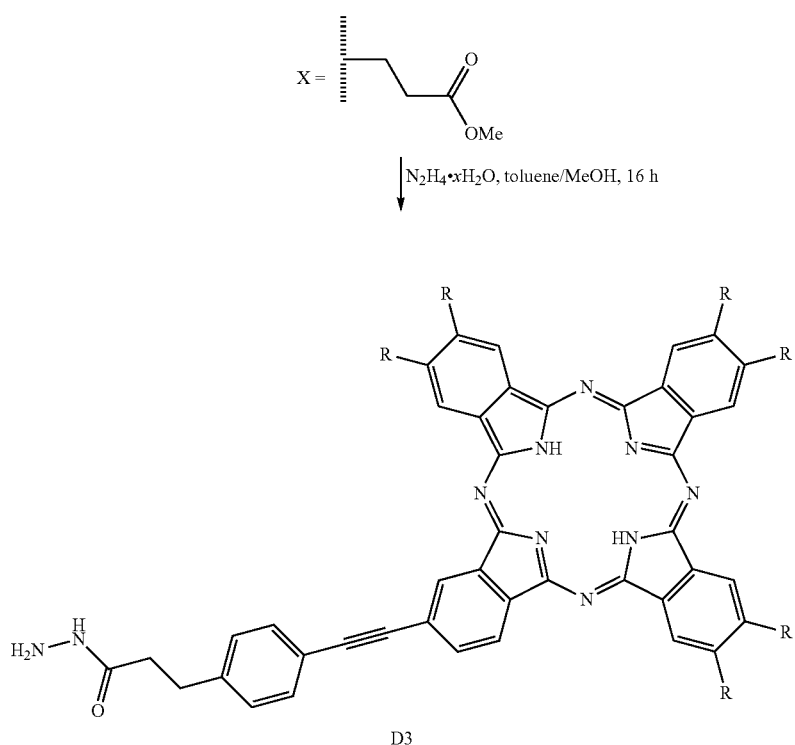

D3

Synthesis of the Copolymer.

The living radical polymerization of monomer PEGA and LA was carried out in a 3 to 1 ratio with the reported initiator 6 in the presence of RuCp*Cl(PPh$_3$)$_2$ and 4-dimethylaminobutanol (Scheme 5). The resulting copolymer 7 is heterotelechelic with an acetal at one end, and a bromide at the other end. The two functional groups were derivatized for further dye attachment and the installation of a bioconjugatable handle, respectively. The bromide in 7 was substituted with mercaptoacetic acid, affording a carboxyl group at the end of the copolymer open to bioconjugation. Hydrolysis of the acetal end under acidic condition resulted in the formyl copolymer 8. This copolymer 8 served as a platform for dye conjugation, generating the target dye-loaded copolymer F1-F3 via the treatment with hydrazide D1-D3, respectively.

Scheme 5. Preparation of the dye-loaded amphiphilic copolymer F1-F3.

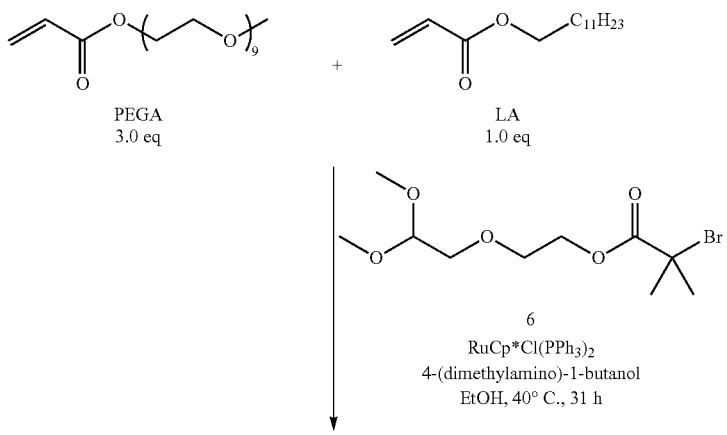

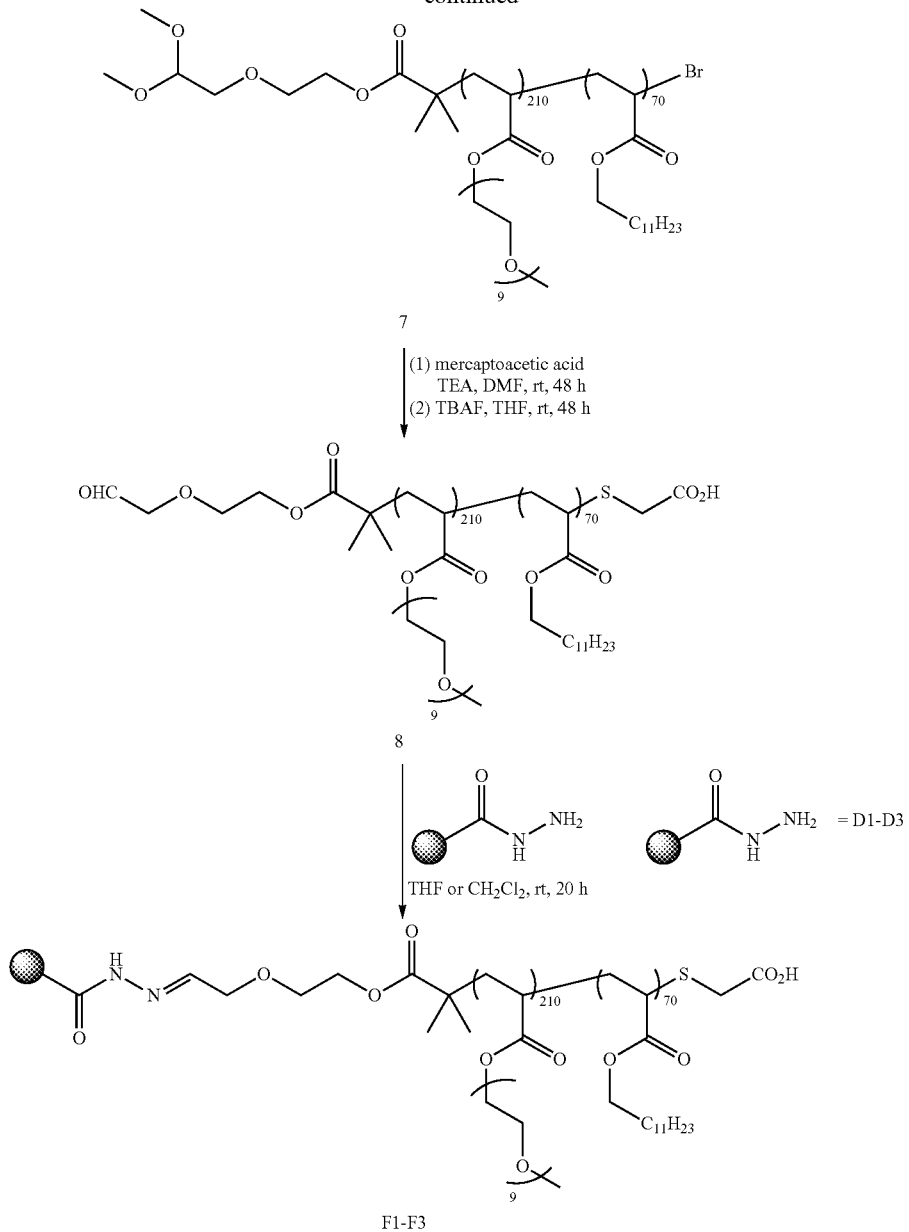

F1-F3

SEC Analysis.

Figure 2:
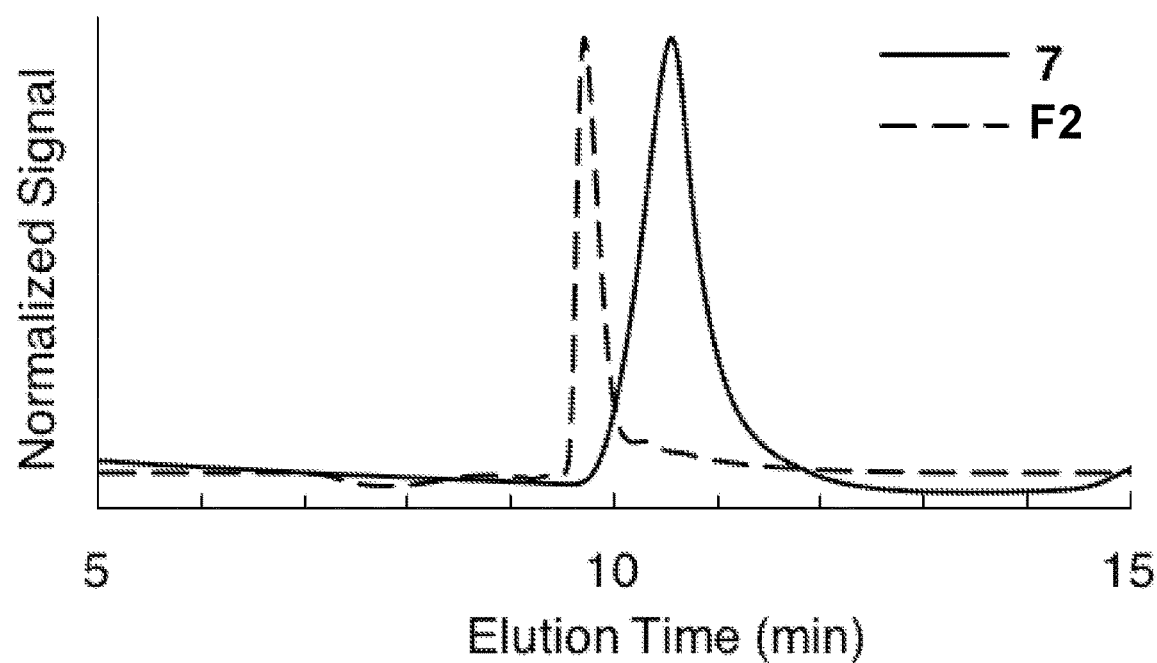
FIG. 2 is an SEC elution trace for the copolymer 7 (solid) and chlorin-loaded copolymer F2 (dashed). Samples were eluted with THF and detected with a refractive index detector.

Taking F2 as an example, analytical SEC was used to monitor the process of dye-attachment reaction. The SEC traces shown in FIG. 2 indicate an increase in the size upon the linkage of a chlorin onto the copolymer. Also, the molecular weight of the copolymer 7 was estimated to be $1.2\times10^5$ g/mol based on SEC analysis.

Measurements of Absorption and Emission Spectra.

Figure 3:
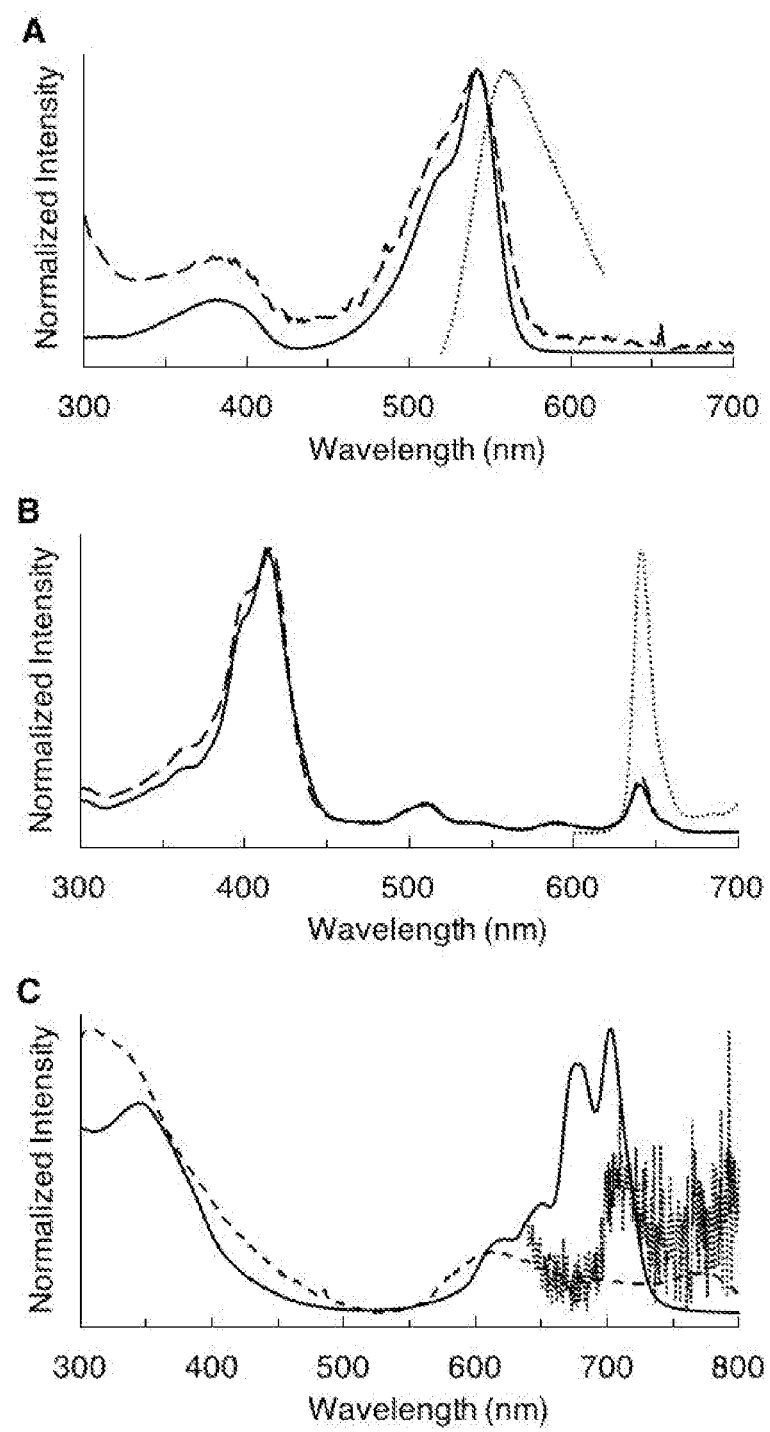
FIG. 3 shows three different absorption spectra. Panel (A) shows the absorption spectrum of D1 in $CH_2Cl_2$ (solid), as well as absorption (dashed) and emission (dotted) spectra of F1 in water at μM concentration. Panel (B) shows the absorption spectrum of D2 in $CH_2Cl_2$ (solid), as well as absorption (dashed) and emission (dotted) spectra of F2 in water at μM concentration. Panel (C) shows the absorption spectrum of D3 in toluene (solid), as well as absorption (dashed) and emission (dotted) spectra of F3 in water at μM concentration. All spectra were measured at room temperature.

The target dye-loaded copolymers F1-F3 were then subject to investigations of their spectroscopic properties in both organic solvents and aqueous solution. The spectra are shown in FIG. 3. For both F1 (BODIPY-loaded, FIG. 3, panel A) and F2 (chlorin-loaded, FIG. 3, panel B), absorption spectra of samples in aqueous solution at μM concentration are comparable to those of organic solutions. Attaching to the 120-kDa amphiphilic copolymer drastically enhances the water solubility of BODIPY D1 and chlorin D2 without strong perturbation on the spectroscopic properties. Emission band for F1 and F2 in water remains the same as the ones measured in organic solutions, showing minimal dye-dye interaction is involved in aqueous solution of F1 and F2 at μM concentration. Nevertheless, as the largest in the molecular size of the dye, phthalocyanine-loaded copolymer F3 afforded a completely different absorption spectra in water from the one in toluene (FIG. 3, panel C), with a fully quenched fluorescence. This negative result may be because of the inappropriate size of the copolymer backbone. Polymer larger in size may be required to encapsulate large hydrophobic fluorophores like the phthalocyanine D3.

Fluorescence Quantum Yields.

Fluorescence quantum yield was also measured for F1-F3 in water at room temperature. The data along with other spectroscopic data are summarized in Table 5. Taking the chlorin-attached copolymer F2 as an example, the dye-copolymer conjugate exhibits a fluorescence quantum yield at 0.18 in water at µM concentration (Entry 6), which is similar to the value from a $CH_2Cl_2$ solution of only the dye D2 (0.19, Entry 4). Analogous results were observed for the BODIPY-labeled copolymer F1 ($\Phi_f$=0.058, Entry 3) and the BODIPY dye D1 (0.065, Entry 1). These comparisons indicate the absence of dye-dye quenching resulting from the aggregation for F1 and F2 in µM aqueous solutions. The results demonstrate the amphiphilic copolymer as a successful platform for the encapsulation of hydrophobic fluorophores in water when the length of the polymer chain is appropriate. As mentioned above, however, the phthalocyanine-labeled copolymer has a fully quenched fluorescence. A longer polymer chain may be more effective on the encapsulation of larger fluorophores like D3. Also, a smaller phthalocyanine skeleton (e.g. with methyl instead of heptyl as peripheral groups) may be encapsulated with the current length of copolymer successfully.

TABLE 5

Spectroscopic properties of copolymer F1-F3 and fluorophores D1-D3.

| Entry | Dye | Solvent | $\lambda_{abs}^{max}$ (nm) | FWHM ($cm^{-1}$) | $\lambda_{em}$ (nm) | $\Phi_f$ |
|---|---|---|---|---|---|---|
| 1 | D1 | $CH_2Cl_2$ | 543 | 1628 | 557 | 0.065 |
| 2 | F1 | $CH_2Cl_2$ | 542 | 2155 | 556 | 0.060 |
| 3 | F1 | Water | 542 | 2071 | 559 | 0.058 |
| 4 | D2 | $CH_2Cl_2$ | 640 | 342 | 641 | 0.19 |
| 5 | F2 | $CH_2Cl_2$ | 640 | 327 | 641 | 0.19 |
| 6 | F2 | Water | 641 | 292 | 641 | 0.18 |
| 7 | D3 | Toluene | 702 | 1113 | 707 | 0.68 |
| 8 | F3 | Water | 608 | NA | NA | 0.0028 |

Experimental Section

General Methods.

All chemicals obtained commercially were used as received unless otherwise noted. Reagent-grade solvents ($CH_2Cl_2$, THF, methanol) and HPLC-grade water were used as received. NMR data was measured in a solution of $CDCl_3$ unless otherwise noted. Noncommercial compounds 1, 2, and 4 were prepared following literature procedures. Analytical SEC experiments were performed with PLgel 10000 Å SEC column, eluted with ACS grade THF (stablized with 400 ppm of BHT) at 35° C. with a flow rate at 1 mL/min. Samples were detected with Agilent 1260 infinity refractive index detector. Absorption spectra were measured on Agilent 8453 and Shimadzu UV1800 instruments using dilute (µmolar) solutions of the compound in UV transparent (e.g., quartz) cuvettes versus a solvent blank at room temperature.

2-[6-(N-Aminocarbamoyl)hex-1-yn-1-yl]-8-mesityl-4,4-difluoro-4-bora-3a,4a-diaza-s-indacene (D1)

A solution of 1 (9.0 mg) in THF (500 µL) was treated with hydrazine hydrate (5.3 µL) at room temperature for 30 min. Then the solution was concentrated and chromatographed (silica gel, $CH_3OH$/acetic acid=9:1) to afford a red solid (3.0 mg, 39%): 1H NMR (DMSO-$d_6$, 300 MHz) δ 8.85 (br, 1H), 7.99 (s, 1H), 7.94 (s, 1H), 6.95 (s, 2H), 6.76 (d, J=4.2 Hz, 1H), 6.72 (s, 1H), 6.53 (d, J=4.2 Hz, 1H), 2.45-2.47 (m, 2H), 2.36 (s, 3H), 2.17-2.20 (m, 2H), 2.09 (s, 6H), 1.58-1.42 (m, 4H); MALDI-MS obsd 449.1 [(M+H)+], 429.2 [(M-F)+], calcd 448.2 (M=$C_{25}H_{27}BF_2N_4O$).

10-Mesityl-5-(4-methoxycarbonyl)phenyl-18,18-dimethylchlorin (3)

Toluene and methanol were deaerated by bubbling with argon for 1 h. A conical vial with a rubber septum was charged with iodochlorin 2 (20 mg, 0.030 mmol, 1.0 equiv) and Pd(PPh$_3$)$_4$ (3.5 mg, 3.0 µmol, 0.10 equiv), and then evacuated under high vacuum. The vial was then refilled with argon. This evacuation-purge process was repeated for three times. The deaerated toluene (0.50 mL) and methanol (0.50 mL) were added to the vial under argon, as well as triethylamine (21 µL, 0.15 mmol, 5.0 equiv). The solution was deaerated again with three times of the freeze-pump-thaw cycle. The vial was evacuated under high vacuum at 77 K, and then refilled with carbon monoxide. A balloon full of CO was also connected to the vial to provide extra pressure. The solution was stirred at 65° C. for 23 h, concentrated and chromatographed (silica gel, hexanes/$CH_2Cl_2$=1:1) to afford a green solid (18 mg, 100%): TLC (silica, hexanes/$CH_2Cl_2$=1:1) $R_f$=0.28; 1H NMR (300 MHz) δ 8.92 (s, 1H), 8.87 (s, 1H), 8.82 (d, J=4.8 Hz, 1H), 8.73 (d, J=4.7 Hz, 1H), 8.69 (d, J=4.7 Hz, 1H), 8.61 (d, J=4.7 Hz, 1H), 8.38 (d, J=8.1 Hz, 2H), 8.37 (s, 1H), 8.36 (s, 1H), 8.22 (d, J=8.3 Hz, 2H), 7.22 (s, 2H), 4.57 (s, 2H), 4.08 (s, 3H), 2.58 (s, 3H), 2.03 (s, 6H), 1.84 (s, 6H), −1.87 (br, s, 2H); 13C NMR (100 MHz) δ 175.2, 167.6, 163.6, 152.4, 151.5, 147.2, 140.9, 140.4, 139.2, 138.3, 137.7, 134.7, 134.4, 134.1, 132.1, 131.1, 129.5, 128.1, 128.0, 127.8, 123.7, 123.6, 120.59, 120.57, 96.81, 94.99, 52.49, 51.86, 46.63, 31.31, 21.57, 21.45; ESI-MS obsd 592.2851 [(M+H)+], calcd 592.2838 (M=$C_{39}H_{36}N_4O_2$); labs ($CH_2Cl_2$) 415, 509, 533, 590, 641 nm.

5-[4-(N-Aminocarbamoyl)phenyl]-10-Mesityl-18,18-dimethylchlorin (D2)

A solution of chlorin 3 (44 mg, 75 µmol, 1.0 equiv) in THF (1.0 mL) was treated with methanol (1.0 mL) and hydrazine hydrate (0.21 mL, 3.8 mmol, 50 equiv) at 50° C. for 24 h. [Note: Reduction of the chlorin-hydrazine to the corresponding bacteriochlorin-hydrazine will happen if the concentration is larger than 50 mM. The bacteriochlorin can be oxidized back to the desired chlorin by the treatment of DDQ (1.0 equiv) in $CH_2Cl_2$ at room temperature for 30 min.] The solution was then diluted with ethyl acetate, washed with water, dried with sodium sulfate, concentrated and chromatographed (silica gel, hexanes/EtOAc=1:2 to $CH_2Cl_2$/$CH_3OH$=9:1) to afford a green solid (37 mg, 84%): 1H NMR (400 MHz) δ 8.96 (s, 1H), 8.88 (s, 1H), 8.76 (d, J=4.5 Hz, 1H), 8.75 (d, J=4.5 Hz, 1H), 8.62 (d, J=4.7 Hz, 1H), 8.56 (d, J=4.7 Hz, 1H), 8.44 (d, J=8.1 Hz, 2H), 8.39 (s, 1H), 8.38 (s, 1H), 8.30 (d, J=8.0 Hz, 2H), 7.68-7.64 (m, 2H), 5.02 (br, 2H), 4.62 (s, 2H), 2.60 (s, 3H), 2.06 (s, 6H), 1.85 (s, 6H), −1.85 (br, s, 2H); 13C NMR (100 MHz) δ 165.7, 164.8, 163.5, 153.44, 153.38, 144.3, 140.8, 139.0, 138.0, 134.3, 132.1, 132.0, 128.9, 128.6, 128.5, 127.7, 126.8, 123.7, 88.75, 82.21, 53.77, 42.04, 31.14, 30.29, 29.65, 21.27, 18.40, 17.37, 12.06; MALDI-MS obsd 593.1 [(M+H)+], calcd 592.3 (M=$C_{38}H_{36}N_6O$).

2-[4-(2-Methoxy-2-oxoethyl)phenyl]ethynyl-9,10,16,17,23,24-hexaheptylphthalocyanine (5)

Follow a standard Sonogashira coupling reaction procedure, a solution of 4 (20 mg, 18 mol), methyl 3-(4-bromophenyl)propanoate (4.8 mg, 20 µmol), Pd(OAc)$_2$ (1.1 mg, 13 µmol) and P(o-tol)$_3$ (5.5 mg, 18 µmol) in deaerated toluene (6.0 mL) was deaerated by three freeze-pump-thaw cycles. The mixture was stirred at 60° C. for 18 h.

The resulting reaction mixture was concentrated and column chromatographed by a three-column strategy [(1) silica, $CH_2C2$, (2) SEC, toluene, (3) silica, $CH_2Cl_2$] to afford a green solid (3.0 mg, 13%). MALDI-MS: obsd 1289.4 [(M+H)+], calcd 1288.9 (M=$C_{86}H_{112}N_8O_2$).

2-[4-(N-Aminocarbamoyl)methylphenylethynyl]-9,10,16,17,23,24-hexaheptylphthalocyanine (D3)

A solution of 5 (3.0 mg, 2.3 μmol) in toluene (140 μL) was treated with 6.5 μL hydrazine hydrate (55% wt) and methanol (10 μL). The resulting mixture was stirred at 50° C. for 16 h, whereupon ethyl acetate and water were added to the mixture. The organic extract was washed with brine, dried ($Na_2SO_4$) and concentrated to afford a green solid, which is used directly in the next step of synthesis.

Example 2

The general approach for polymer preparation and derivatization according to some embodiments of the present invention is shown below in Scheme 6.

Scheme 6.

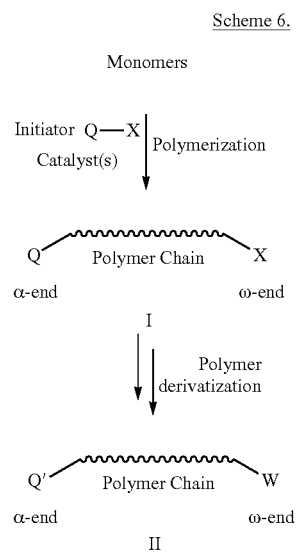

In the approach shown in Scheme 6, the initiator is Q-X, where X can be halo (e.g., Cl, Br, I) or sulfonate (e.g., triflate), and Q can carry a dye or can bear a functional group and remain intact through the course of polymerization.

In the case of further derivatization, the functional group needed for dye attachment can be incorporated prior to polymerization (in the Q unit) and used directly. Alternatively, after polymerization, derivatization of Q in the synthetic polymer I can afford a modified Q (denoted Q') in polymer II for dye attachment.

The provisions for attachment to a biomolecule (ω-end of the polymer) exist in one case by direct use of the X-substituent in polymer I. Alternatively, the X-group can be substituted to give a functional group W in polymer II for attachment of the biomolecule. Examples of W include azido, isocyanato, isothiocyanato, active esters (e.g., pentafluorophenyl ester, succinimido ester, 2,4-dinitrophenyl ester), maleimido, vinyl, mercapto, amino, and carboxylic acid. The derivatization at the ω-end in polymer I can be achieved through a single step or multiple steps (e.g. nucleophilic substitution and/or deprotection) to give the desired functional group W in polymer II. For the pre-polymerization method, the functional groups are installed first into the initiator (the Q unit of Q-X, Scheme 6), and remain intact through the course of polymerization.

Some examples of Q and Q-X are shown in Scheme 7. As shown in Scheme 7, Q may include hydroxy,[1,2] carboxy,[3] amino,[4] formyl,[4] vinyl,[5,6] epoxy, anhydride,[8] haloary,[7] ester,[3] or oxazoline[8] group. Vinyl or allyl groups can be installed through the initiator and may remain intact during the polymerization without causing extra trouble upon cross-linking.[1,5,6] This can be achieved by selecting the appropriate ligands, predominantly in the presence of a copper(I) catalyst. However, some functional groups that are commonly used for dye attachment (e.g., azido groups) or bioconjugation cannot be installed by pre-polymerization method (shown in Table 6).

Scheme 7. Functional groups compatible with pre-polymerization installation.

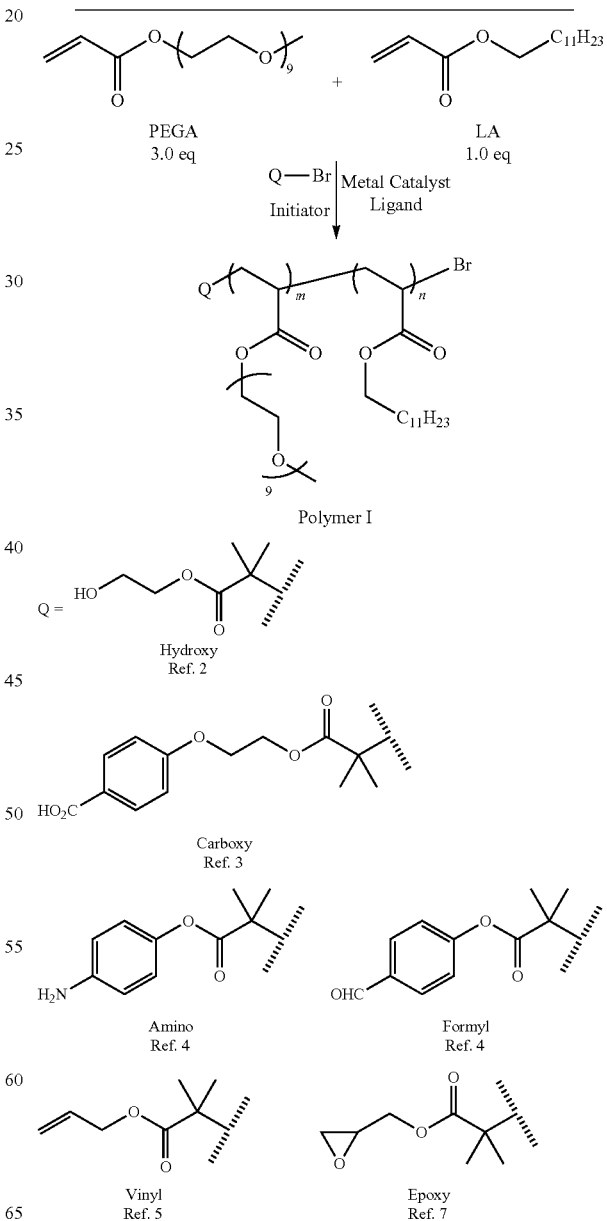

-continued

Other possible initiators

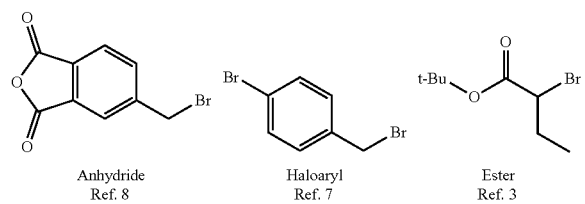

| Anhydride | Haloaryl | Ester |
|---|---|---|
| Ref. 8 | Ref. 7 | Ref. 3 |

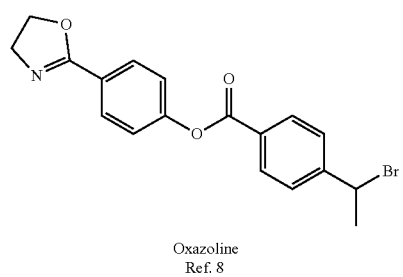

Oxazoline
Ref. 8

TABLE 6

Commonly used functional groups that need to be installed after polymerization.

| Functional group on the copolymer after derivatization | Chemistry |
|---|---|
| Azido | Copper-catalyzed alkyne-azide 'click' chemistry |
| Pentafluorophenyl | Amide formation |
| Succinimido | Amide formation |
| Fluorophenyl | Aromatic nucleophilic substitution |
| Maleimido | Thiol-ene reaction |
| Isocyanato | Amine-isocyanate chemistry |
| Isothiocyanato | Amine-isothiocyanate chemistry |

It is noted that the example discussed here describes attachment of the dye to the α-end of the polymer and the biomolecule to the ω-end of the polymer. However, the utilization of the two ends can be reversed as desired, whereupon the biomolecule is attached to the α-end of the polymer and the dye to the ω-end of the polymer.

REFERENCES (1) Kamigaito, M.; Ando, T.; Sawamoto, M. Metal-Catalyzed Living Radical Polymerization. *Chem. Rev.* 2001, 101, 3689-3745.

(2) Haddleton, D. M.; Waterson, C.; Derrick, P. J.; Jasieczek, C. B.; Shooter, A. J. Monohydroxy Terminally Functionalized Poly(methyl methacrylate) from Atom Transfer Radical Polymerisation. *Chem. Commun.* 1997, 683-684.

(3) Zhang, X.; Matyjaszewski, K. Synthesis of Functional Polystyrenes by Atom Transfer Radical Polymerization Using Protected and Unprotected Carboxylic Acid Initiators. *Macromolecules* 1999, 32, 7349-7353.

(4) Haddleton, D. M.; Waterson, C. Phenolic Ester-Based Initiators for Transition Metal Mediated Living Polymerization. *Macromolecules* 1999, 32, 8732-8739.

(5) Zeng, F.; Shen, Y.; Zhu, S.; Pelton, R. Synthesis and Charaterization of Comb-Branched Polyeletrolytes. 1. Preparation of Cationic macromonomer of 2-(Dimethylamino)ethyl Methacrylate by Atom Transfer Radical Polymerization. *Macromolecules* 2000, 33, 1628-1635.

(6) Shen, Y.; Zhu, S.; Zeng, F.; Pelton, R. Synthesis of Methacrylate Macromonomers Using Silica Gel Supported Atom Transfer Radical Polymerization. *Macromol. Chem. Phys.* 2000, 201, 1387-1394.

(7) Zhang X.; Xia, J.; Matyjaszewski K. End-Functional Poly(tert-butyl acrylate) Star Polymers by Controlled Radical Polymerization. *Macromolecules* 2000, 33, 2340-2345.

(8) Malz, H.; Komber, H.; Voigt, D.; Hopfe, I., Pionteck, J. Synthesis of Functional Polymers by Atom Transfer Radical Polymerization. *Macromol. Chem. Phys.* 1999, 200, 642-651.

Example 3—Example Reactions

An exemplary reaction for preparing a compound of the present invention that includes cross-linking is provided in Scheme 8.

Scheme 8. Exemplary reaction with cross-linking step.

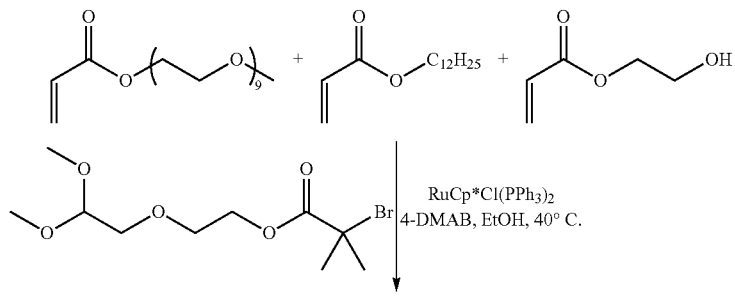

-continued
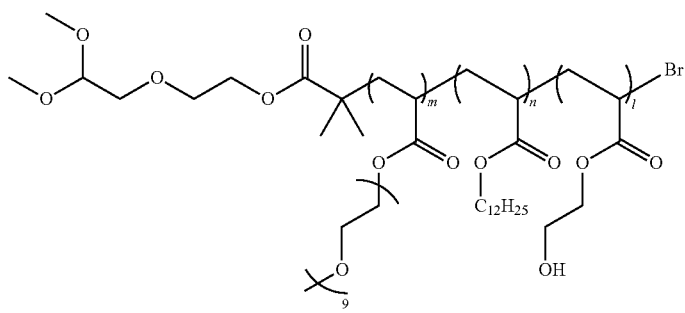
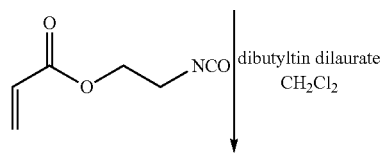
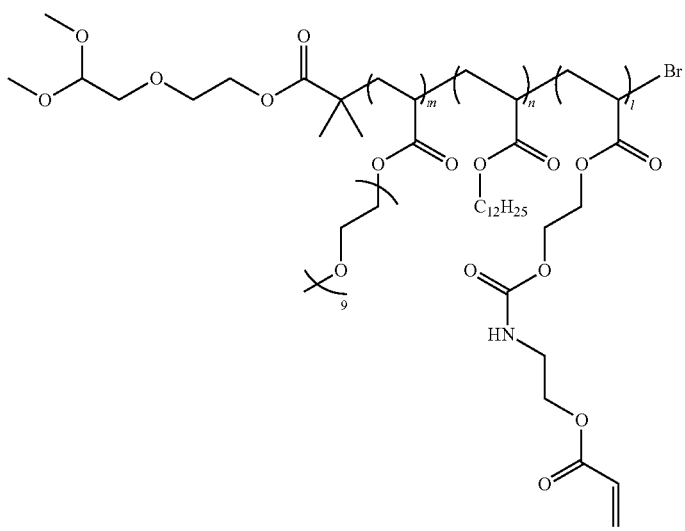
bioconjugation / deprotection (1) H$_2$N-PEG$_{12}$-CO$_2$H, DMF, hydroquinone, rt
(2) TFA/CH$_2$Cl$_2$ (1:1), hydroquinone, rt
fluorophore attachment 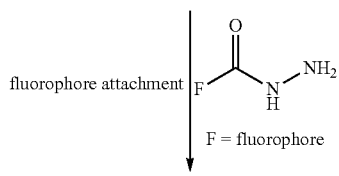
F = fluorophore -continued
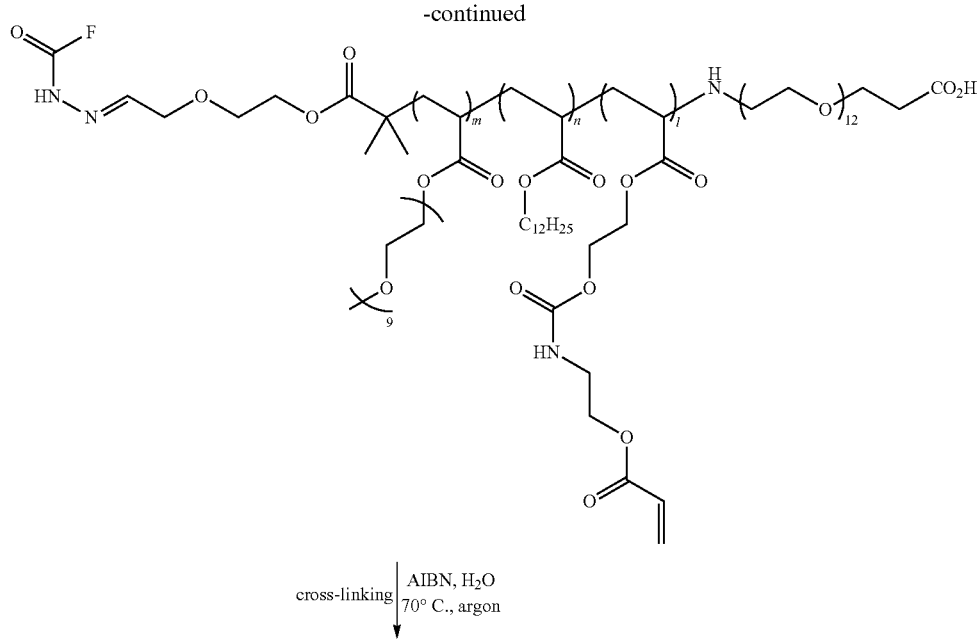
An exemplary reaction for preparing a compound of the present invention that includes sulfonation and cross-linking is provided in Scheme 9.
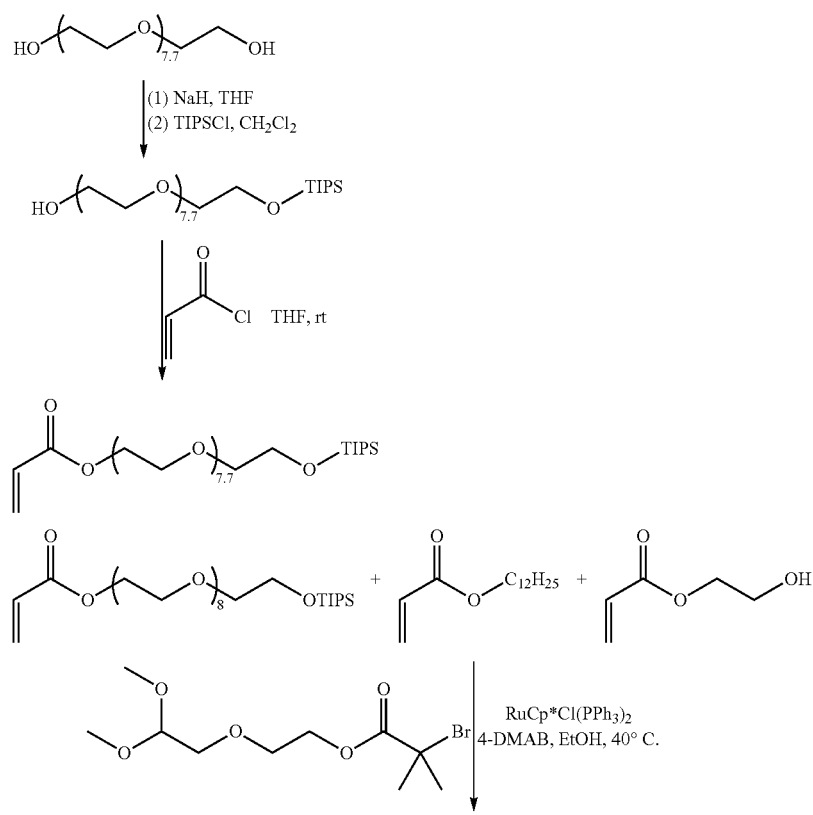
Scheme 9: Exemplary reaction with a sulfonation and cross-linking step.

-continued
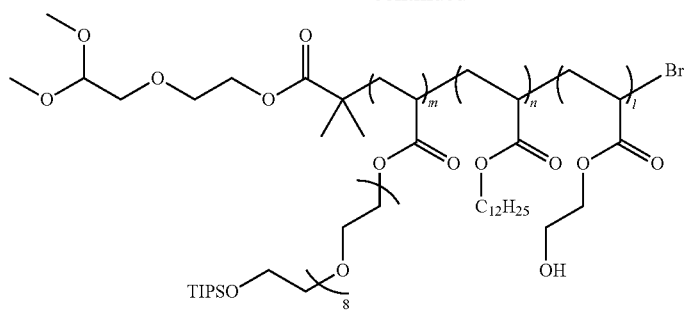
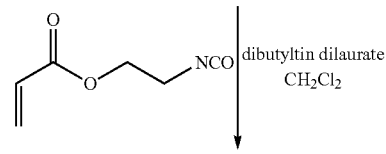
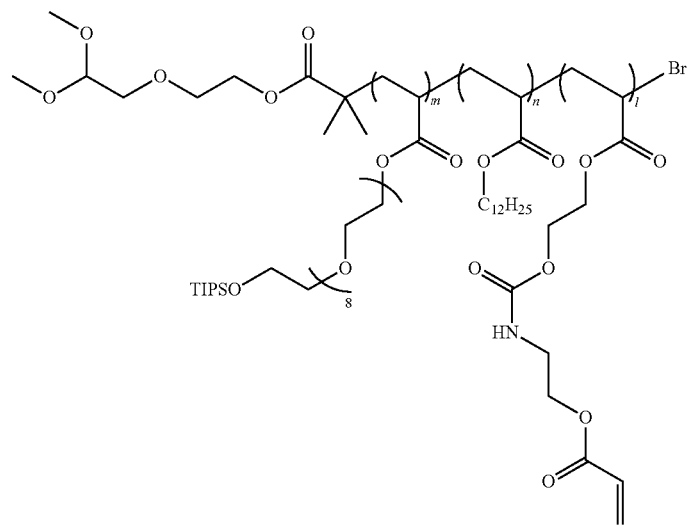
(1) TBAF, THF
(2) NaH, THF
(3) 1,3-propanesultone, THF
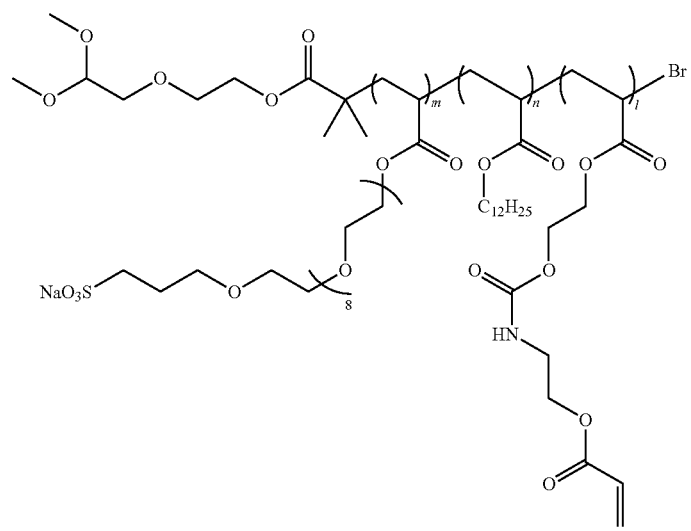
HCl, ethyl acetate

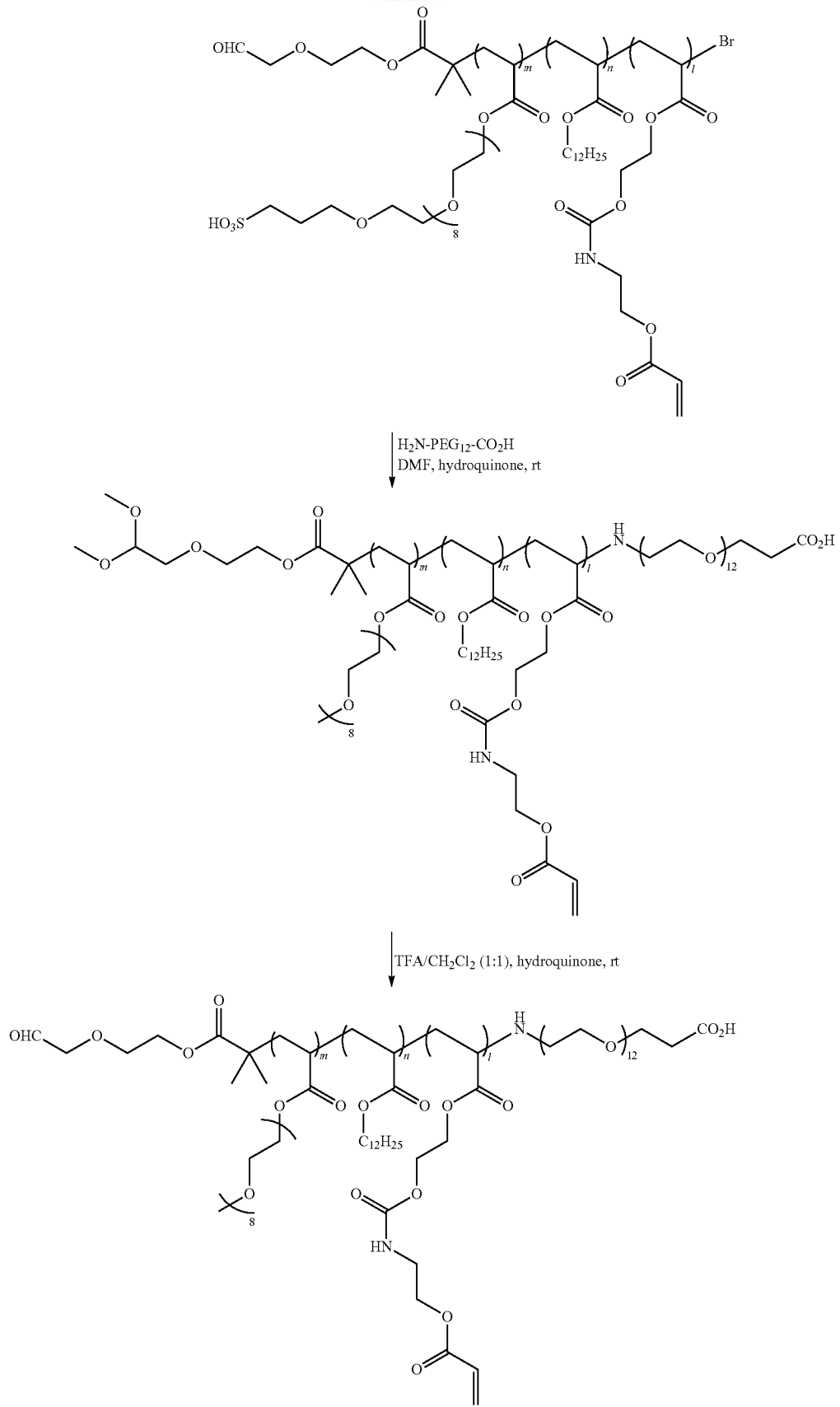

Example 4

An example approach for polymer preparation and derivatization according to some embodiments of the present invention is shown below in Scheme 10.

Scheme 10. Example synthesis of a heterotelechelic random copolymer via RAFT.

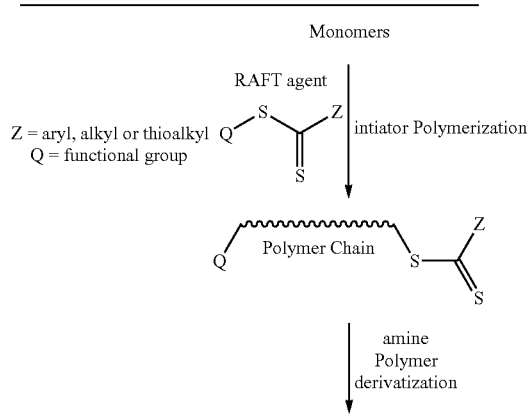

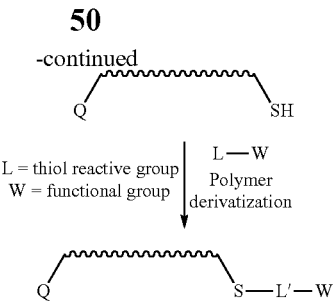

In the approach shown in Scheme 10, Z in the RAFT agent is aryl, alkyl or thioalkyl, and Q can bear a functional group that remains intact through the course of polymerization.

In the case of further derivatization, the functional group needed for attachment to a dye or biomolecule can be incorporated prior to polymerization (in the Q unit) and used directly. Such functional groups can be installed first into the Q unit of the RAFT agent and remain intact through the course of polymerization. Alternatively, after polymerization, derivatization of Q in the synthetic polymer can afford a modified Q for dye or biomolecule attachment.

Some examples of Z and Q in the RAFT agent are shown in Chart 1. Examples of Z in the RAFT agent include, but are not limited to, phenyl (optionally substituted) and/or thioalkyl groups (including branched and/or unbranched C1-C25 thioalkyl groups).

Examples of Q in the RAFT agent include, but are not limited to, carboxylate, azido, hydroxy, N-succinimidyl, vinyl, phthalimido, and/or biotinyl.

CHART 1

Examples of RAFT agents that can provide terminal functional groups.

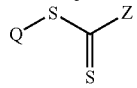

Functionalized RAFT agent

| Z = phenyl | Z = thioalkyl |
|---|---|
| 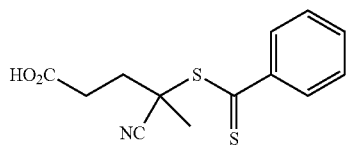 Q includes Carboxyl Ref. 9 | 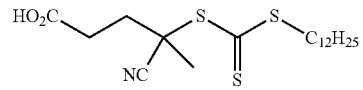 Q includes Carboxyl Ref. 14 |
| 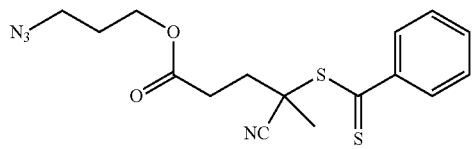 Q includes Azido Ref. 10 | 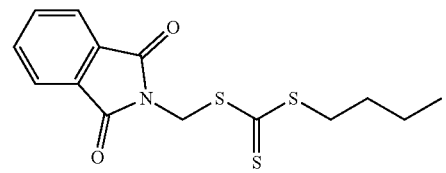 Q includes Phthalimido Ref. 15 |
| 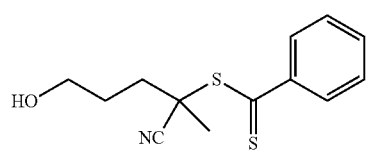 Q includes Hydroxyl Ref. 11 | 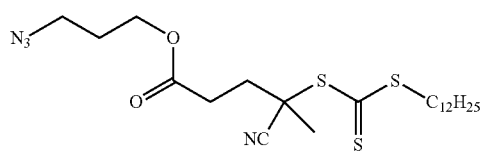 Q includes Azido Ref. 10 |

CHART 1-continued

Examples of RAFT agents that can provide terminal functional groups.

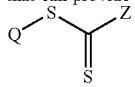

Functionalized RAFT agent

| Z = phenyl | Z = thioalkyl |
|---|---|
| 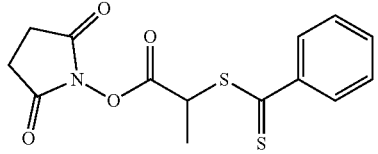 | 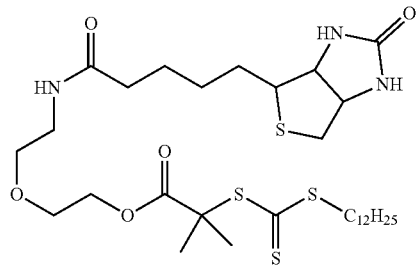 |
| Q includes N-succinimidyl Ref. 12 | Q includes biotinyl Ref. 16 |
| 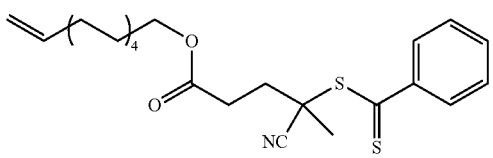 | |
| Q includes Vinyl Ref. 13 | |

Prior to attaching a dye or biomolecule at the terminal end of the polymer comprising the thiocarbonylthio group, the thiol group can be liberated by cleavage of the thiocarbonylthio group using known methods in the art. The free thiol group can either couple directly with the dye or biomolecule or can be further modified with an agent L-W, to provide a capped thiol (e.g., thioether) with a suitable functional group W for coupling with the dye or biomolecule. Agent L-W includes a thiol reactive group L, which reacts with the free thiol group and also serves as a linker L' between the thiol and functional group W in the capped product.

Some examples of L and W in L-W are shown in Chart 2. Examples of L groups in the L-W agent include, but are not limited to, substituted halides (e.g., substituted benzyl bromides and/or a-acids), substituted alkynes (e.g., substituted benzyl alkynes), substituted vinyl esters (e.g., a-vinyl esters), and/or substituted succinimides (e.g., ethylamine succinimide, ethanol succinimide).

Examples of functional group W include, but are not limited to, carboxylic acid (e.g., —COOH, —CH$_2$CH$_2$COOH), amino (e.g., —NH$_2$, —CH$_2$CH$_2$NH$_2$, optionally with a protecting group: NHBoc, —CH$_2$CH$_2$NHBoc), aldehyde, alcohol (e.g., —CH$_2$CH$_2$OH), and/or alkylated alcohols (e.g., —OCH$_2$CH$_2$OH, —OCH$_2$CH$_2$NHBoc, —OCH$_2$CH$_2$N$_3$, —OC≡CH, —OCH$_2$CH═CH$_2$).

Derivatization of the free thiol group can be achieved through a single step or multiple steps (e.g. nucleophilic substitution and/or deprotection) to give the desired functional group W.

CHART 2

Examples of thiol reactive groups with additional functional groups.
L—W examples
L = thiol reactive groups
W = functional groups

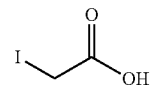

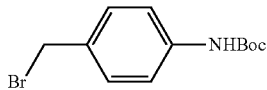

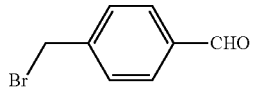

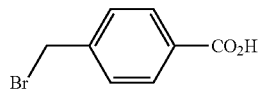 [SMILES: O=C(O)c1ccc(CBr)cc1]

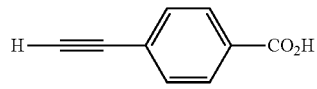

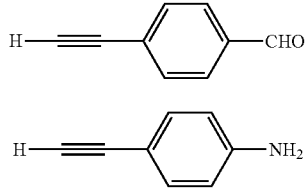

CHART 2-continued

Examples of thiol reactive groups with additional functional groups.
L—W examples
L = thiol reactive groups
W = functional groups

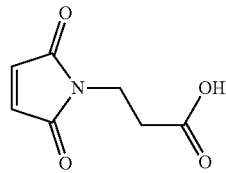 [SMILES: O=C(O)CCN1C(=O)C=CC1=O]

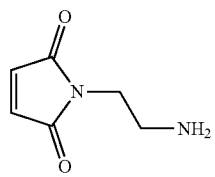

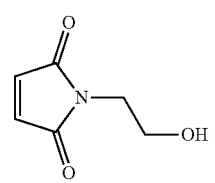

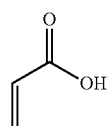

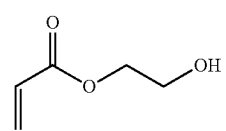

CHART 2-continued

Examples of thiol reactive groups with additional functional groups.
L—W examples
L = thiol reactive groups
W = functional groups

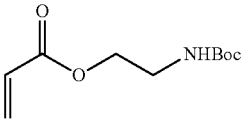

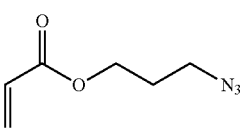

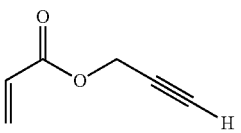

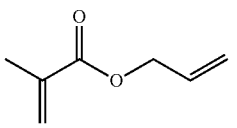

A further example of a RAFT polymerization is shown in Scheme 11. Hydrophobic monomer dodecyl methyl acrylate (LA) is polymerized with hydrophilic monomers 2-acrylamido-2-methylpropane sulfonic acid as the sodium salt (AMPS) and PEGylated methyl acrylate (PEGA) in the presence of a RAFT agent and radical initiator to generate a polymer. In some embodiments, one or more functional group(s) are present (e.g., pre-installed) on the RAFT agent prior to polymerization. Examples of such functional group(s) are shown in Scheme 11. After polymerization, the pre-installed functional group(s) will be located at one terminal end of the polymer and can be used for coupling to a biomolecule or dye.

Scheme 11. Functional groups preinstalled on RAFT agent.

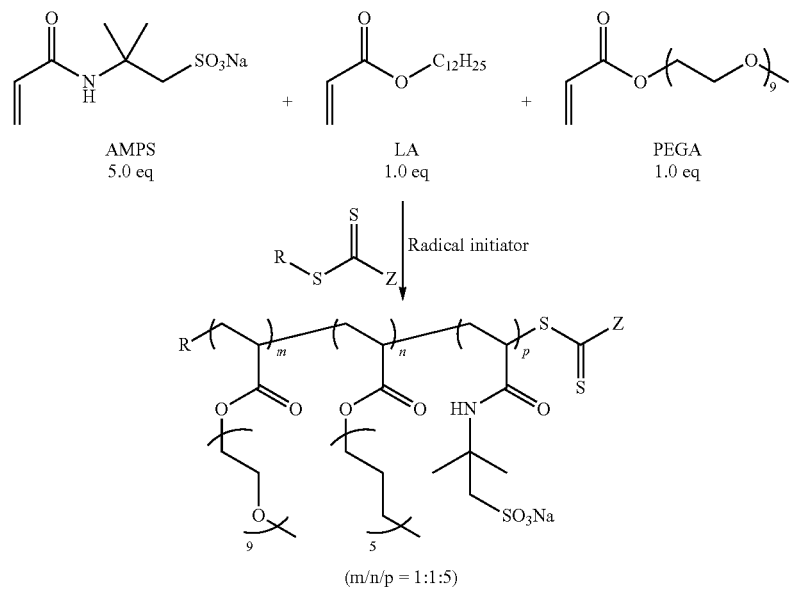

Z = phenyl

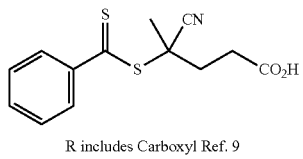

R includes Carboxyl Ref. 9

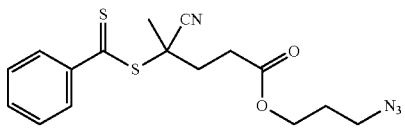

R includes Azido Ref. 10

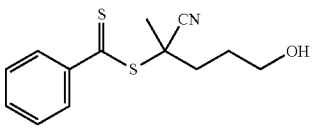

R includes Hydroxyl Ref. 11

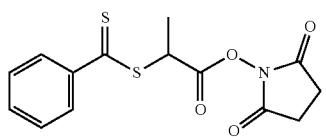

R includes N-succinimidyl Ref. 12

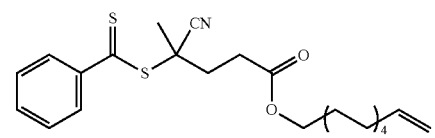

R includes Vinyl Ref. 13

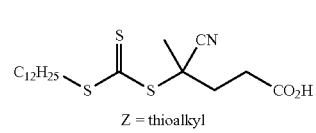

Z = thioalkyl
R includes Carboxyl
Ref. 14

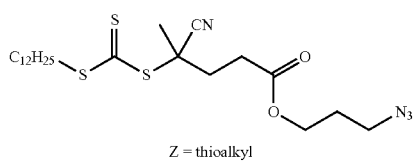

Z = thioalkyl
R includes Azido
Ref. 10

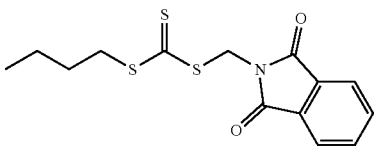

Z = alkyl
R includes Phthalimido
Ref. 15

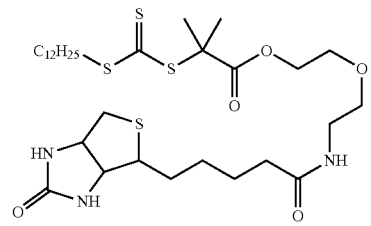

Z = thioalkyl
R includes biotinyl
Ref. 16

REFERENCES (9) Sumerlin, B. S.; Donovan, M. S.; Mitsukami, Y.; Lowe, A. B.; McCormick, C. L. Water-Soluble Polymers. 84. Controlled Polymerization in Aqueous Media of Anionic Acrylamido Monomers via RAFT. *Macromolecules* 2001, 34, 6561-6564.

(10) Gondi, S. R.; Vogt, A. P.; Sumerlin, B. S. Versatile Pathway to Functional Telechelics via RAFT Polymerization and Click Chemistry. *Macromolecules* 2007, 40, 474-481.

(11) Chong, Y. K.; Krstina, J.; Le, T. P. T.; Moad, G.; Postma, A.; Rizzardo, E.; Thang, S. H. Thiocarbonylthio Compounds [S=C(Ph)S—R] in Free Radical Polymerization with Reversible Addition-Fragmentation Chain Transfer (RAFT Polymerization). Role of the Free-Radical Leaving Group (R). *Macromolecules* 2003, 36, 2256-2272.

(12) Bathfield, M.; D'Agosto, F.; Spitz, R.; Charreyre M.; Delair, T. Versatile Precursors of Functional RAFT Agents. Application to the Synthesis of Bio-Related End-Functionalized Polymers. *J Am. Chem. Soc.* 2006, 128, 2546-2547.

(13) Patton, D. L.; Advincula, R. C. A Versatile Synthetic Route to Macromonomers via Polymerization. *Macromolecules* 2006, 39, 8674-8683.

(14) Moad, G.; Chong, Y. K.; Postma, A.; Rizzardo, E.; Thang, S. H. *Polymer* 2005, 46, 8458-8468.

(15) Postma, A.; Davis, T. P.; Evans, R. A.; Li, G.; Moad, G.; O'Shea, M. S. Synthesis of Well-Defined Polystyrene with Primary Amine End Groups through the Use of Phthalimido-Functional RAFT Agents. *Macromolecules* 2006, 39, 5293-5306.

(16) Hong, C-Y.; Pan, C-Y. Direct Synthesis of Biotinylated Stimuli-Responsive Polymer and Diblock Copolymer by RAFT Polymerization Using Biotinylated Trithiocarbonate as RAFT Agent. *Macromolecules* 2006, 39, 3517-3524.

Example 5 Synthesis of an Amphiphilic Random Copolymer Via Reversible Addition-Fragmentation Chain Transfer (RAFT) Polymerization A model study of the synthesis of a sulfonated amphiphilic random copolymer is shown in Scheme 12. Three monomers were employed, one of which was hydrophobic (dodecyl methyl acrylate (LA)) and two that were hydrophilic (2-acrylamido-2-methylpropane sulfonic acid as the sodium salt (AMPS) and PEGylated methyl acrylate (PEGA)). AMPS can be prepared by basifying commercially available 2-acrylamido-2-methylpropane sulfonic acid with sodium hydroxide and/or basifying the commercially available sodium salt of 2-acrylamido-2-methylpropane sulfonic acid having small amounts of free acid present as a minor contaminant in the commercially available AMPS material. RAFT chain transfer agent 1 was used as it was available in the lab. Polymerizations with varying monomer ratios were carried out in DMF (80° C.) containing AIBN as radical initiator and mesitylene as internal standard. After polymerization, the crude product was poured into a large excess of ethyl ether to precipitate the polymer. Then the precipitate was dialyzed against water to give the purified polymer.

Scheme 12. Synthesis of sulfonated amphiphilic random copolymer via RAFT polymerization.

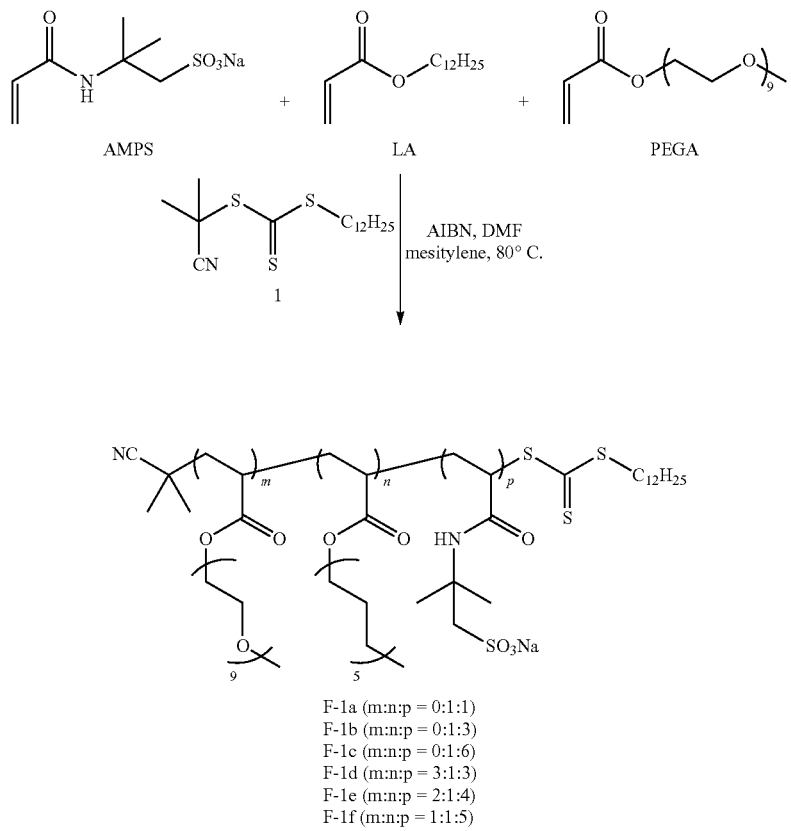

F-1a (m:n:p = 0:1:1)
F-1b (m:n:p = 0:1:3)
F-1c (m:n:p = 0:1:6)
F-1d (m:n:p = 3:1:3)
F-1e (m:n:p = 2:1:4)
F-1f (m:n:p = 1:1:5)

Dynamic Light Scattering (DLS) Size Analysis of the Amphiphilic Polymers.

Each polymer was dissolved in 1.0 M NaCl aqueous solution and passed through a 200 nm membrane filter. The filtrate was examined by DLS to determine the size of the nanoparticles. The DLS size data of the different polymers are summarized in Table 7. According to the data, for those polymers with no PEG groups, the best result was obtained with sulfonates and lauryl groups in a 6:1 ratio, which gave 65% unimer in aqueous solution. Upon introducing the PEG groups, the percentage of unimer was higher when the ratio of PEG groups and sulfonate groups was reduced from 1:1 to 1:5. At a ratio of AMPS:PEGA:LA=5:1:1, the unimer appeared to be the predominant species in aqueous solution.

TABLE 7

DLS size data of the polymers.

| Polymer | Initial monomer ratios (AMPS:PEGA:LA) | Unimer size (diameter in nm) | Aggregate size (diameter in nm) | Unimer intensity percentage (%) |
| --- | --- | --- | --- | --- |
| F1-a | 1:0:1 | — | 35 and 108 | 0 |
| F1-b | 3:0:1 | — | 145 | 0 |
| F1-c | 6:0:1 | 7.3 (10 mg/mL) | 24 and 274 (10 mg/mL) | 65 |
| F1-d | 3:3:1 | 13 (10 mg/mL) | 40 (10 mg/mL) | 65 |
| F1-e | 4:2:1 | 7.7 (10 mg/mL) | 69 (10 mg/mL) | 87 |

TABLE 7-continued

DLS size data of the polymers.

| Polymer | Initial monomer ratios (AMPS:PEGA:LA) | Unimer size (diameter in nm) | Aggregate size (diameter in nm) | Unimer intensity percentage (%) |
| --- | --- | --- | --- | --- |
| F1-f | 5:1:1 | 11 (10 mg/mL) | 200 (10 mg/mL) | 93 |
| F1-f | 5:1:1 | 10.9 (6.0 mg/mL) | — (6.0 mg/mL) | 100 |

Synthesis of the Polymer-Fluorophore Conjugate Via RAFT Polymerization.

The living radical polymerization of monomer PEGA, LA and AMPS was carried out in a 1:1:5 ratio (i.e., hydrophilic/hydrophobic ratio=6:1) with the RAFT agent 4-cyano-4-(phenylcarbonothioylthio)pentanoic acid 2 in the presence of the radical initiator 2,2'-azobis(2-methylpropionitrile) (AIBN) (Scheme 13). The resulting polymer 3 is heterotelechelic, containing a carboxyl group on one end and a thiocarbonylthio group at the other end. Aminolysis of polymer 3 with ethanolamine cleaved the thiocarbonyl group and revealed a free thiol group. Coupling of the latter with hydrophobic maleimido-substituted bacteriochlorin D1 in situ gave the target polymer-fluorophore conjugate F-2.

Scheme 13. Synthesis of polymer-fluorophore via RAFT Polymerization.

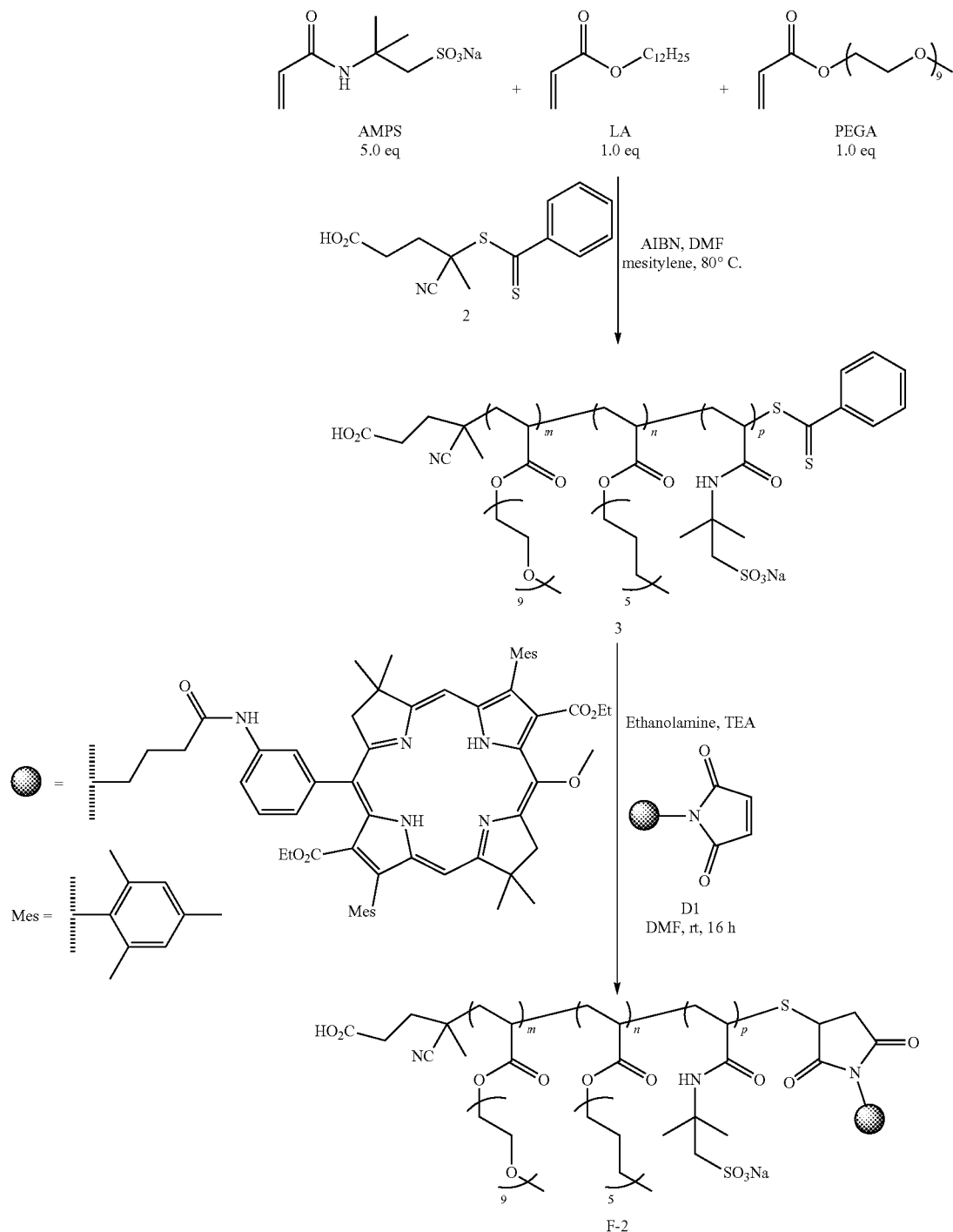

Dynamic Light Scattering (DLS) Size Analysis of the Polymer-Fluorophore Conjugate.

Figure 4:
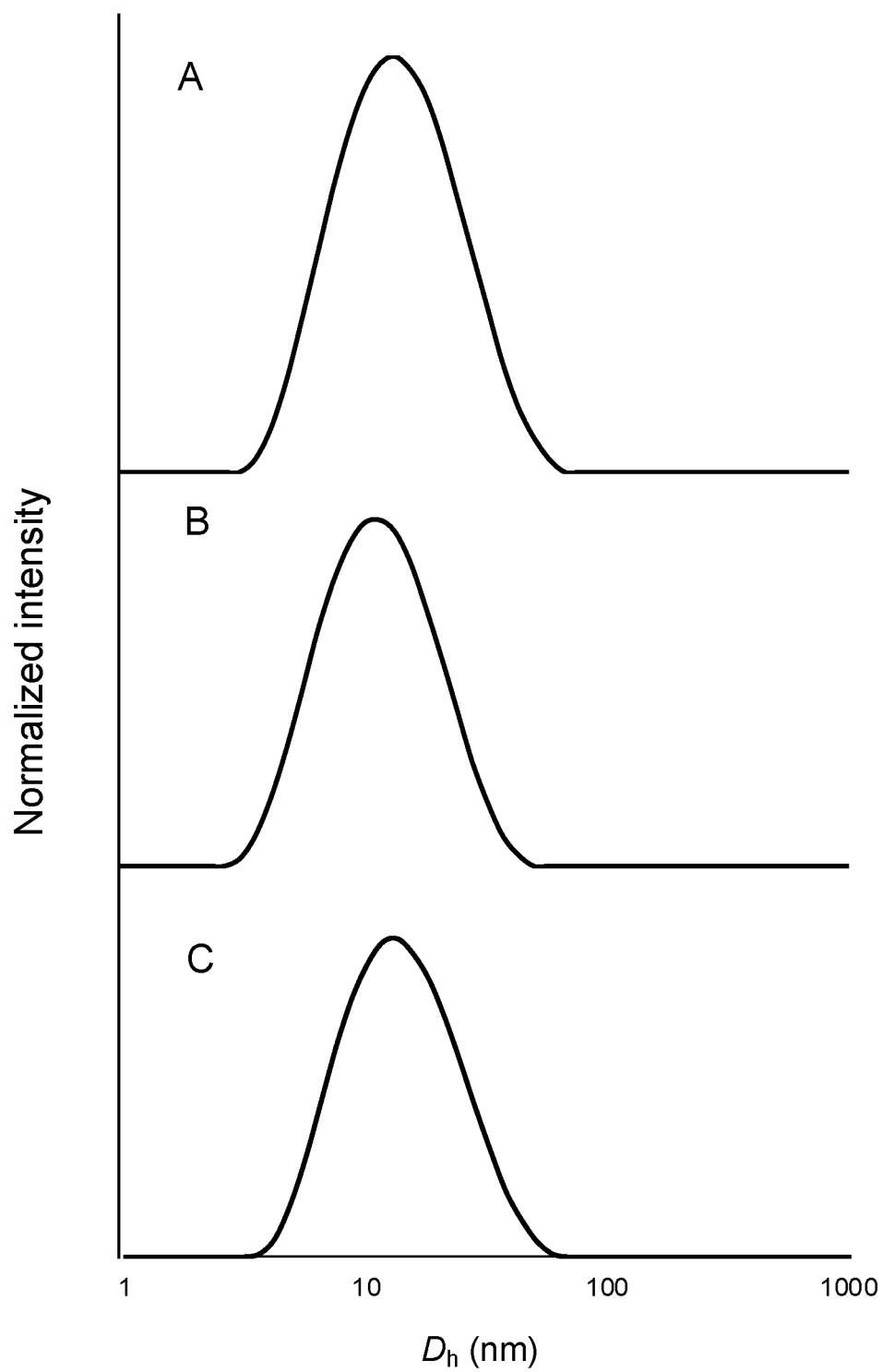
FIG. 4 shows dynamic light scattering (DLS) size data of F-2 at 10 mg/mL (A), 5 mg/mL (B) and 1.0 mg/mL (C).

The polymer-fluorophore sample was dissolved in 1.0 M NaCl aqueous solution and passed through a 200 nm membrane filter. The filtered solution was examined by DLS to determine the size of the nanoparticles. The DLS size data of the different polymers are summarized in Table 8. The polymer-fluorophore sample F-2 showed a unimeric form across a range of concentrations (FIG. 4).

TABLE 8

DLS size data of F-2 in aqueous solution.

| Entry | Compound | Particle size (nm in diameter) | Concentration (mg/mL) |
| --- | --- | --- | --- |
| 1 | 3 | 10.9 | 6.0 |
| 2 | F-2 | 16.22 | 10 |

TABLE 8-continued

DLS size data of F-2 in aqueous solution.

| Entry | Compound | Particle size (nm in diameter) | Concentration (mg/mL) |
|---|---|---|---|
| 3 | F-2 | 13.19 | 5.0 |
| 4 | F-2 | 15.73 | 1.0 |

Measurements of Absorption and Emission Spectra and Fluorescence Quantum Yield of F-2.

Figure 5:
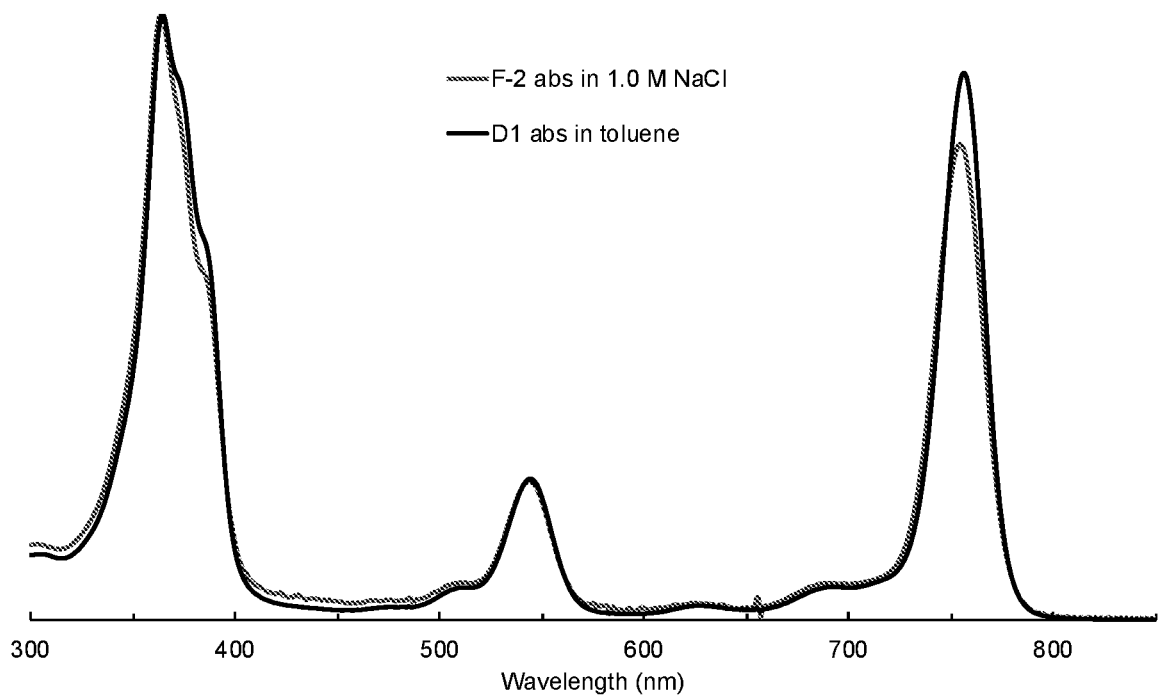
FIG. 5 shows absorption spectra of F-2 in 1.0 M NaCl solution (top) and water (bottom).
Figure 5:
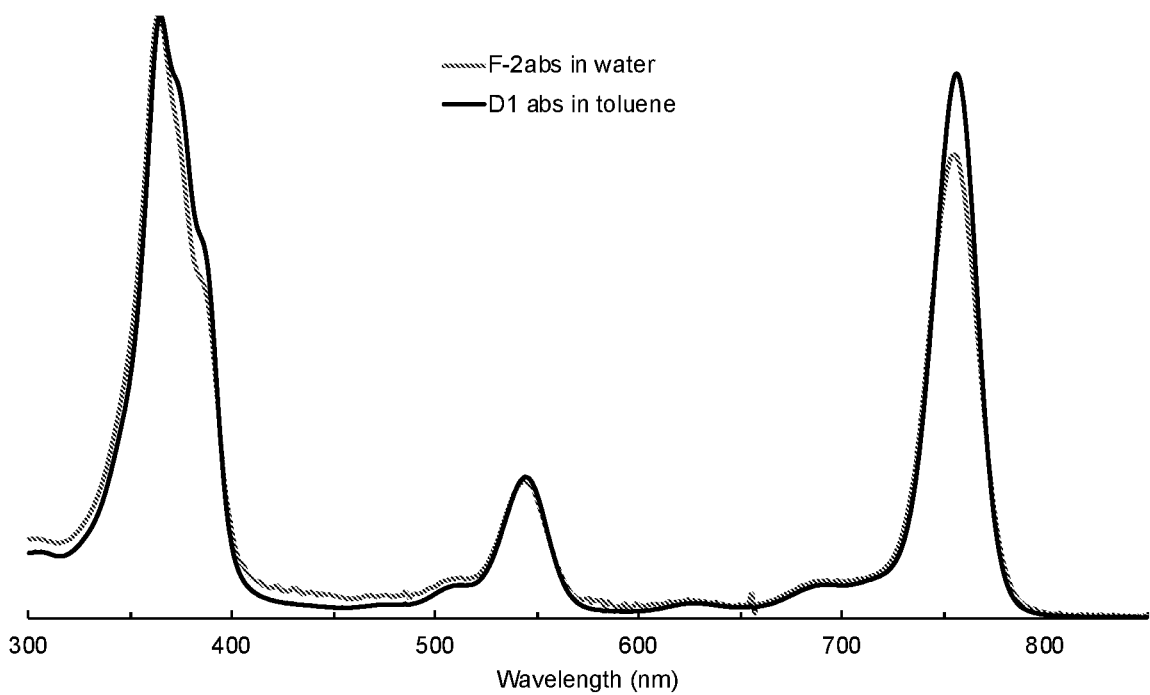
Figure 6:
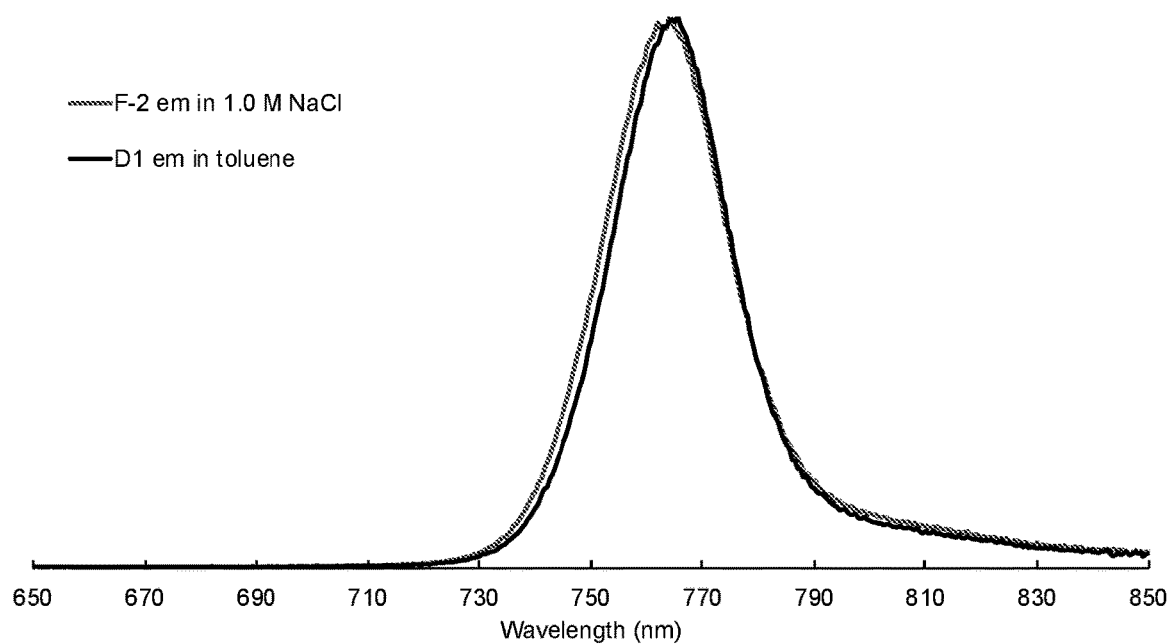
FIG. 6 shows emission spectra of F-2 in 1.0 M NaCl solution (top) and water (bottom).
Figure 6:
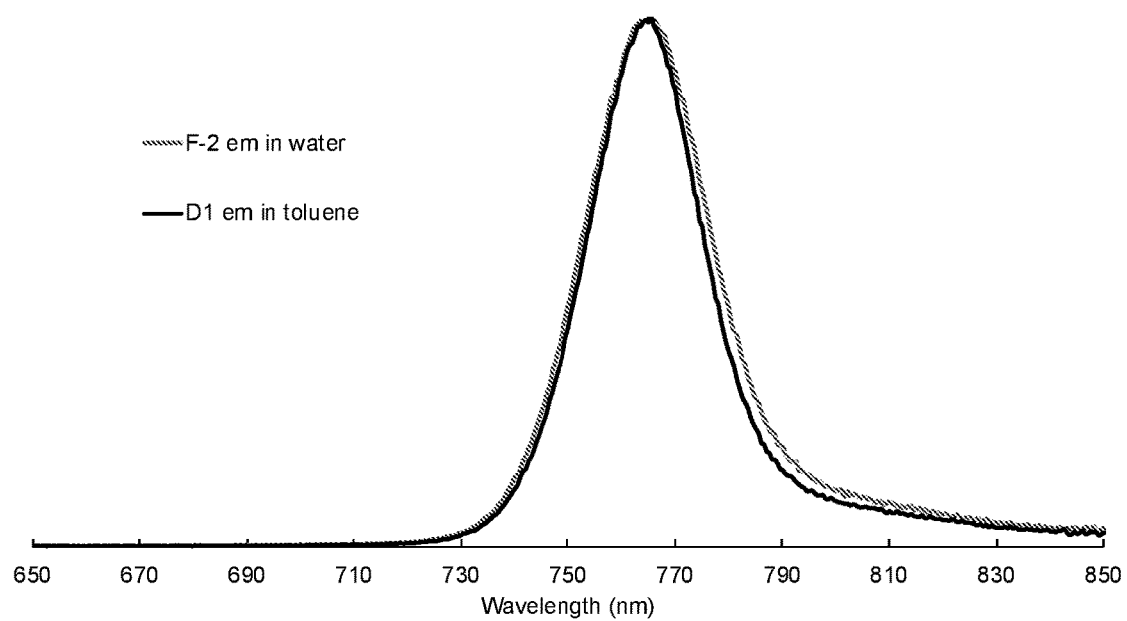

Absorption and emission spectra of the target polymer-fluorophore conjugate F-2 were measured at room temperature in both water and aqueous buffer solution (FIG. 5 and FIG. 6). Spectroscopic data and fluorescence quantum yield data are summarized in Table 9.

The absorption and emission spectra of F-2 in aqueous solution are comparable to D1 in toluene with minimal broadening and decrease of $Q_y$ absorbance. The fluorescence yields of F-2 in aqueous media are 93% (in buffer) and 80% (in water) versus that of D1 in toluene. These data are consistent with insignificant fluorophore aggregation in aqueous media. A single fluorophore is encapsulated in an amphiphilic polymer and maintains the intrinsic fluorescence upon immersion in an aqueous environment.

TABLE 9

Spectroscopic data and fluorescence quantum yields of F-BC in aqueous solution.

| Entry | Compound | Solvent | $\lambda_{exc}$ (nm) | $\lambda_{em}$ (nm) | fwhm at $\lambda_{em}$ (nm) | $\Phi_f$ percentage of D1 in toluene |
|---|---|---|---|---|---|---|
| 1 | F-2 | 1.0M NaCl solution | 544 | 764 | 26 | 93% |
| 2 | F-2 | Water | 544 | 765 | 27 | 80% |
| 3 | D1 | toluene | 544 | 765 | 25 | 100% |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A compound having a structure represented by:

A-B-C, or

C-A-B wherein
A is a dye;
B is a polymer having a polymer backbone comprising one or more hydrophobic unit(s) and one or more hydrophilic unit(s), wherein the polymer backbone comprises a first terminus and a second terminus, wherein the first terminus and the second terminus are opposing ends of the polymer backbone; and
optionally C, wherein C comprises a bioconjugate group, wherein the dye is covalently attached to the first terminus or the second terminus of the polymer backbone,
wherein the one or more hydrophobic unit(s) have a structure represented by Formula III:

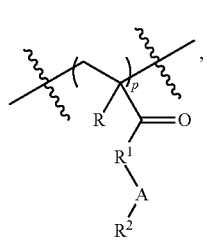

wherein:
R is hydrogen or $CH_3$;
$R^1$ is —O— or —NH—;
A is a C1-C20 alkyl, C2-C20 alkenyl, or C2-C20 alkynyl;
$R^2$ is hydrogen or a halo, hydroxyl, carboxyl, amino, formyl, vinyl, epoxy, mercapto, ester, azido, maleimido, isocyanato, or isothiocyanato group; and
p is an integer from 1 to 10, 100, 1,000, 5,000, 10,000, 50,000, or 100,000, and
wherein the one or more hydrophilic unit(s) have a structure represented by Formula IV:

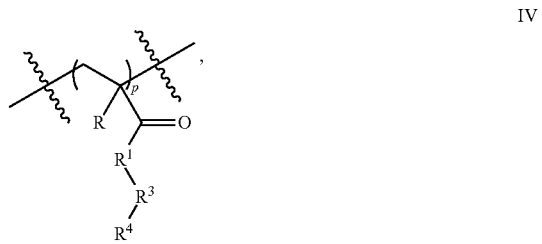

wherein:
R is hydrogen or $CH_3$;
$R^1$ is —O— or —NH—;
$R^3$ is selected from the group consisting of —($CH_2CH_2O$)$_n$—, —$C_1$-$C_6$alkyl, and —$C_1$-$C_6$alkyl-$SO_3$— or a salt thereof, wherein n is an integer from 1 or 5 to 10, 25, 50, 75, 100, 1,000, 5,000, or 10,000;
$R^4$ is absent or is a hydrogen, alkyl, phosphono, sulfono, phosphatidyl choline, phosphoryl, halo, hydroxyl, carboxyl, amino, ammonio, formyl or ester group; and
p is an integer from 1 to 10, 100, 1,000, 5,000, 10,000, 50,000, or 100,000.

2. The compound of claim 1, wherein the one or more hydrophobic unit(s) and the one or more hydrophilic unit(s) are randomly distributed in the polymer.

3. The compound of claim 1, wherein the one or more hydrophobic unit(s) and the one or more hydrophilic unit(s) are present in the polymer in a ratio of about 1:1, 1:2, 1:3, 1:4, 1:5, 1:6, 1:7, 1:8, 1:9, or 1:10.

4. The compound of claim 1, wherein the compound is self-folding in an aqueous solution.

5. The compound of claim 1, wherein the dye is encapsulated by a portion of the compound when the compound is in a folded structure.

6. The compound of claim 1, wherein the polymer is a telechelic polymer or a heterotelechelic polymer.

7. The compound of claim 1, wherein the compound has a solubility in water at room temperature in a range of about 1 mg/mL to about 10 mg/mL.

8. The compound of claim 1, wherein at least one of the one or more hydrophobic unit(s) and/or the one or more hydrophilic unit(s) comprises a pendant functional group, optionally wherein the pendant functional group is a halo, hydroxyl, carboxyl, amino, formyl, vinyl, epoxy, mercapto, ester, azido, maleimido, isocyanato, isothiocyanato, phosphono, sulfono, ammonio, or phosphatidyl choline group.

9. The compound of claim 1, wherein at least one of the one or more hydrophobic unit(s) comprises an alkyl pendant group and/or at least one of the one or more hydrophilic unit(s) comprise a glycol pendant group.

10. The compound of claim 1, wherein the polymer is attached to one dye.

11. The compound of claim 1, wherein, in Formula III,
R is hydrogen;
$R^1$ is —O—; and
p is an integer from 1 to 50.

12. The compound of claim 1, wherein, in Formula IV,
R is hydrogen;
$R^1$ is —O—; and
p is an integer from 1 to 50.

13. A biomolecule comprising a compound of claim 1.

\* \* \* \* \*

UNITED STATES PATENT AND TRADEMARK OFFICE
CERTIFICATE OF CORRECTION

PATENT NO. : 12,139,617 B2
APPLICATION NO. : 16/955152
DATED : November 12, 2024
INVENTOR(S) : Lindsey et al.

Page 1 of 2

It is certified that error appears in the above-identified patent and that said Letters Patent is hereby corrected as shown below:

In the Specification

Column 9, Line 65: Please correct "C1" to read --C11--

Column 10, Line 34: Please correct "R in" to read --$R^4$ in--

Column 11, Line 13: Please correct "R in" to read --$R^2$ in--

Column 17, Lines 64-65: Please correct "10, 9,8, 7,6, 5,4, 3,2-fold" to read --10, 9, 8, 7, 6, 5, 4, 3, 2-fold--

Column 18, Lines 3-4: Please correct "1,2,3, 4, 5,6, 7,8, 9, or 10" to read --1, 2, 3, 4, 5, 6, 7, 8, 9, or 10--

Column 18, Line 17: Please correct "within 50%" to read --within ± 50%--

Column 35, Line 60: Please correct "[(M+H)+]" to read --[(M+H)$^+$]--

Column 36, Lines 64-65: Please remove the paragraph break between "18 h." and "The"

Column 36, Line 67: Please correct "$CH_2C_2$," to read --$CH_2Cl_2$,--

Column 37, Line 2: Please correct "[(M+H)+]" to read --[(M+H)$^+$]--

Column 37, Line 55: Please correct "o-end" to read --ω-end--

Column 38, Line 5: Please correct "epoxy, anhydride,$^8$ haloary,$^7$" to read --epoxy,$^7$ anhydride,$^8$ haloaryl,$^7$--

Signed and Sealed this
First Day of July, 2025

Coke Morgan Stewart
*Acting Director of the United States Patent and Trademark Office*

In the Claims

Column 63, Lines 1-2, Claim 8: Please correct "group, optionally wherein the pendant" to read --group, and the pendant--